United States Patent [19]

Awaya et al.

[11] Patent Number: 4,959,368

[45] Date of Patent: Sep. 25, 1990

[54] THERAPEUTIC AGENT FOR NEUROLOGICAL DISEASES

[75] Inventors: Akira Awaya; Takuo Nakano, both of Yokohama; Hisashi Kobayashi, Mobara; Ken E. Tan, Kamakura; Kazutoshi Horikomi; Tadayuki Sasaki, both of Mobara; Keiichi Yokoyama; Hiroyasu Ohno, boh of Iwakuni; Kozi Kato, Yamaguchi; Takumi Kitahara; Ikuo Tomino, both of Ohtake; Shigeru Isayama, Tokyo, all of Japan

[73] Assignees: Mitsui Petrochemical Industries Ltd.; Mitsui Pharmaceuticals, Inc., both of Tokyo, Japan

[21] Appl. No.: 130,533

[22] PCT Filed: Feb. 24, 1987

[86] PCT No.: PCT/JP87/00120

§ 371 Date: Oct. 22, 1987

§ 102(e) Date: Oct. 22, 1987

[87] PCT Pub. No.: WO87/04928

PCT Pub. Date: Aug. 27, 1987

[30] Foreign Application Priority Data

Feb. 24, 1986 [JP] Japan .................. 61-37244
Mar. 31, 1986 [JP] Japan .................. 61-73443

[51] Int. Cl.$^5$ ................ A61K 31/505; C07D 403/04; C07D 403/14
[52] U.S. Cl. ..................... 514/252; 514/215; 514/183; 514/221; 514/254; 540/460; 540/501; 540/521; 544/295; 544/250; 544/256; 544/262; 544/278; 544/279; 544/280; 544/292; 544/287; 544/288; 544/253
[58] Field of Search ............... 514/258, 260, 269, 273, 514/215, 183, 221, 252, 254; 540/460; 544/295, 262, 280, 288, 283, 286

[56] References Cited

U.S. PATENT DOCUMENTS 4,535,080 8/1985 Audiau et al. .................. 514/255

FOREIGN PATENT DOCUMENTS 115714 8/1984 European Pat. Off. .
57-179167 11/1982 Japan .
59-1554316 9/1984 Japan .

Primary Examiner—John M. Ford
Attorney, Agent, or Firm—Sherman and Shalloway

[57] ABSTRACT

A pharmaceutical composition comprising a pyrimidine represented by the following formula

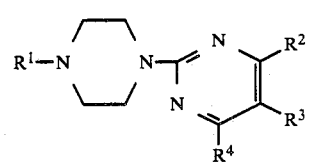

(I)

wherein $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms, or a hydroxyethyl group, $R^2$ and $R^3$, together with the carbon atoms to which they are bonded, may form a 5- to 7-membered carbocyclic ring or a heterocyclic ring having N, O or S as the hetero atom, and $R^4$ represents a hydrogen atom, an alkyl group having 1 to 4 carbon atoms, or an alkylthio group having 1 to 4 carbon atoms, or a pharmaceutically acceptable salt thereof. The above active compound has activities of promoting growth of nerve cells, forming neurites, and restoring motor functions, and is useful as an agent for treating diseases of peripheral and central nerves.

43 Claims, No Drawings

THERAPEUTIC AGENT FOR NEUROLOGICAL DISEASES

TECHNOLOGICAL FIELD

This invention relates to a novel therapeutic agent for neurological diseases in the peripheral nervous system and the central nervous system of animals. More specifically, it relates to a novel therapeutic agent for neurological diseases comprising a particular 2-piperazinopyrimidine derivative or its pharmaceutically acceptable salt.

BACKGROUND TECHNOLOGY

In the therapy of neurological diseases, namely disorders in the central nervous system and the peripheral nervous system, therapeutic agents for the central nervous system have been vigorously studied and applied. In contrast, very few therapeutic agents for diseases of the peripheral nervous system, especially disorders of peripheral nerves, have been put to practical use worldwide.

Japanese Laid-Open Patent Publication No. 34912/1977 discloses a pharmaceutical comprising a dispersion or solution of ganglioside in a medium, which is effective for pathology attributed to neural stimulus transmission disorders in the central nervous system and the peripheral nervous system. Only ganglioside (a product named Cronassial is sold in Italy), a natural carbohydrate, disclosed in the above-cited laid-open publication and mecobalamin, a kind of vitamin, have so far been applied clinically to diseases of the peripheral nervous system, but no entirely satisfactory effect has been obtained.

Japanese Patent Publication No. 28548/1984 discloses 2-isopropylaminopyrimidine ortho-phosphate represented by the following formula

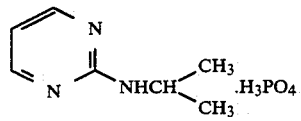

and a therapeutic agent comprising this compound for treatment of peripheral nerve diseases. As far as the present inventors know, the above compound (common name, isaxonine phosphate to be abbreviated hereinafter as isaxonine) is the first synthetic compound which was used in clinical research on peripheral nerve disorders (La Nouvelle Presse Medicale, vol. 16, pages 1189–1280, 1982). It appears that this compound is not actually marketed now. No synthetic compound has been known which is used for treating peripheral nerve disorders.

Factors acting on the growth and regeneration of nerves are known to exist in an animal. They are called a nerve growth factor (NGF) or a neurotrophic factor. These factors are high-molecular proteins, and many problems exist which have to be technically solved in applying them to neurological diseases.

Japanese Laid-Open Patent Publication No. 222424/1984 discloses that a gangliside mixture extracted from the cow brain or a single component in gangliosides acts promotingly on the proliferation of the primary culture of nerve cells or neuroblastoma cells, and the formation and growth of the neurite, and that it has the same effect as mecobalamin in an animal model of neurological disorder. Furthermore, as stated above, ganglioside is actually used clinically for the treatment of disorders in the peripheral nervous system and the central nervous system (not psychopathy).

Ganglioside, however, is a natural extract originated from an animal of a different species, and the antigenicity of itself or a foreign material contained in it becomes a problem. Another problem is that it is very difficult to specify and define it as a uniform stable substance in drug preparation.

Japanese Laid-Open Patent Publication No. 144,765/1984 discloses a 2-(1-piperazinyl)pyrimidine having the following formula (I)

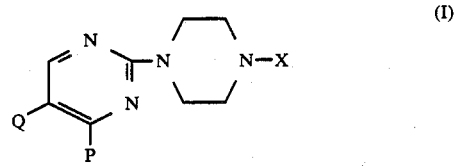

wherein one of P and Q represents hydrogen or a hydroxyl or lower alkyl group and the other represents hydrogen, and X represents a group of the formula $CO-R_1$ in which $R_1$ is a lower alkyl group, a group of the formula

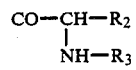

in which $R_2$ is hydrogen or a lower alkyl, phenyl, p-hydroxyphenyl, benzyl, p-hydroxybenzyl, hydroxymethyl, 1-hydroxyethyl or 3-indolylmethyl group, $R_3$ is hydrogen, a lower alkylcarbonyl group, a benzoyl group, an acyl group derived from an amino acid selected from glycine, phenylglycine, alanine, valine, leucine, isoleucine, phenylalanine, tyrosine, serine, threonine and tryptophan, or an acyl group derived from a dipeptide comprised of two of the above amino acids, or $R_2$ and $R_3$ together may form an ethylene group, a group of the formula $Alk-COOY$ in which Alk represents a liner or branched alkylene group having 1 to 4 carbon atoms and Y represents hydrogen or a lower alkyl group, a group of the formula $Alk-CH_2OZ$ in which Alk is as defined, and Z represents hydrogen or a lower alkyl, (lower alkoxy)-lower alkyl, or lower alkylcarbonyl group, or a group of the formula $Alk-CO-W$ in which Alk is as defined and W represents a lower alkyl group or its pharmaceutically acceptable acid addition salts. This patent document states that the compounds of formula (I) or acid addition salts thereof have dopamine-type psychotherapeutic activity.

Japanese Laid-Open Patent Publication No. 144,766/1984 describes an acid addition salt of 2-(1-piperazinyl)pyrimidine with a dicarboxylic acid, and states that this compound has good phrenotropic activity having dopamine mechanism, particularly antipsychotic activity, antimelanchoric activity and ataractic and tranguilizing activity.

Japanese Laid-Open Patent Publication No. 155,316/1984 discloses a drug having dopamine-acting phrenotropic activity comprising as an active ingredient a 2-piperazinopyrimidine represented by the formula

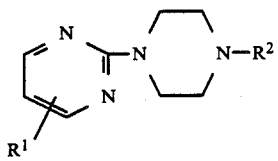

wherein $R^1$ represents hydrogen or a hydroxyl group, and $R^2$ represents hydrogen or an alkyl group having 1 to 6 carbon atoms, or a pharmacologically acceptable acid addition salt thereof.

International Laid-Open WO85/00168 discloses 2-(1-piperazinyl)pyrimidine 2-naphthalenesulfonate represented by the following formula

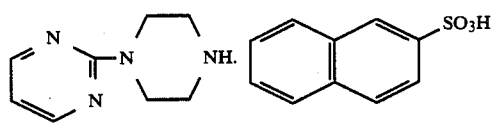

and states that this compound has dopamine phrenotropic activity.

However, none of the above four cited patent documents describe or suggest that 2-piperazinopyrimidines are effective for reproducing neurocytes and can be applied to peripheral nerve disorders, and central nerve disorders which are not psychopathy.

It is an object of this invention therefore to provide a novel therapeutic agent for neurological diseases.

Another object of this invention provides a novel therapeutic agent for neurological diseases effective for reproducing and repairing neurocytes.

Still another object of this invention is to provide a novel therapeutic agent for neurological diseases which can be applied to disorders of peripheral nerves.

Yet another object of this invention is to provide a novel therapeutic agent for neurological disorders which can be applied to central nerve disorders that are regarded as being primarily due to the involvement of derangement of the active and metabolic systems of nerve transmitting substances.

Further objects of this invention along with its advantages will become apparent from the following description.

According to this invention, the above objects and advantages of this invention are achieved by a therapeutic agent for neurological diseases, comprising as an active ingredient a pyrimidine represented by the following formula (I)

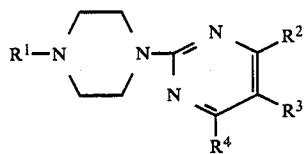

wherein
$R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group,
$R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms, or a hydroxyethyl group, $R^2$ and $R^3$, together with the carbon atoms to which they are bonded, may form a 5- to 7-membered carbocyclic ring or a heterocyclic ring having N, O or S as the hetero atom, and $R^4$ represents a hydrogen atom, an alkyl group having 1 to 4 carbon atoms, or an alkylthio group having 1 to 4 carbon atoms;
or a pharmaceutically acceptable salt thereof.

In formula (I), $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a benzyl group, or a 3,4-methylenedioxybenzyl group.

Examples of the acyl group having 2 to 4 carbon atoms are acetyl, propionyl, butyroyl and isobutyroyl groups.

Examples of the alkoxycarbonyl group having 2 to 5 carbon atoms are methoxycarbonyl and ethoxycarbonyl groups.

Examples of the alkoxycarbonylmethyl group having 3 to 5 carbon atoms are methoxycarbonylmethyl and ethoxycarbonylmethyl groups.

In formula (I), $R^2$ represents a hydrogen atom, an amino group, a monoalkylamino group having 1 to 4 carbon atoms, an alkoxy group having 1 to 5 carbon atoms, or an alkoxycarbonyl group having 2 to 4 carbon atoms.

Examples of the monoalkylamino group having 1 to 4 carbon atoms are methylamino, ethylamino, propylamino, isopropylamino and sec-butylamino groups.

Examples of the alkoxy group having 1 to 5 carbon atoms are methoxy, ethoxy, propoxy, iso-propoxy, butoxy, sec-butoxy, iso-butoxy and tert-butoxy groups.

Examples of the alkoxycarbonyl groups having 2 to 4 carbon atoms may be the same as those given above for $R^1$.

In formula (I), $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms, or a hydroxyethyl group.

Examples of the alkoxycarbonyl group having 2 to 4 carbon atoms may be the same as those given hereinabove with regard to $R^1$.

Examples of the dialkylaminocarbonyl groups having 1 to 9 carbon atoms in each alkyl moiety are dimethylaminocarbonyl, diethylaminocarbonyl, diisopropylaminocarbonyl and dibutylaminocarbonyl groups.

Examples of the alkoxy group having 1 to 5 carbon atoms may be the same as those given hereinabove in regard to $R^2$.

In formula (I), $R^2$ and $R^3$ may form a 4- to 7-membered carbocyclic ring or a heterocyclic ring having N, O or S as the hetero atom together with the carbon atoms to which they are bonded.

Examples of a group formed by $R^2$ and $R^3$ together are shown below.

 (a)

wherein $l_1$ is a number of 2, 3 or 4.

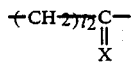 (b)

wherein X is =O or =N—$R^5$ in which $R^5$ represents a hydroxyl, benzylsulfonyloxy or toluenesulfonyloxy group, and $l_2$ represents a number of 2, 3, or 4.

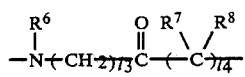 (c)

wherein $R^6$ represents a hydrogen atom, an alkyl group having 1 to 4 carbon atoms, or an alkoxy alkyl group resulting from substitution of an alkyl group having 2 to 4 carbon atoms by an alkoxy group having 1 to 4 carbon atoms, $R^7$ and $R^8$ are identical or different and each represents a hydrogen atom or an alkyl group having 1 to 4 carbon atoms, $l_3$ is 2 and $l_4$ is 0, or $l_3$ is 0 and $l_4$ is 1.

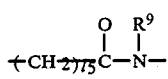 (d)

wherein $R^9$ represents a hydrogen atom or an alkyl group having 1 to 4 carbon atoms, and $l_5$ is a number of 2 or 3.

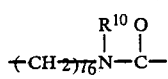 (e)

wherein $R^{10}$ represents a hydrogen atoms, an alkyl group having 1 to 10 carbon atoms, an acyl group having 1 to 4 carbon atoms, or a carbamoylmethyl group, and $l_6$ is a number of 1 or 2.

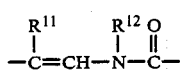 (f)

wherein $R^{11}$ represents a hydrogen atom, a formyl group, an alkyl group having 1 to 4 carbon atoms, or an aralkyl group having 7 to 9 carbon atoms, and $R^{12}$ represents a hydrogen atom, an alkyl group having 1 to 4 carbon atoms, an alkenyl group having 3 to 4 carbon atoms, a hydroxyalkyl group having 2 to 4 carbon atoms, an alkoxyalkyl group resulting from substitution of an alkyl group having 2 to 4 carbon atoms by an alkoxy group having 1 to 4 carbon atoms, a benzyl group, or a cycloalkyl group having 3 to 6 carbon atoms,

 (g)

wherein $R^{13}$ and $R^{14}$ are identical or different, and each represents a hydrogen atom or an alkyl group having 1 to 4 carbon atoms, and $l_7$ is a number of 0, 2 or 3,

 (h)

wherein E—G is —OCH$_2$CH$_2$—, —OC(CH$_3$)=CH—, —CH$_2$OCO—, —OCOCH$_2$—, —CH$_2$C(CH$_3$)OCO—, —N(CH$_3$)CH$_2$CH$_2$—, —CH=CH—CH=CH—, —CH=C(OCH$_3$)—C(OCH$_3$)=CH—, or

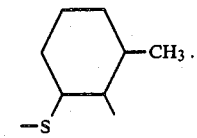

Examples of the alkyl group having 1 to 4 carbon atoms for $R^6$ in (c) above are methyl, ethyl, propyl, isopropyl, butyl, sec-butyl, iso-butyl and tert-butyl.

Examples of the alkoxyalkyl group for $R^6$ resulting from substitution of an alkyl group having 2 to 4 carbon atoms by an alkoxy group having 1 to 4 carbon atoms are methoxyethyl, ethoxyethyl, propoxyethyl, butoxyethyl, methoxypropyl and methoxybutyl.

Examples of the alkyl group having 1 to 4 carbon atoms for $R^7$ and $R^8$ are the same as those given hereinabove with regard to $R^6$.

Examples of the alkyl group having 1 to 4 carbon atoms for $R^9$ in (d) are the same as those given above with regard to $R^6$.

Examples of the alkyl group having 1 to 10 carbon atoms for $R^{10}$ in (e) above are methyl, ethyl, propyl, butyl, amyl, hexyl, heptyl, nonyl and decyl groups.

Examples of the acyl group having 1 to 4 carbon atoms for $R^{10}$ are formyl, acetyl, propionyl and butyroyl groups.

Examples of the alkyl group having 1 to 4 carbon atoms for $R^{11}$ in (f) are the same as those given above with regard to $R^6$.

Examples of the aralkyl group having 7 to 9 carbon atoms for $R^{11}$ are benzyl, 4-methylbenzyl, 4-methoxybenzyl, 4-nitrobenzyl, 2-phenylethyl and 3-phenylethyl groups.

Examples of the alkyl group having 1 to 4 carbon atoms for $R^{12}$ are the same as those given above with regard to $R^6$.

Examples of the alkenyl group having 3 to 4 carbon atoms for $R^{12}$ are allyl, 4-methylallyl and 3-methylallyl groups.

Examples of the hydroxyalkyl group having 2 to 4 carbon atoms for $R_{12}$ are 2-hydroxyethyl, 3-hydroxypropyl, 4-hydroxybutyl, 2-hydroxypropyl and 2-hydroxybutyl groups.

Examples of the alkoxyalkyl group resulting from substitution of an alkyl group having 2 to 4 carbon atoms by an alkoxy group having 1 to 4 carbon atoms may be the same as those given hereinabove with regard to $R^6$.

Examples of the alkyl group having 1 to 4 carbon atoms for $R^{13}$ and $R^{14}$ in (g) above may be the same as those given above with regard to $R^6$.

In formula (I), examples of the alkyl group having 1 to 4 carbon atoms for $R^4$ may be the same as those given above with regard to $R^6$.

Examples of the alkylthio group having 1 to 4 carbon atoms for $R^4$ are methylthio, ethylthio, propylthio, butylthio, isopropylthio, and sec-butylthio groups.

Specific examples of the compounds of formula (I) as the active ingredient of the therapeutic agent of this invention for neurological diseases are exemplified below in some groups divided according to the definitions of $R^2$ and $R^3$ for the sake of convenience.

Compounds in which $R^2$ and $R^3$ are not bonded to each other:

(100) 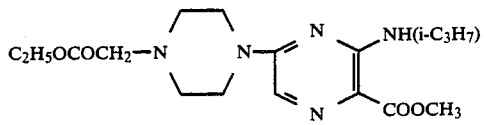 m.p. 78–79° C.

(102) 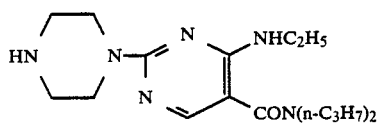

(104) Maleate of (102)

(106) 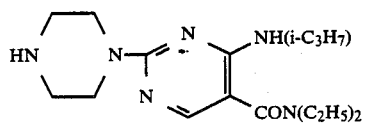

(108) Maleate of (106)

(110) 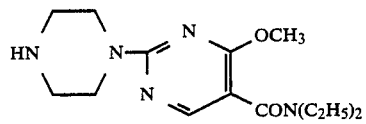

(112) Maleate of (110)

(114) 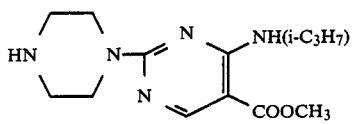

(116) Maleate of (114)

(118) 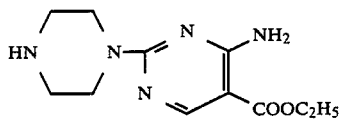

(120) Maleate of (118)

(122) 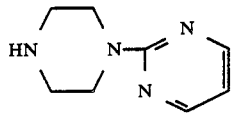

(124) Maleate of (122)

(126) 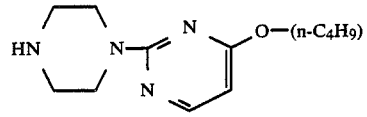

(128) Maleate of (126)

(130) 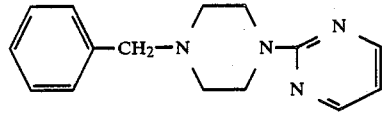

(132)  Maleate of (130)

(134) 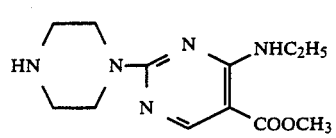

(136)  Maleate of (134)

(138) 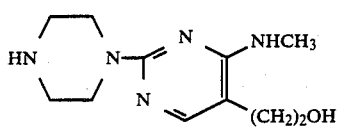   m.p. 195–197° C.

(140)  2-Naphthalenesulfonate of (140)   m.p. 215–217° C.

(142) 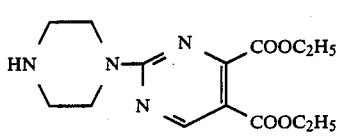

(144)  Hydrochloride of (142)

Compounds of the following formula (I)-a

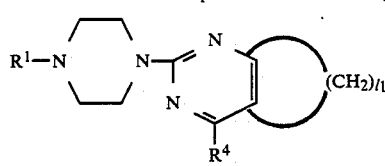 (I)-a wherein $R^1$, and $R^4$ and $l_1$ are as defined above, and $R^2$ and $R^3$ are bonded to each other to form the group $-(CH_2)_{l_1}-$ (200) 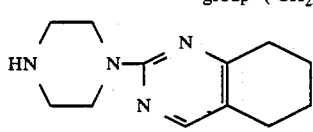   m.p. 107–113° C.

(202)  Hydrochloride of (200)   m.p. above 300° C.

(204) 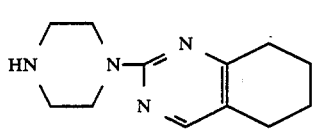

(206)  Maleate of (204)   m.p. 165–167° C.

(208) 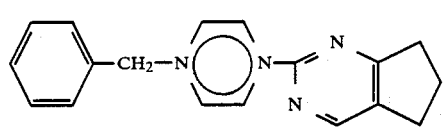   m.p. 90–95° C.

Compounds of the following formula (I)-b

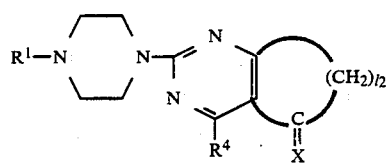 (I)-b wherein $R^1$, $R^4$, X and $l_2$ are as defined above, and $R^2$ and $R^3$ are bonded to each other to form the group 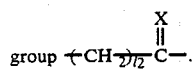

(300) 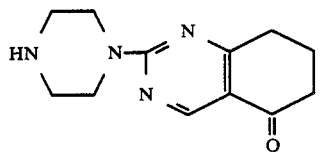
(302) Hydrochloride of (300)     m.p. 288–290° C. (decomp.)
(304) 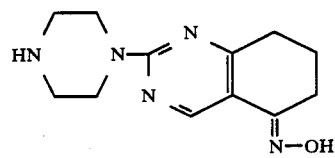
(306) 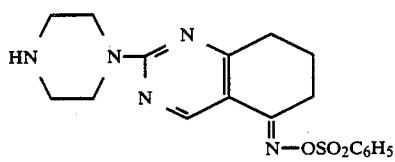
(308) 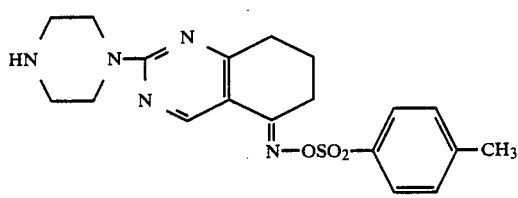
Compounds of the following formula (I)-c
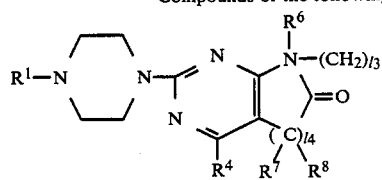     (I)-c
wherein $R^1$, $R^4$, $R^6$, $R^7$, $R^8$, $l_3$ and $l_4$ are as defined above, and $R^2$ and $R^3$ are bonded to each other to form the group $-\overset{R^6}{\underset{}{N}}-(CH_2)_{l_3}-\overset{O}{\underset{}{C}}-(\overset{R^7}{\underset{R^8}{C}})_{l_4}-$.
(400) 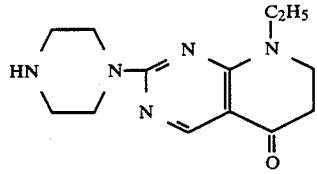
(402) 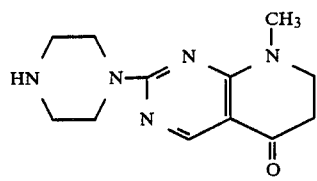
(404) 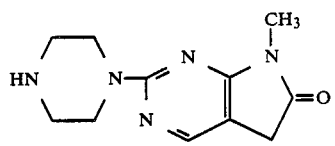
(406) Hydrochloride of (404)     m.p. above 300° C.
(408) Maleate of (404)     m.p. 179–182° C.

-continued
| | | |
|---|---|---|
| (410) | Oleate of (404) | m.p. 254–256° C. |
| (412) | p-Toluenesulfonate of (404) | m.p. 224–225° C. |
| (414) | Citrate of (404) | m.p. 187–188° C. |
| (416) | Tortrate of (404) | m.p. 230–232° C. (decomp.) |
| (418) | Phosphate of (404) | m.p. 286–289° C. (decomp.) |
| (420) | 2-Naphthalenesulfonate of (404) | m.p. 282–283° C. (decomp.) |
(422) 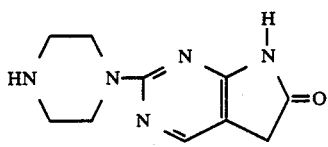
| | | |
|---|---|---|
| (424) | Hydrochloride of (422) | m.p. above 300° C. |
(426) 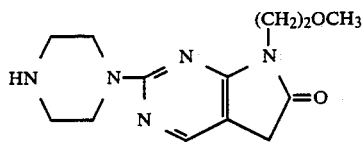
| | | |
|---|---|---|
| (428) | Hydrochloride of (426) | m.p. 257–259° C. |
| (430) | Maleate of (426) | m.p. 158–160° C. |
(432) 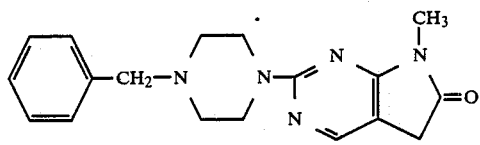
| | | |
|---|---|---|
| (434) | 2-Naphthalenesulfonate of (432) | m.p. 74–82° C. |
(436) 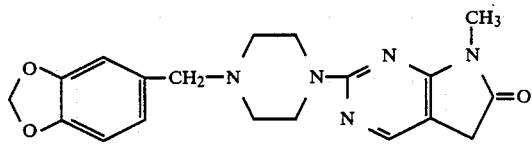
m.p. 122–124° C.
| | | |
|---|---|---|
| (438) | 2-Naphthalenesulfonate of (436) | m.p. 234–239° C. (decomp.) |
(440) 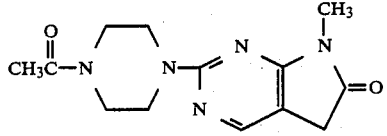
m.p. 194–195° C.
(442) 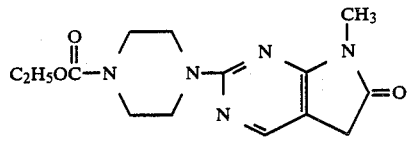
m.p. 170–171° C.
(444) 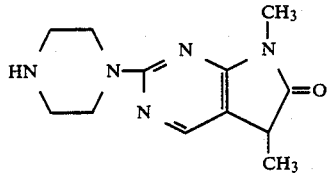
m.p. 167.2–169.2° C.
| | | |
|---|---|---|
| (446) | Maleate of (444) | m.p. 181–183° C. |
(448) 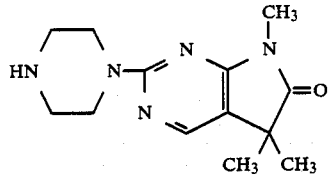
m.p. 113–116° C.

-continued
| | | |
|---|---|---|
| (450) | 2-Naphthalenesulfonate of (448) | m.p. 211–212° C. |
| (452) | 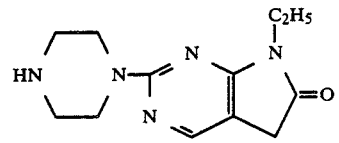 | |
| (454) | Hydrochloride of (452) | m.p. above 300° C. |
| (456) | 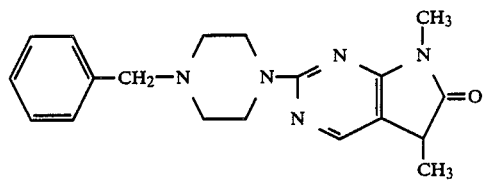 | m.p. 142–146° C. |
| (458) | 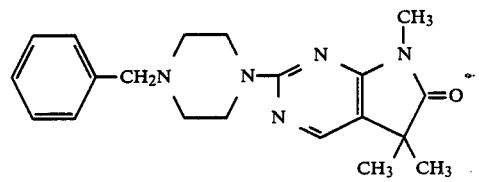 | m.p. 76–79° C. |
| (460) | 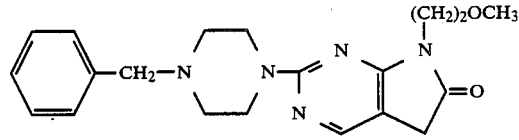 | |
| (462) | 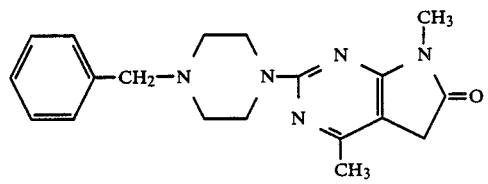 | |
| (464) | 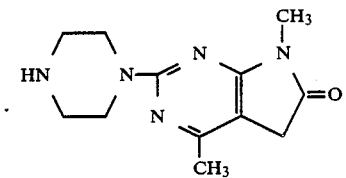 | |
| (466) | Hydrochloride of (464) | m.p. above 300° C. |
| (468) | Maleate of (464) | m.p. 181–183° C. (decomp.) |
Compounds of the following formula (I)-d
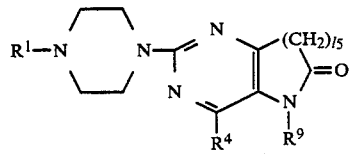
(I)-d
wherein $R^1$, $R^4$, $R^9$ and $l_5$ are as defined as above, and $R^2$ and $R^3$ are bonded to each other to form
the group 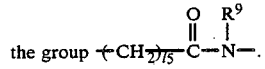.
(500) 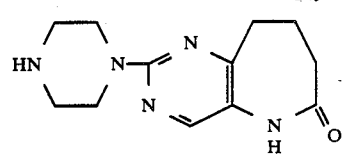

| | | |
|---|---|---|
| (502) | Hydrochloride of (500) | |
| (504) | 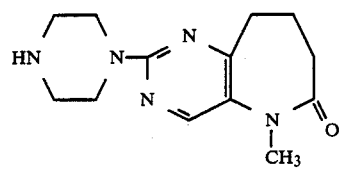 | |
| (506) | 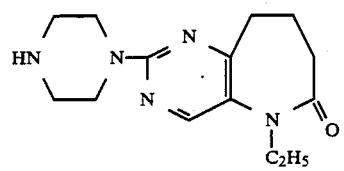 | |
Compounds of the following formula (I)-e
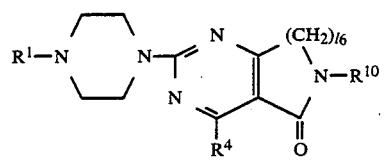 (I)-e
wherein $R^1$, $R^4$, $R^{10}$ and $l_6$ are as defined above, and $R^2$ and $R^3$ are bonded to each other to form
the group 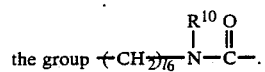.
| | | |
|---|---|---|
| (600) | 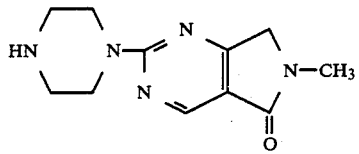 | m.p. 182–183° C. |
| (602) | Hydrochloride of (600) | m.p. above 300° C. |
| (604) | Maleate of (600) | m.p. 193–195° C. |
| (606) | Phosphate of (600) | m.p. above 300° C. |
| (608) | Naphthalenssulfonate of (600) | m.p. 272–273° C. |
| (610) | 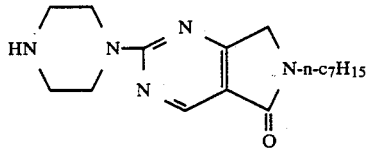 | |
| (612) | Hydrochloride of (610) | m.p. 245–250° C. |
| (614) | 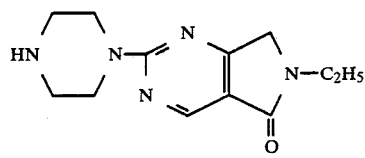 | |
| (616) | Hydrochloride of (614) | m.p. above 300° C. |
| (618) | 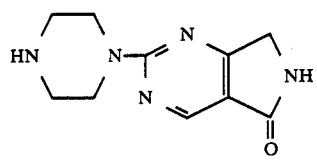 | |
| (620) | Hydrochloride of (618) | m.p. above 300° C. |

-continued
(622) 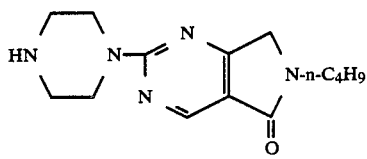
(624) Hydrochloride of (622)     m.p. 250–255° C. (decomp.)
(626) 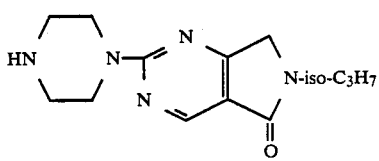
(628) Hydrochloride of (626)     m.p. 275–280° C.
(630) 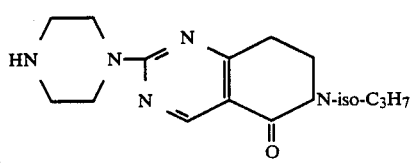
(632) 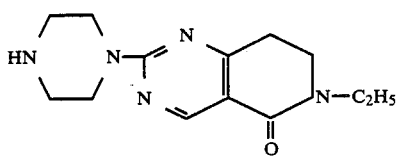
(634) 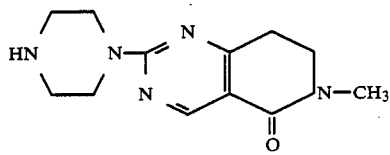
(636) 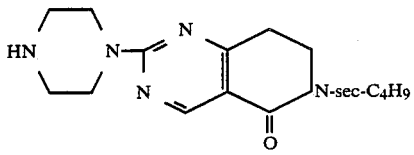     m.p. 110–115° C.
(638) Maleate of (636)     m.p. 151–152° C.
(640) 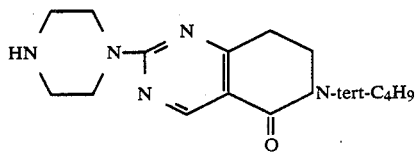     m.p. 162–164° C.
(642) Maleate of (640)     m.p. 202–203° C.
(644) 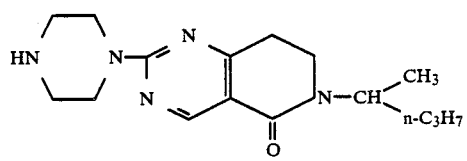     m.p. 106–112° C.
(646) Maleate of (644)     m.p. 134–136° C.

| | | |
|---|---|---|
| (648) | 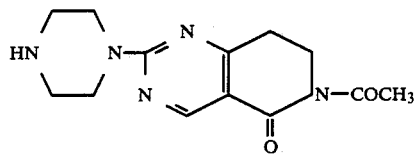 | |
| (650) | 2-Naphthalenesulfonate of (648) | m.p. 260–263° C. (decomp.) |
| (652) | 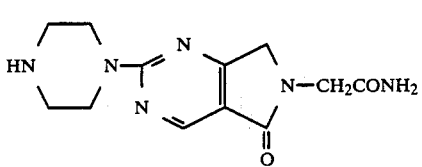 | m.p. 239–241° C. (decomp.) |
| (654) | 2-Naphthalenesulfonate of (652) | m.p. 276–277° C. (decomp.) |
| (656) | 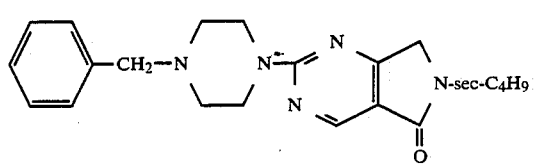 | m.p. 131–134° C. |
| (658) | 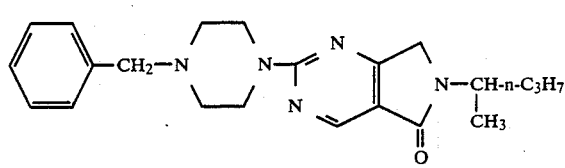 | m.p. 132–134° C. |
| (660) | 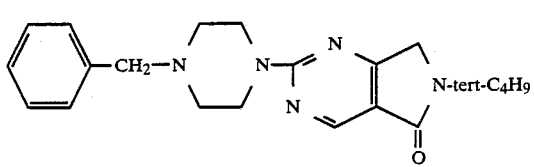 | m.p. 179–182° C. |
| (662) | 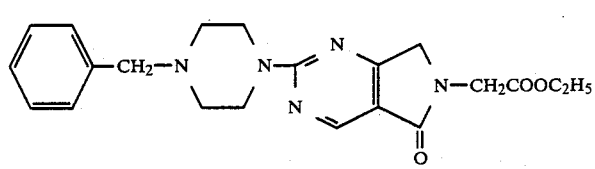 | m.p. 145–147° C. |
| (664) | 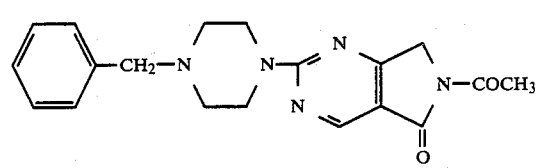 | m.p. 176–178° C. |
| (666) | 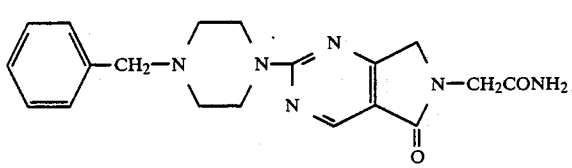 | m.p. 229–232° C. (decomp.) |
| (668) | 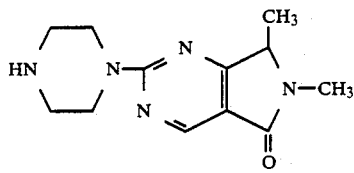 | m.p. 152–154° C. |

| | | |
|---|---|---|
| (670) | 2-Naphthalenesulfonate of (668) | m.p. 180–184° C. |
| (672) | 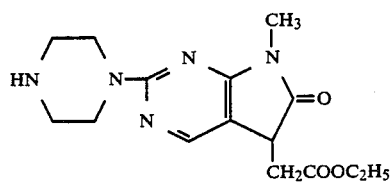 | |
| (674) | 2-Naphthalenesulfonate of (672) | m.p. 70–77° C. |
| (676) | 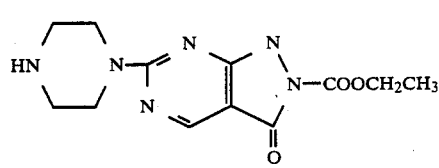 | m.p. 158–163° C. |
| (678) | 2-Naphthalenesulfonate of (676) | m.p. 236–237° C. (decomp.) |
| (680) | 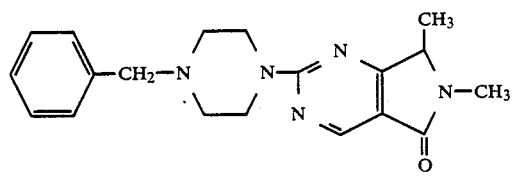 | m.p. 129–132° C. |
| (682) | 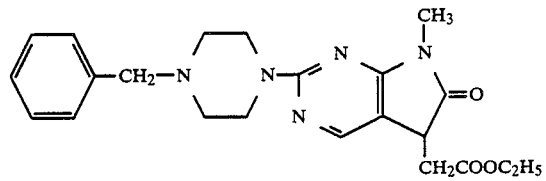 | |
| (684) | 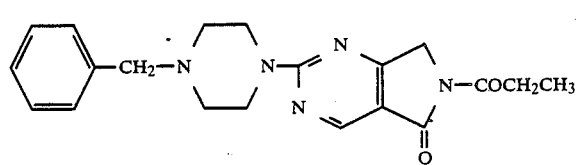 | m.p. 174–177° C. |
Compounds of the following formula (I)-f
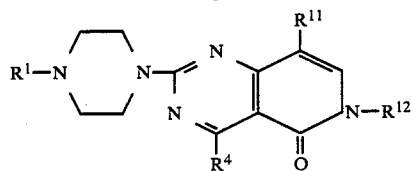  (I)-f
wherein $R^1$, $R^4$, $R^{11}$ and $R^{12}$ are as defined above, and $R^2$ and $R^3$ are bonded to each other to form
the group 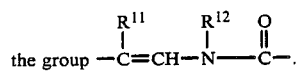.
| | | |
|---|---|---|
| (700) | 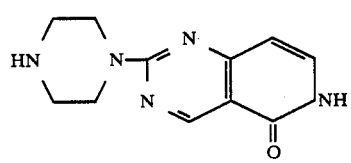 | m.p. 252.8° C. |
| (701) | Hydrochloride of (700) | |

-continued
(702) 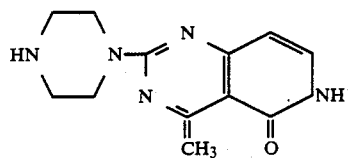
(704) 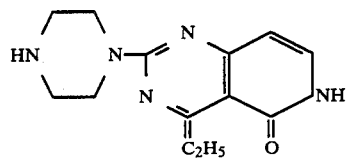
(706) 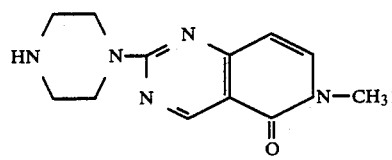  Oil
(707) Hydrochloride of (706)
(708) 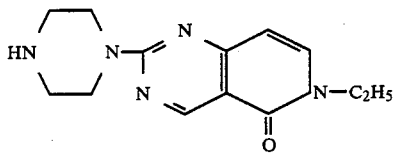  m.p. 149–152° C.
(710) Hydrochloride of (708)  m.p. 227–279° C.
(712) 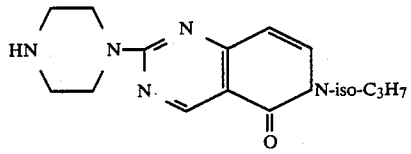  m.p. 161° C.
(713) Hydrochloride of (712)
(714) 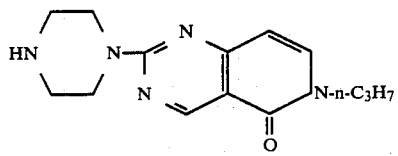  m.p. 143° C.
(715) Hydrochloride of (714)
(716) 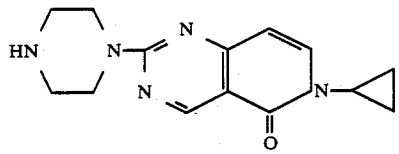
(718) 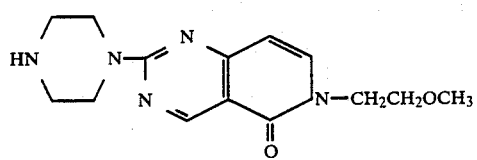

-continued
(720) 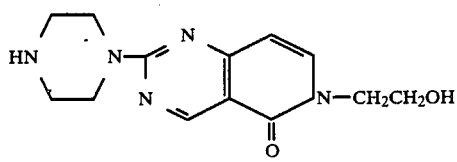
(722) 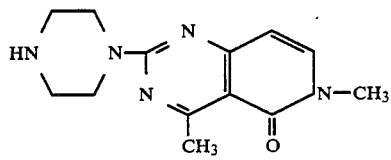
(724) 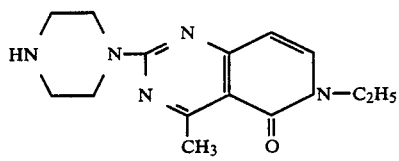
(726) 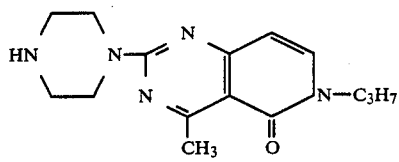
(728) 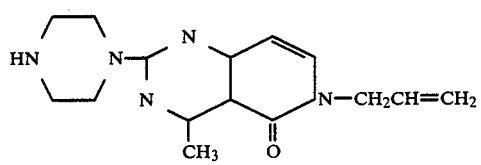
(730) 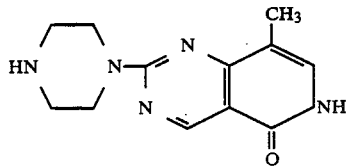
(732) 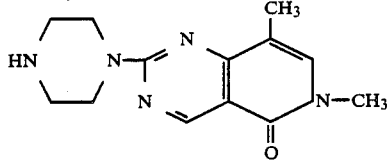
(734) 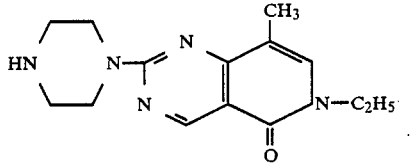  m.p. 170–172° C.
(736) 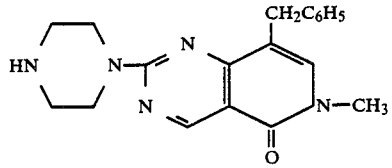

(738) 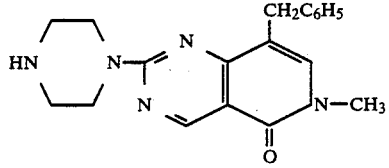
(740) 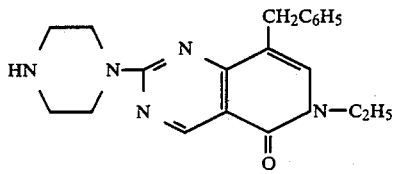   m.p. 231.7° C.
(742) 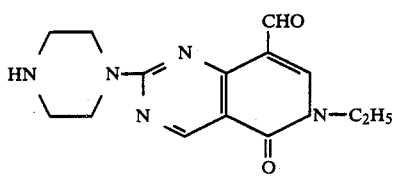   m.p. above 300° C.
(744)   Hydrochloride of (742)   m.p. above 300° C.
(746) 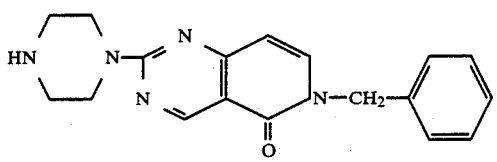
(748)   Hydrochloride of (746)
Compounds of the following formula (I)-g
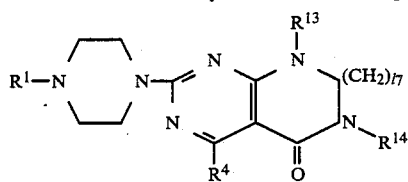   (I)-g
wherein $R^1$, $R^4$, $R^{13}$, $R^{14}$ and $l_7$ are as defined above, and $R^2$ and $R^3$ are bonded to each other to
form the group 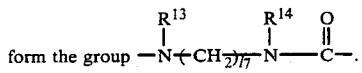.
(800) 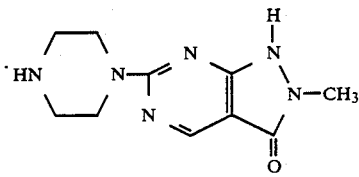
(802)   Hydrochloride of (800)
(804) 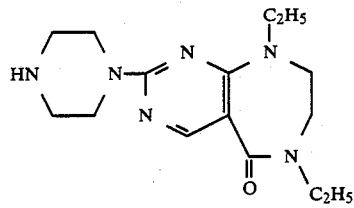

(806) 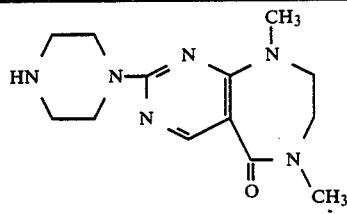
Compounds of the following formula (I)-h    (I)-h
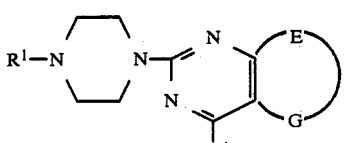
wherein $R^1$, $R^4$ and E-G are as defined above, and $R^2$ and $R^3$ are bonded to each other to form the group E-G
(900) 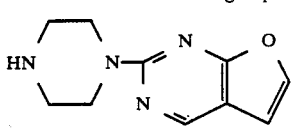    m.p. 74–78° C.
(902) Hydrochloride of (900)    m.p. 294° C. (decomp.)
(904) 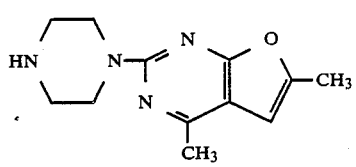    m.p. above 300° C.
(906) Hydrochloride of (904)    m.p. above 300° C.
(908) 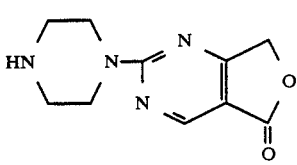    m.p. 159–160° C.
(910) Maleate of (908)    m.p. 183–185° C.
(912) 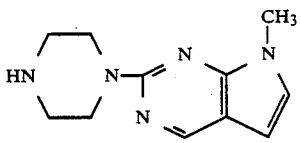    m.p. 63–65° C.
(914) 2-Naphthalenesulfonate of (912)    m.p. 160–162° C.
(916) 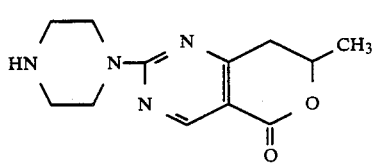
(918) Hydrochloride of (916)    m.p. 274–276° C. (decomp.)
(920) 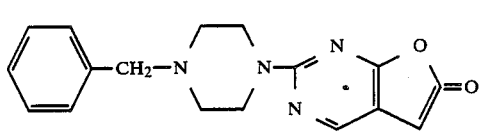
(922) p-Toluenesulfonate of (920)    m.p. 214–218° C. (decomp.)

| | | |
|---|---|---|
| (924) | [structure: benzyl-piperazine-amidine fused with furanone ring] | |
| (926) | [structure: benzyl-piperazine-amidine fused with dihydrofuran] | m.p. 121–123° C. |
| (928) | [structure: benzyl-piperazine-amidine fused with methyl-furan] | m.p. 121–123° C. |
| (930) | [structure: benzyl-piperazine-amidine fused with N-methyl pyrroline] | m.p. 105–107° C. |
| (932) | [structure: benzyl-piperazine-amidine fused with methyl-lactone ring] | |
| (934) | [structure: piperazine-amidine fused with methyl-thiophene-cyclohexane] | |
| (936) | Maleate of (934) | |
| (938) | [structure: piperazine-amidine fused with dimethoxybenzene] | |
| (940) | Hydrochloride of (938) | |
| (942) | [structure: piperazine-amidine fused with benzene] | |
| (944) | [structure: 3,4-dimethoxybenzoyl-piperazine-amidine fused with dimethoxybenzene] | m.p. 188–190° C. |

The compound of formula (I) used as the active ingredient in this invention can be produced by a method known per se, particularly by the methods described in Japanese Laid-Open Patent Publications Nos. 140568/1986, 87627/1986 and 1040568/1986 and by treating the intermediates obtained by these methods known per se (for example, reductive elimination of the protective group). Examples 1A to 48A below describe the production of the compounds in detail.

The compound of formula (I) is usually used in the form of a pharmaceutical composition, and administered through various routes, for example, oral, subcutaneous, intramuscular, intravenous, intrarhinal, skin permeation or intrarectal.

The present invention includes a pharamceutical preparation comprising a pharmaceutically acceptable carrier and the compound of general formula (I) or its pharmaceutically acceptable salt as an active ingredient. The pharmaceutically acceptable salt includes acid addition salts or quaternary ammonium (or amine) salts.

Examples of the pharmaceutically acceptacle salts of the compound (I) include hydrochlorides, hydrobromides, sulfates, bisulfites, phosphates, acidic phosphates, acetates, maleates, fumarates, succinates, lactates, tartrates, benzoates, citrates, gluconates, glucanates, methanesulfonates, p-toluenesulfonates and naphthalenesulfonates which are formed from acids capable of forming pharmaceutically acceptable anion-containing nontoxic acid addition salts, hydrates thereof, and quaternary ammonium (or amine) salts or hydrates thereof. The composition of this invention may be formulated into tablets, capsules, powders, granules, troches, cachet wafer capsules, elixirs, emulsions, solutions, syrups, suspensions, aerosols, ointments, aseptic injectables, molded cataplasmas, tapes, soft and hard gelatin capsules, suppositories, and aseptic packed powders. Examples of the pharmaceutically acceptable carrier include lactose, glucose, sucrose, sorbitol, mannitol, corn starch, crystalline cellulose, gum arabic, calcium phosphate, alginates, calcium silicate, microcrystalline cellulose, polyvinyl pyrrolidone, tragacanth gum, gelatin, syrup, methyl cellulose, carboxymethyl cellulose, methylhydroxybenzoic acid esters, propylhydroxybenzoic acid esters, talc, magnesium stearates, inert polymers, water and mineral oils.

Both solid and liquid compositions may contain the aforesaid fillers, binders, lubricants, wetting agents, disintegrants, emulsifying agents, suspending agents, preservatives, sweetening agents and flavoring agents. The composition of this invention may be formulated such that after administration to a patient, the active compound is released rapidly, continuously or slowly.

In the case of oral administration, the compound of formula (I) is mixed with a carrier or diluent and formed into tablets, capsules, etc. In the case of parenteral administration, the active ingredient is dissolved in a 10% aqueous solution of glucose, isotonic salt water, sterilized water or a like liquid, and enclosed in vials or ampoules for intravenous installation or injection or intramuscular injection. Advantageously, a dissolution aid, a local anesthetic agent, a preservative and a buffer may also be included into the medium. To increase stability, it is possible to lyophilize the present composition after introduction into a vial or ampoule. Another example of parenteral administration is the administration of the pharmaceutical composition through the skin as an ointment or a cataplasm. In this case, a molded cataplasm or a tape is advantageous.

The composition of this invention contains 0.1 to 2000 mg, more generally 0.5 to 1000 mg, of the active component for each unit dosage form.

The compound of formula (I) is effective over a wide dosage range. For example, the amount of the compound administered for one day usually falls within the range of 0.003 mg/kg to 100 mg/kg. The amount of the compound to be actually administered is determined by a physician depending, for example, upon the type of the compound administered, and the age, body weight, reaction, condition, etc. of the patient and the administration route.

The above dosage range, therefore, does not limit the scope of the invention. The suitable number of administrations is 1 to 6, usually 1 to 4, daily.

The compound of formula (I) by itself is an effective therapeutic agent for disorders of the peripheral nervous system and the central nervous system. If required, it may be administered in combination with at least one other equally effective drug. Examples of such an additional drug are gangliosides, mecobalamin and isaxonine.

The formulation of the compounds of formula (I) used in this invention and their biological activities will now be illustrated in more detail by a series of Examples B and C below. These examples, however, do not limit the present invention. The following examples of a composition use one of the compounds described in the specification or another therapeutic compound within the general formula (I) as an active ingredient.

EXAMPLES

Example 1A 2-(4-Benzylpiperazino)-5,6-dihydro-6-oxofuro[2,3-d]pyrimidine (compound No. 920):

(1) A mixture composed of 20 g (56.1 mmoles) of ethyl 2-(4-benzylpiperazino)-4-hydroxypyrimidine-5-acetate (prepared in accordance with Referential Example 70 of Japanese Laid-Open Patent Publication No. 140568/1986), 7.5 g (114 moles) of 85% KOH tablets and 320 ml of ethanol was refluxed for 1 hour. The reaction mixture was concentrated to a solid. Hydrochloric acid and saturated aqueous sodium bicarbonate solution were added to adjust the pH to 4, and the mixture was again concentrated. The resulting crude crystals were recrystallized from water to give 17 g (yield 92%) of 2-(4-benzylpiperazino)-4-hydroxypyrimidine-5-acetic acid as a colorless solid.

$^1$H-NMR spectrum (CDCl$_3$-CD$_3$OD solution, δppm):

2.62 (4H, m), 3.36 (2H, s), 3.65 (6H, m), 7.38 (5H, m), 7.60 (1H, s).

(2) The compound obtained in (1) above (3.28 g; 10 mmoles) was dissolved in 40 ml of chloroform, and 4.2 g (20 mmoles) of trifluoroacetic anhydride was added to the solution. The solution was stirred for 2 hours at room temperature. The reaction mixture was concentrated and then extracted by adding saturated aqueous sodium bicarbonate solution and ethyl acetate. The organic layer was dried and concentrated. The resulting violet solid was slurried with ethyl acetate to give the captioned compound as colorless crystals (1.42 g; yield 46%).

Melting point: 164.5°–166.5° C. (decomp.)

Infrared absorption spectrum (CHCl$_3$ solution, cm$^{-1}$): 1821, 1631, 1559.

$^1$H-NMR spectrum (CDCl$_3$ solution, δppm):

2.52 (4H, m), 3.58 (2H, s), 3.70 (2H, two singlets), 3.86 (4H, m), 7.36 (5H, m), 8.12 (1H, s).

Example 2A 2-(4-Benzylpiperazino)-5,6-dihydro-6-oxofuro[2,3-d]pyrimidine p-toluenesulfonate (compound No. 922):

Ethyl acetate (30 ml) was added to 0.16 g (0.5 mmole) of the compound (No. 920) obtained in Example 1A, and the mixture was heated to form a solution. A solution of 0.086 g (0.5 mmole) of p-toluenesulfonic acid in ethyl acetate (5 ml) was added to the solution. The precipitated crystals were collected by filtration to give 0.23 g (yield 96%) of the captioned compound as crystals.

Melting point: 214°–218° C. (decomp.)

Example 3A 2-(4-Benzylpiperazino)-5,6-dihydro-7-methyl-6-oxo(7H)pyrrolo[2,3-d]pyrimidine 2-naphthalenesulfonate (compound No. 434):

1.29 g (4.0 mmoles) of 2-(4-benzylpiperazino)-5,6-dihydro-7-methyl-6-oxo(7H)pyrrolo[2,3-d]pyrimidine (produced in accordance with Referential Example 54 of Japanese Laid-Open Patent Publication No. 140568/1986) was dissolved in 200 ml of ethanol. A solution of 0.83 g (4.0 mmoles) of 2-naphthalenesulfonic acid in ethanol (20 ml) was added to the solution, and the mixture was stirred at room temperature for 1 hour. The reaction mixture was concentrated to give 2.1 g of the captioned compound as a colorless solid.

Melting point: 74°–82° C.

$^1$H-NMR spectrum (DMSO-$d_6$ solution, $\delta$ppm) 3.12 (3H, s), 3.35 (8H, m), 3.52 (2H, s), 4.32 (2H, bs), 7.52 (5H, m), 7.5–8.3 (8H, m).

Example 4A 2-(4-Acetylpiperazino)-5,6-dihydro-7-methyl-6-oxo(7H)pyrrolo[2,3-d]pyrimidine (compound No. 440):

Acetic anhydride (1.02 g; 10.0 mmoles) was added dropwise to a solution composed of 1.44 g (6.18 mmoles) of 2-piperazino-5,6-dihydro-7-methyl-6-oxo(7H)pyrrolo[2,3-d]pyrimidine (produced in accordance with Referential Example 55 of Japanese Laid-Open Patent Publication No. 140568/1986), 1.01 g of triethylamine and 20 ml of chloroform, and the mixture was stirred at room temperature for 15 minutes. The reaction mixture was concentrated. Ethyl acetate was added to the resulting solid, and it was reslurried at 50° C. After cooling, the slurry was filtered to give 1.02 g (yield 60%) of the captioned compound as crude crystals. Recrystallization from chloroform/ethyl acetate (1/10) gave a pure product.

Melting point: 194°–195° C.

$^1$H-NMR spectrum (CDCl$_3$ solution, $\delta$ppm):
2.16 (3H, s), 3.20 (3H, s), 3.43 (2H, two singlets), 3.5–4.0 (8H, m), 7.92 (1H, s).

Example 5A 5,6-Dihydro-7-methyl-6-oxo-2-piperazino(7H)pyrrolo[2,3-d]pyrimidine phosphate (compound No. 418):

A solution of 0.6 g of phosphoric acid in 10 ml of ethanol was added to a solution of 1.4 g (6.0 mmoles) of 5,6-dihydro-7-methyl-6-oxo-2-piperazino(7H)pyrrolo[2,3-d]pyrimidine (produced in accordance with Referential Example 55 of Japanese Laid-Open Patent Publication No. 140568/1986) in 40 ml of ethanol. The crystals that precipitated were collected by filtration to give 1.5 g (yield 76%) of the desired product.

Melting point: 286°–289° C. (decomp.)

$^1$H-NMR spectrum (DMSO-$d_6$ solution, $\delta$ppm):
3.0 (4H, m), 3.09 (3H, s), 3.49 (2H, s), 3.90 (4H, m), 7.99 (1H, s).

Similarly, the following compounds were produced.

| Compound No. | Yield (%) | Melting point (°C.) | $^1$H—NMR spectrum (DMSO—$d_6$ solution, $\delta$ ppm) |
|---|---|---|---|
| 410 | 81 | 254–256 | 3.10 (7H, m), 3.52 (2H, s), 3.92 (4H, m), 8.03 (1H, s). |
| 412 | 80 | 244–225 | 2.30 (3H, s), 3.08 (3H, s), 3.18 (4H, m), 3.50 (2H, s), 3.95 (4H, m), 7.12 (2H, m), 7.52 (2H, m), 8.02 (1H, s). |
| 414 | 95 | 187–188 | 2.54 (4H, s), 3.10 (7H, m), 3.50 (2H, s), 3.92 (4H, m), 8.02 (1H, s). |
| 416 | 78 | 230–232 (decomp.) | 3.08 (7H, m), 3.48 (2H, s), 3.88 (4H, m), 3.94 (2H, s), 7.99 (1H, s). |

Example 6A 2-(4-Benzylpiperazino)-6-(1-methylpropyl)-5-oxo-5,6-dihydro(7H)pyrrolo[3,4-d]pyrimidine (compound No. 656):

3.0 g (8 mmoles) of ethyl 2-(4-benzylpiperazino)-4-chloromethylpyrimidine-5-acetate (produced in accordance with Referential Example 41 of Japanese Laid-Open Patent Publication No. 140568/1986) was dissolved in 30 ml of n-butanol, and 5.9 g (80 mmoles) of 1-methylpropylamine was added. The mixture was stirred at 60° C. for 3 hours and then at 130° C. for 4 hours. After the reaction, the solvent was evaporated, and the residue was dissolved in ethyl acetate and water. The aqueous layer was separated, and the ethyl acetate layer was washed with saturated aqueous sodium bicarbonate solution, and dried over anhydrous magnesium sulfate. Ethyl acetate was evaporated under reduced pressure, and the residue was purified by silica gel column chromatography using ethyl acetate to give 0.7 g (yield 23%) of the desired product.

Melting point: 131°–134° C.

$^1$H-NMR spectrum (CDCl$_3$ solution, $\delta$ppm):
0.88 (3H, t, J=7 Hz), 1.24 (3H, d, J=7 Hz), 1.52 (2H, m), 2.52 (4H, m), 3.58 (2H, s), 3.96 (4H, m), 4.12 (2H, s), 4.30 (1H, m), 7.36 (5H, m), 8.68 (1H, s).

Similarly, the following compounds were produced.

| Compound No. | Yield (%) | Melting point (°C.) | $^1$H—NMR spectrum (CDCl$_3$ solution, $\delta$ ppm) |
|---|---|---|---|
| 658 | 29 | 132–134 | 0.9–1.6 (10H), 2.52 (4H, m), 3.56 (2H, s), 3.94 (4H, m), 4.12 (2H, s), 4.48 (1H, m), 7.34 (5H, m), 8.66 (1H, s). |
| 660 | 20 | 179–182 | 1.54 (9H, s), 2.54 (4H, m), 3.58 (2H, s), 3.97 (4H, m), 4.24 (2H, s), 7.36 (5H, m), 8.86 (1H, s). |
| 662 | 19 | 145–147 | 1.30 (3H, t, J = 7 Hz,), 2.53 (4H, m), 3.58 (2H, s), 3.97 (4H, m), 4.23 (2H, q, J = 7 Hz), 4.33 (2H, s), 4.36 (2H, s), 7.36 (5H, m), 8.70 (1H, s). |

Example 7A 2-(4-Benzylpiperazino)-6-acetyl-5-oxo-5,6-dihydro(7H)pyrrolo[3,4-d]pyrimidine (compound No. 664):

0.3 g (25 mmoles) of 60% NaH was added to a mixture of 2.0 g (6.5 mmoles) of 2-(4-benzylpiperazino)-5-oxo-5,6-dihydro(7H)pyrrolo[3,4-d]pyrimidine (produced in accordance with Referential Example 42 of Japanese Laid-Open Patent Publication No. 140568/1986) and 60 ml of tetrahydrofuran, and the mixture was stirred at 20° C. for 10 minutes. Then, 2 ml of acetyl bromide was added, and the mixture was stirred for 1 hour. The reaction mixture was poured into a saturated aqueous sodium bicarbonate solution and extracted with $CH_2Cl_2$, and the solvent was evaporated. The residue was purified by silica gel column chromatography ($CH_2Cl_2$:MeOH=95:5) to give 1.0 g (yield 44%) of the desired product.

Melting point: 176°–178° C.

$^1$H-NMR spectrum ($CDCl_3$ solution, δppm): 2.54 (4H, m), 2.65 (3H, s), 3.58 (2H, s), 4.02 (4H, m), 4.60 (2H, s), 7.36 (5H, m), 8.74 (1H, s).

Example 8A 2-(4-Benzylpiperazino)-6-carbamoylmethyl-5-oxo-5,6-dihydro(7H)pyrrolo[3,4-d]pyrimidine (compound No. 666):

3.6 g (59 mmoles) of 28% aqueous ammonia and 4 ml of ethanol were added to 1.0 g (2.5 mmoles) of 2-(4-benzylpiperazino)-6-ethoxycarbonylmethyl-5-oxo-5,6-dihydro(7H)pyrrolo[3,4-d]pyrimidine (compound No. 662 in Example 6A), and the mixture was stirred overnight at room temperature. The reaction mixture was concentrated, and extracted with water and $CH_2Cl_2$. The aqueous layer was separated, and the $CH_2Cl_2$ layer was dried over anhydrous $MgSO_4$. $CH_2Cl_2$ was evporated under reduced pressure, and the residue was washed with ethyl acetate to give 0.5 g (yield 57%) of the desired compound.

Melting point: 229°–232° C. (decomp.)

$^1$H-NMR spectrum ($CDCl_3$-DMSO-$d_6$ solution, δppm): 2.52 (4H, m), 3.58 (2H, s), 3.96 (4H, m), 4.22 (2H, s), 4.39 (2H, s), 7.36 (5H, m), 8.65 (1H, s).

Example 9A

6-Acetyl-2-piperazino-5-oxo-5,6-dihydro(7H)-pyrrolo[3,4-d]pyrimidine (compound No. 648):

A mixture composed of 0.8 g (2.4 mmoles) of 6-acetyl-2-(4-benzylpiperazino)-5-oxo-5,6-dihydro(7H)pyrrolo[3,4-d]pyrimidine (compound No. 664 of Example 7A), 0.2 g of 10% Pd-C, and 40 ml of ethanol was stirred for 4 hours at 70° C. in a hydrogen atmosphere. After the reaction, Pd-C was separated by filtration, and ethanol was evaporated under reduced pressure to give 0.56 g (yield 90%) of the desired product.

Melting point: 164°–167° C.

$^1$H-NMR spectrum ($CDCl_3$ solution, δppm): 2.66 (3H, s), 2.96 (4H, m), 3.98 (4H, m), 4.62 (2H, s), 8.75 (1H, s).

Similarly, the following compounds were produced.

| Compound No. | Yield (%) | Melting point (°C.) | $^1$H—NMR spectrum ($CDCl_3$ solution, δ ppm) |
|---|---|---|---|
| 636 | 92 | 110–115 | 0.90 (3H, t, J = 7 Hz), 1.24 (3H, d, J = 7 Hz), 1.56 (2H, m), 2.94 (4H, m), 3.94 (4H, m), 4.14 (2H, s), 4.35 (1H, m), 8.68 (1H, s). |
| 644 | 99 | 106–112 | 0.8–1.6 (10H, m), 2.94 (4H, m), 3.92 (4H, m), 4.14 (2H, s), 4.46 (1H, m), 8.68 (1H, s). |
| 640 | 99 | 162–164 | 1.54 (9H, s), 2.92 (4H, m), 3.90 (4H, m), 4.28 (2H, s), 8.62 (1H, s). |
| 652 | 87 | 239–241 (decomp.) | 2.94 (4H, m), 3.96 (4H, m), 4.22 (2H, s), 4.43 (2H, s), 8.70 (1H, s).* |

*$CDCl_3$—$CD_3OD$ solution.

Example 10A

6-Acetyl-2-piperazino-5-oxo-5,6-dihydro(7H)pyrrolo[3,4-d]pyrimidine naphthalene-2-sulfonate (compound No. 650):

A solution of 0.17 g of naphthalene-2-sulfonic acid monohydrate in 10 ml of ethanol was added to a solution of 0.20 g (0.77 mmole) of 6-acetyl-2-piperazino-5-oxo-5,6-dihydro(7H)pyrrolo[3,4-d]pyrimidine (compound No. 648 of Example 9A) in 25 ml of 20% methylene chloride/ethanol. The crystals that precipitated were collected by filtration to give 0.24 g (yield 67%) of the desired product.

Melting point: 260°–263° C. (decomp.)

$^1$H-NMR spectrum (DMSO-$d_6$ solution, δppm): 2.68 (3H, s), 3.42 (4H, m), 4.26 (4H, m), 4.78 (2H, s), 7.6–8.3 (7H), 9.03 (1H, s).

Similarly, the following compounds were produced.

| Compound No. | Yield (%) | Melting point (°C.) | $^1$H—NMR spectrum (DMSO—$d_6$ solution, δ ppm) |
|---|---|---|---|
| 638 | 68 | 151–152 | 0.90 (3H, t, J = 7 Hz), 1.20 (3H, d, J = 7 Hz), 1.58 (2H, m), 3.35 (4H, m), 4.08 (4H, m), 4.32 (2H, s), 6.06 (2H, s), 8.72 (1H, s). |
| 646 | 68 | 134–136 | 0.8–1.6 (10H), 3.24 (4H, m), 4.08 (4H, m), 4.30 (3H, m), 6.05 (2H, s), 8.70 (1H, s). |
| 642 | 76 | 202–203 | 1.48 (9H, s), 3.22 (4H, m), 4.07 (4H, m), 4.52 (2H, s), 6.05 (2H, s), 8.66 (1H, s). |
| 654 | 72 | 276–277 (decomp.) | 3.30 (4H, m), 4.10 (6H, m), 4.44 (2H, s), 7.2–8.2 (7H), 8.76 (1H, s). |

Example 11A 2-(4-Benzylpiperazino)-5,6-dihydro-5,7-dimethyl-6-oxo(7H)pyrrolo[2,3-d]pyrimidine (compound No. 456):

(1) A solution of 2.16 g (10 mmoles) of ethyl 2-formyl-3-methylsuccinate [Zhur. Obshche i Khim., 30, 2250 (1960)] was added to a mixture of 2.67 g (10 mmoles) of 1-amidino-4-benzylpiperazine sulfate, 1.12 g (10 mmoles) of tert-$C_4H_9OK$ and 12 ml of tert-$C_4O_9OH$. The mixture was then refluxed for 6 hours. The reaction mixture was cooled, and extracted by adding water and $CHCl_3$. The $CHCl_3$ layer was dried over anhydrous $MgSO_4$, and the solvent was evaporated under reduced pressure. The residue was purified by silica gel column chromatography ($CH_2Cl_2$:$CH_3OH$=95:5) to give 0.68 g (yield 23%) of 2-(4-benzylpiperazino)-5-(1-ethoxycarbonylethyl)-4-hydroxypyrimidine.

Melting point: 145°–148° C.

$^1$H-NMR spectrum ($CDCl_3$ solution, δppm): 1.17 (3H, t, J=7 Hz), 1.39 (3H, d, J=7 Hz), 2.56 (4H, m), 3.56 (3H, m), 3.74 (4H, m), 4.04 (2H, q, J=7 Hz), 7.35 (5H, m), 7.68 (1H, s).

(2) A solution of 4.6 g (12.4 mmoles) of the compound obtained as in (1) above and 35 g of phosphorus oxychloride was refluxed for 2 hours. The reaction solution was poured into water, and extracted with ether. The ether layer was dried over anhydrous $MgSO_4$, and the solvent was evaporated under reduced pressure to give 3.2 g (yield 67%) of 2-(4-benzylpiperazino)-5-(1-ethoxycarbonylethyl)-4-chloropyrimidine as an oil.

¹H-NMR spectrum (CDCl₃ solution, δppm): 1.24 (3H, t, J=7 Hz), 1.48 (3H, d, J=7 Hz), 2.50 (4H, m), 3.56 (2H, s), 3.82 (5H, m), 4.16 (2H, q, J=7 Hz), 7.34 (5H, m), 8.18 (1H, s).

(3) A mixture of 3.2 g (8.2 mmoles) of the compound obtained in (2) above, 1.3 g (16.5 mmoles) of a methanol solution of 40% CH₃NH₂ and 7 ml of ethanol was put in a pressure vessel, and heated at 120° C. for 6 hours. The solvent was removed under reduced pressure. Water was added, and the mixture was extracted with chloroform. The chloroform layer was dried over anhydrous MgSO₄, and the solvent was evaporated under reduced pressure. The residue was purified by silica gel column chromatography (ethyl acetate) to give 2.1 g (yield 75%) of the captioned compound.

Melting point: 142°-146° C.

¹H-NMR spectrum (CDCl₃ solution, δ ppm): 1.44 (3H, d, J=7 Hz), 2.52 (4H, m), 3.19 (3H, s), 3.41 (1H, q, J=7 Hz), 3.57 (2H, s), 3.87 (4H, m), 7.35 (5H, m), 7.90 (1H, s).

Example 12A 5,6-Dihydro-5,7-dimethyl-6-oxo-2-piperazino(7H-)pyrrolo[2,3-d]pyrimidine (compound No. 444):

1.9 g (5.6 mmoles) of 2-(4-benzylpiperazino)-5,6-dihydro-5,7-dimethyl-6-oxo-(7H)pyrrolo[2,3-d]pyrimidine (compound No. 456 of Example 11A) and 0.2 g of 10% Pd-C were dissolved in 70 ml of ethanol, and the solution was stirred for 4 hours at 70° in a hydrogen atmosphere. After the reaction, Pd-C was separated by filtration. Ethanol was evaporated under reduced pressure to give 1.26 g (yield 90%) of the desired product.

Melting point: 167.2°-169.2° C.

¹H-NMR spectrum (CDCl₃ solution, δ ppm): 1.44 (3H, d, J=7 Hz), 2.94 (4H, m), 3.22 (3H, s), 3.42 (1H, q, J=7 Hz), 3.82 (4H, m), 7.92 (1H, s).

Example 13A 5,6-Dihydro-5,7-dimethyl-6-oxo-2-piperazino(7H-)pyrrolo[2,3-d]pyrimidine maleate (compound No. 446):

A solution of 0.14 g (1.2 mmoles) of maleic acid in 6 ml of ethanol was added to a solution of 0.29 g (1.2 mmoles) of 5,6-dihydro-5,7-dimethyl-6-oxo-2-piperazino(7H)pyrrolo[2,3-d]pyrimidine (compound No. 444 of Example 12A) in 20 ml of ethanol. The crystals that precipitated were collected by filtration to give 0.26 g (yield 59%) of the desired product.

Melting point: 181°-183° C.

¹H-NMR spectrum (DMSO-d₆ solution, δ ppm): 1.34 (3H, d, J=7 Hz), 3.10 (3H, s), 3.20 (4H, m), 3.55 (1H, q, J=7 Hz), 3.96 (4H, m), 6.05 (2H, s), 8.10 (1H, s).

Example 14A 2-(4-Benzylpiperazino)-5,6-dihydro-6-oxo-5,5,7-trimethyl(7H)pyrrolo[2,3-d]pyrimidine (compound No. 458):

4.0 g (12.4 ml) of 2-(4-benzylpiperazino]-5,6-dihydro-7-methyl-6-oxo(7H)pyrrolo[2,3-d]pyrimidine (produced in accordance with Referential Example 54 of Japanese Laid-Open Patent Publication No. 140568/1986) was dissolved in 200 ml of tetrahydrofuran, and 2.5 g (62.5 mmoles) of 60% NaH was added at 20° C., and the mixture was stirred for 10 minutes. Thereafter, 4 ml of methyl iodide was added and the mixture was stirred for 1 hour. The reaction solution was poured into water and extracted with CH₂Cl₂. The solvent was evaporated, and the residue was purified by silica gel column chromatography to give 1.3 g (yield 30%) of the desired product.

Melting point: 76°-79° C.

¹H-NMR spectrum CDCl₃ solution, δ ppm): 1.36 (6H, s), 2.50 (4H, m), 3.19 (3H, s), 3.54 (2H, s), 3.86 (4H, m), 7.34 (5H, m), 7.88 (1H, s).

In the same way as above, compound No. 682 was synthesized except that ethyl bromoacetate was used instead of methyl iodide; compound No. 684 was synthesized except that 2-(4-benzylpyrazino)-5-oxo-5,6-dihydro(7H)pyrrolo[3,4-d]pyrimidine (produced in accordance with Referential Example 42 of Japanese Laid-Open Patent Publication No. 140568/1986) and propionyl chloride were used instead of 2-(4-benzyl-piperazino)-5,6-dihydro-7-methyl-6-oxo(7H)pyrrolo[2,3-d]pyrimidine and methyl iodide; and compound No. 680 was synthesized except that 2-(4-benzylpiperazino)-5,6-dihydro-6-methyl-5-oxo(7H)pyrrolo[3,4-d]pyrimidine (produced in accordance with Referential Example 44 of Japanese Laid-Open Patent Publication No. 140568/1986) was used,

| Compound No. | Yield (%) | Melting point (°C.) | ¹H—NMR spectrum (CDCl₃ solution, δ ppm) |
|---|---|---|---|
| 682 | 26 | Not measured | 1.24 (3H, t, J = 7 Hz), 2.52 (4H, m), 2.75 (1H, d, J = 8 Hz), 2.98 (1H, d, J = 4 Hz), 3.22 (3H, s), 3.58 (2H, s), 3.72 (1H, dd, J = 4 and 8 Hz), 3.87 (4H, m), 4.16 (2H, q, J = 7 Hz), 7.36 (5H, m), 7.96 (1H, s). |
| 684 | 44 | 174–177 | 1.24 (3H, t, J = 7 Hz), 2.54 (4H, m), 3.08 (2H, q, J = 7 Hz), 3.59 (2H, s), 4.02 (4H, m), 4.62 (2H, s), 7.36 (5H, m), 8.74 (1H, s). |
| 680 | 25 | 129–132 | 1.46 (3H, d, J = 7 Hz), 2.52 (4H, m), 3.05 (3H, s), 3.56 (2H, s), 3.56 (2H, s), 3.96 (4H, m), 4.22 (1H, q, J = 7 Hz), 7.34 (5H, m), 8.66 (1H, s). |

Example 15A 5,6-Dihydro-6-oxo-2-piperazino-5,5,7-trimethyl(7H-)pyrrolo[2,3-d]pyrimidine (compound No. 448):

A mixture composed of 1.1 g (3.1 mmoles) of 2-(4-benzylpiperazino)-5,6-dihydro-6-oxo-5,5,7-trimethyl(7H)pyrrolo[2,3-d]pyrimidine (compound No. 458 of Example 14A), 0.1 g of 10% Pd-C, and 40 ml of ethanol was stirred for 4 hours at 70° C. in a hydrogen atmosphere. After cooling, Pd-C was separated by filtration. Ethanol was evaporated under reduced pressure to give 0.76 g (yield 94%) of the desired product.

Melting point: 113°-116° C.

¹H-NMR (CDCl₃ solution, δ ppm): 1.38 (6H, s), 2.94 (4H, m), 3.22 (3H, s), 3.83 (4H, m), 7.90 (1H, s).

The following compounds were produced in the same way as above except that compounds Nos. 682, 684 and 680 produced in Example 14A were used respectively instead of 2-(4-benzylpiperazino)-5,6-dihydro-6-oxo-5,5,7-trimethyl(7H)pyrrolo[2,3-d]pyrimidine.

| Compound No. | Yield (%) | Melting point (°C.) | ¹H—NMR spectrum (CDCl₃ solution, δ ppm) |
|---|---|---|---|
| 672 | 98 | Not measured | 1.25 (3H, t, J = 7 Hz), 2.80 (1H, d, J = 8 Hz), 3.00 (1H, |

-continued

| Compound No. | Yield (%) | Melting point (°C.) | $^1$H—NMR spectrum (CDCl$_3$ solution, δ ppm) |
|---|---|---|---|
| | | | d, J = 4 Hz), 3.24 (3H, s), 3.29 (4H, m), 3.74 (1H, dd, J = 4.8 Hz), 4.20 (6H, m), 7.99 (1H, s). |
| 676 | 95 | 158–163 | 1.24 (3H, t, J = 7 Hz), 2.96 (4H, m), 3.08 (2H, q, J = 7 Hz), 3.98 (4H, m), 4.63 (2H, s), 8.75 (1H, s). |
| 668 | 92 | 152–154 | 1.48 (3H, d, J = 7 Hz), 2.96 (4H, m), 3.08 (3H, s), 3.94 (4H, m), 4.23 (1H, q, J = 7 Hz), 8.68 (1H, s). |

Example 16A 5,6-Dihydro-6-oxo-2-piperazino-5,5,7-trimethyl(7H)pyrrolo[2,3-d]pyrimidine naphthalene-2-sulfonate (compound No. 450):

A solution of 0.17 g (0.77 mmole) of naphthalene-2-sulfonic acid monohydrate in 10 ml of ethanol was added to a solution of 0.20 g (0.77 mmole) of 5,6-dihydro-6-oxo-2-piperazino-5,5,7-trimethyl(7H)pyrrolo[2,3-d]pyrimidine (compound No. 448 of Example 15A) in 10 ml of ethanol, and the mixture was stirred at room temperature for 1 hour. The solvent was evaporated under reduced pressure, and the residue was washed with ether to give 0.2 g (yield 81%) of the desired product.

Melting point: 211°–212° C.

$^1$H-NMR spectrum (CDCl$_3$ solution, δ ppm): 1.36 (6H, s), 3.15 (3H, s), 3.36 (4H, m), 4.15 (4H, m), 7.55 (2H, m), 7.90 (5H, m), 8.44 (1H, s).

The following compounds were produced in the same way as above except that compounds Nos. 672, 676 and 668 produced in Example 15A were used respectively instead of 5,6-dihydro-6-oxo-2-piperazino-5,5,7-trimethyl(7H)pyrrolo[2,3-d]pyrimidine.

| Compound No. | Yield (%) | Melting point (°C.) | $^1$H—NMR spectrum (CDCl$_3$ solution, δ ppm) |
|---|---|---|---|
| 674 | 80 | 70–77 | 1.16 (3H, t, J = 7 Hz), 3.18 (3H, s), 3.28 (6H, m), 4.08 (7H, m), 7.5–8.2 (8H). |
| 678 | 77 | 236–237 (decomp.) | 1.12 (3H, d, J = 7 Hz), 2.97 (2H, q, J = 7 Hz), 3.32 (4H, m), 4.13 (4H, m), 4.66 (2H, s), 7.5–8.2 (7H), 8.89 (1H, s). |
| 670 | 87 | 180–184 | *1.43 (3H, d, J = 7 Hz), 3.06 (3H, s), 3.36 (4H, m), 4.20 (5H, m), 6.75–7.92 (6H), 8.43 (1H, s), 8.66 (1H, s). |

*Measured in CDCl$_3$ solution.

Example 17A 5,6-Dihydro-7-methyl-2[4-(3,4-methylenedioxyphenylmethyl)piperazino]-6-oxo(7H)pyrrolo[2,3-d]pyrimidine (compound No. 436):

A solution consisting of 2.5 g (16.4 mmoles) of piperonyl alcohol, 2.3 g (19.3 mmoles) of SOCl$_2$ and 100 ml of CH$_2$Cl$_2$ was stirred for 1 hour. Then, 3.8 g (16.3 mmoles) of 5,6-dihydro-7-methyl-6-oxo(7H)pyrrolo[2,3-d]pyrimidine (produced in accordance with Referential Example 55 of Japanese Laid-Open Patent Publication No. 140568/1986) and 2.5 g of triethylamine were added, and the mixture was stirred for 30 minutes and then refluxed for 2 hours. The reaction solution was poured into water, and extracted with CH$_2$Cl$_2$. The extract was dried over anhydrous MgSO$_4$, and concentrated under reduced pressure. The residue was purified by silica gel column chromatography to give 0.5 g (yield 8%) of the desired product.

Melting point: 122°–124° C.

$^1$H-NMR spectrum (CDCl$_3$ solution, δ ppm): 2.47 (4H, m), 3.14 (3H, s), 3.25 (2H, s), 3.43 (2H, s), 3.82 (4H, m), 5.91 (2H, s), 6.47 (2H, s), 6.87 (1H, s), 7.86 (1H, s).

Example 18A 5,6-Dihydro-7-methyl-2[4-(3,4-methylenedioxyphenylmethyl)piperazino]-6-oxo(7H)pyrrolo[2,3-d]pyrimidine naphthalene-2-sulfonate (compound No. 438):

A solution consisting of 1.0 g (2.7 mmoles) of 5,6-dihydro-7-methyl-2[4-(3,4-methylenedioxyphenylmethyl)piperazino]-6-oxo(7H)pyrrolo[2,3-d]pyrimidine (compound No. 436 of Example 17A), 0.6 g (2.7 mmoles) of naphthalene-2-sulfonic acid monohydrate, 50 ml of CH$_2$Cl$_2$ and 50 ml of ethanol was stirred at room temperature for 1 hour. The solvent was evaporated under reduced pressure, and the residue was washed with ethanol to give 1.4 g (yield 90%) of the desired product.

Melting point: 234°–239° C. (decomp.)

$^1$H-NMR spectrum (DMSO-d$_6$-CDCl$_3$ solution, δ ppm): 3.12 (3H, s), 3.36 (8H, m), 3.48 (2H, s), 4.32 (2H, s), 6.05 (2H, s), 6.95 (2H, m), 7.12 (1H, s), 7.52 (2H, m), 7.90 (5H, m), 8.25 (1H, s).

Example 19A 2-(4-Ethoxycarbonylpiperazino)-5,6-dihydro-7-methyl-6-oxo(7H)pyrrolo[2,3-pyrimidine (compound No. 442):

Ethyl chloroformate (2.0 g; 18.4 mmoles) was added to a mixture composed of 2.0 g (6.2 mmoles) of 2-(4-benzylpiperazino)-5,6-dihydro-7-methyl-6-oxo(7H)pyrrolo[2,3-d]pyrimidine (produced in accordance with Referential Example 54 of Japanese Laid-Open Patent Publication No. 140568/1986), 0.3 g (6.8 mmoles) of 60% NaH and 60 ml of tetrahydrofuran, and the mixture was stirred for 2 hours. The reaction mixture was poured into water and extracted with CH$_2$Cl$_2$. The organic layer was dried over anhydrous MgSO$_4$, and the solvent was evaporated. The residue was purified by silica gel column chromatography to give 0.5 g (yield 26%) of the desired product.

Melting point: 170°–171° C.

$^1$H-NMR spectrum (CDCl$_3$ solution, δ ppm): 1.30 (3H, t, J=7 Hz), 3.23 (3H, s), 3.45 (2H, s), 3.56 (4H, m), 3.84 (4H, m), 4.20 (2H, q, J=7 Hz), 7.94 (1H, s).

Example 20A 2-(4-Benzylpiperazino)-5,6-dihydro-7-(2-methoxyethyl)-6-oxo(7H)pyrrolo[2,3-d]pyrimidine (compound No. 460):

Ethanol (200 ml) and 12.02 g (0.16 mole) of methoxyethylamine were added to 30.0 g (0.08 mole) of ethyl 2-(4-benzylpiperazino)-4-chloropyrimidine-5-acetate (produced in accordance witth Referential Example 71 of Japanese Laid-Open Patent Publication No. 140568/1986), and the mixture was heated at 150° C. for 7 hours in an autoclave. Ethanol was evaporated under reduced pressure, and the residue was purified by silica gel column chromatography to give 19.1 g (yield 65%) of the captioned compound.

$^1$H-NMR spectrum (CDCl$_3$ solution, δ ppm): 2.51 (4H, m), 3.38 (3H, s), 3.44 (2H, s), 3.57 (2H, s), 3.83 (8H, m), 7.36 (5H, s), 7.92 (1H, s).

Example 21A 5,6-Dihydro-7-(2-methoxyethyl)-6-oxo-2-piperazino(7H)pyrrolo[2,3-d]pyrimidine (compound No. 426):

13.0 g (35.4 mmoles) of 2-(4-benzylpiperazino)-5,6-dihydro-7-(2-methoxyethyl)-6-oxo(7H)pyrrolo[2,3-d]pyrimidine (compound No. 460 of Example 20A) was dissolved in 180 ml of ethanol, and hydrogenated in the presence of 1.3 g of 10% Pd-C at 70° C. under atmospheric pressure for 1.5 hours. The catalyst was separated by filtration, and ethanol was evaporated under reduced pressure to give 9.82 g (yield about 100%) of the captioned compound.

$^1$H-NMR spectrum (CDCl$_3$ solution, δ ppm): 2.92 (4H, m), 3.38 (3H, s), 3.44 (2H, s), 3.80 (8H, m), 7.92 (1H, s).

Example 22A 5,6-Dihydro-7-(2-methoxyethyl)-6-oxo-2-piperazino(7H)pyrrolo[2,3-d]pyrimidine maleate (compound No. 430):

A solution of 1.3 l g (11 mmoles) of maleic acid in 30 ml of ethanol was added to a solution of 3.0 g (11 mmoles) of 5,6-dihydro-7-(2-methoxyethyl)-6-oxo-2-pipierazino(7H)pyrrolo[2,3-d]pyrimidine (compound No. 426 of Example 21A) in 100 ml of ethanol. The mixture was stirred for 1 hour. The crystals that precipitated were collected by filtration to give 3.3 g (yield 76%) of the desired product.

Melting point: 158°–160° C.

$^1$H-NMR spectrum (DMSO-d$_6$ solution, δ ppm): 3.2–3.8 (13H), 3.95 (4H, m), 6.06 (2H, s), 8.06 (1H, s).

Example 23A 2-(4-Benzylpiperazino)-5,7-dihydro-5-oxofuro[3,4-d]pyrimidine (compound No. 924):

(1) Ethanol (80 ml) and 2.64 g (40.0 mmoles) of 85% potassium hydroxide were added to 5.0 g (13.3 mmoles) of ethyl 2-(4-benzylpiperazino)-4-chloromethylpyrimidine-5-carboxylate (produced in accordance with Referential Example 41 of Japanese Laid-Open Patent Publication No. 140568/1986), and the mixture was refluxed for 30 minutes. Ethanol was evaporated under reduced pressure. The residue was dissolved in water, and adjusted to pH about 4 with concentrated hydrochloric acid. The crystals that formed were collected by filtration, and washed with acetone to give 1.93 g (yield 44%) of 2-(4-benzylpiperazino)-4-hydroxymethylpyrimidine-5-carboxylic acid as crystals.

Melting point: 252°–253° C. (decomp.)

$^1$H-NMR spectrum (DMSO-d$_6$ solution, δ ppm): 3.16 (4H, m), 4.00 (6H, m), 4.80 (2H, s), 7.54 (5H, m), 8.79 (1H, s).

(2) Benzene (50 ml), 0.15 g (1.48 mmoles) of acetic anhydride and 0.12 g (1.46 mmoles) of sodium acetate were added to 0.40 g (1.22 mmoles) of the carboxylic acid obtained in (1) above. The mixture was refluxed for 10.5 hours. A 10% aqueous solution of sodium carbonate was added, and the mixture was extracted with ethyl acetate. The ethyl acetate layer was dried and concentrated. The residue was purified by silica gel column chromatography to give 0.15 g (yield 40%) of the captioned compound.

$^1$H-NMR spectrum (CDCl$_3$ solution, δ ppm): 2.54 (4H, m), 3.58 (2H, s), 4.00 (4H, m), 5.04 (2H, s), 7.36 (5H, s), 8.75 (1H, s).

Example 24A 5,7-Dihydro-5-oxo-2-piperazinofuro[3,4-d]pyrimidine (compound No. 908):

A mixture composed of 1.5 g (4.8 mmoles) of 2-(4-benzylpiperazino)-5,7-dihydro-5-oxofuro[3,4-d]pyrimidine (compound No. 924 of Example 23A), 0.2 g of 10% Pd-C and 60 ml of ethanol was stirred at 70° C. for 4 hours in a hydrogen atmosphere. After the reaction, Pd-C was separated by filtration, and ethanol was evaporated under reduced pressure to give 1.0 g (yield 94%) of the desired product.

Melting point: 159°–160° C.

$^1$H-NMR spectrum (CDCl$_3$ solution, δ ppm): 2.05 (1H, s), 2.95 (4H, m), 3.97 (4H, m), 3.97 (4H, m), 5.03 (2H, s), 8.74 (1H, s).

Example 25A 5,7-Dihydro-5-oxo-2-piperazinofuro[3,4-d]pyrimidine maleate (compound No. 910):

A solution of 0.12 g (1.0 mmole) of maleic acid in 15 ml of ethanol was added to a solution of 0.22 g (1.0 mmole) of 5,7-dihydro-5-oxo-2-piperazinofuro[3,4-d]pyrimidine (compound No. 908 of Example 24A) in 30 ml of ethanol. The mixture was stirred at room temperature for 1 hour. The crystals that precipitated were collected by filtration to give 0.20 g (yield 60%) of the desired product.

Melting point: 183°–185° C.

$^1$H-NMR spectrum (DMSO-d$_6$ solution, δ ppm): 3.28 (4H, m), 4.12 (4H, m), 5.25 (2H, s), 6.03 (2H, s), 8.92 (1H, s).

Example 26A 2-(4-Benzylpiperazino)-6,7-dihydro(5H)cyclopentapyrimidine (compound No. 208):

To a solution of 6.55 g (0.121 mole) of sodium methoxide in 500 ml of ethanol was added 32.43 g (0.121 mole) of 1-amidino-4-benzylpiperazine sulfate. A solution of 13.6 g (0.121 mole) of 2-hydroxymethylenecyclopentanone [synthesized by the method of W. T. Caldwell et al., J. Am. Chem. Soc., 63, 2188 (1941)] in 90 ml of ethanol was added dropwise to the resulting suspension over 1 hour. After the addition, the mixture was refluxed for 8 hours. Ethanol was evaporated, and the residue was purified by silica gel column chromatography to give 2.18 g (yield 6%) of tthe captioned compound.

Melting point: 90°–95° C.

$^1$H-NMR spectrum (CDCl$_3$ solution, δ ppm): 2.04 (2H, quintet, J=7 Hz), 2.52 (4H, m), 2.78 (2H, t, J=7 Hz), 2.81 (2H, t, J=7 Hz), 3.56 (2H, s), 3.83 (4H, m), 7.35 (5H, s), 8.12 (1H, s).

Example 27A 6,7-Dihydro-2-piperazino(5H)cyclopentapyrimidine (compound No. 200):

2.0 g (6.79 mmoles) of 2-(4-benzylpiperazino)-6,7-dihydro(5H)cyclopentapyrimidine (compound No. 208 of Example 26A) was dissolved in 40 ml of ethanol, and hydrogenated in the presence of 0.20 g of 10% Pd-C at 70° C. under atmospheric pressure. Four hours later, the catalyst was separated by filtration. Ethanol was evaporated to give 1.38 g (yield 99%) of the captioned compound as crystals.

Melting point: 107°–113° C.

$^1$H-NMR spectrum (CDCl$_3$ solution, δ ppm): 2.05 (2H, quintet, J=7 Hz), 2.80 (2H, t, J=7 Hz), 2.83 (2H, t, J=7 Hz), 2.96 (4H, m), 3.81 (4H, m), 8.13 (1H, s).

Example 28A 6,7-Dihydro-2-piperazino(5H)cyclopentapyrimidine hydrochloride (compound No. 202):

0.47 g (2.30 mmoles) of 6,7-dihydro-2-piperazino(5H-)cyclopentapyrimidine compound No. 200 of Example 27A) was dissolved in 5 ml of ethanol, and 0.22 g (2.57 mmoles) of concentrated hydrochloric acid was added. The mixture was stirred at room temperature for 10 minutes. Acetone (40 ml) was added, and the mixture was further stirred for 10 minutes. The crystals that precipitated were collected by filtration to give 0.22 g (yield 40%) of the captioned compound.

Melting point: higher than 300° C.

$^1$H-NMR spectrum (DMSO-d$_6$ solution, δ ppm): 2.00 (2H, quintet, J=7 Hz), 2.78 (4H, t, J=7 Hz), 3.12 (4H, m), 3.96 (4H, m), 8.24 (1H, s), 9.33 (2H, br).

Example 29A 2-(4-Benzylpiperazino)-5,6-dihydrofuro[2,3-d]pyrimidine (compound No. 926):

(1) 10.0 g (73.5 mmoles) of 2-hydroxymethylenebutyrolactone sodium salt [synthesized by the method described in J. O. Fissekis et al., J. Org., Chem. 29, 2670 (1964)] and 19.6 g (73.3 mmoles) of 1-amidino-4-benzylpiperazine sulfate were added to 360 ml of ethanol, and the solution was refluxed for 5 hours. Ethanol was evaporated, and the residue was mixed with water and extracted with chloroform. The chloroform layer was dried, concentrated, and purified by silica gel column chromatography to give 6.66 g (yield 29%) of 2-(4-benzylpiperazino)-4-hydroxy-5-(2-hydroxyethyl)-pyrimidine as crystals.

Melting point: 166°–170° C.

$^1$H-NMR spectrum (CDCl$_3$ solution, δ ppm): 2.56 (6H, m), 3.56 (2H, s), 3.60–3.90 (6H, m), 7.35 (5H, s), 7.67 (1H, s).

(2) Thionyl chloride (40 ml) was added at 0° C. to 2.0 g (6.36 mmoles) of the compound obtained in (1) above. The mixture was stirred at 0° C. for 4 hours and at room temperature for 12 hours. The excess of thionyl chloride was evaporated under reduced pressure. Water was added to dissolve the residue. The solution was made alkaline with 2N aqueous sodium hydroxide solution and then extracted with chloroform. The chloroform layer was dried, concentrated, and purified by silica gel column chromatography to give 1.03 g (yield 55%) of the captioned compound as crystals.

Melting point: 121°–123° C.

$^1$H-NMR spectrum (CDCl$_3$ solution, δ ppm): 2.48 (4H, m), 3.09 (2H, t, J=7 Hz), 3.55 (2H, s), 3.81 (4H, m), 4.60 (2H, t, J=7 Hz), 7.34 (5H, s), 7.99 (1H, s).

Example 30A 5,6-Dihydro-2-piperazinofuro[2,3-d]pyrimidine (compound No. 900):

1.21 g (4.08 mmoles) of 2-(4-benzylpiperazino)-5,6-dihydrofuro[2,3-d]pyrimidine (compound No. 926 of Example 29A) was dissolved in 40 ml of ethanol, and hydrogenated in the presence of 0.14 g of 10% Pd-C at 70° C. under atmospheric pressure. Four hours later, the catalyst was separated by filtration, and ethanol was evaporated to give 0.81 g (yield 96%) of the captioned compound as crystals.

Melting point: 74°–78° C.

$^1$H-NMR spectrum (CDCl$_3$ solution, δ ppm): 2.49 (1H, s), 2.92 (4H, m), 3.12 (2H, dt, J=1, 7 Hz), 3.80 (4H, m), 4.62 (2H, t, J=7 Hz), 8.00 (1H, t, J=1 Hz).

Example 31A 5,6-Dihydro-2-piperazinofuro[2,3-d]pyrimidine hydrochloride (compound No. 902):

0.23 g (1.12 mmoles) of 5,6-dihydro-2-piperazinofuro[2,3-d]pyrimidine (compound No. 900 of Example 30A) was dissolved in 10 ml of ethanol, and 0.12 g (1.18 mmoles) of concentrated hydrochloric acid was added. The mixture was stirred at room temperature for 1 hour. The crystals that precipitated were collected by filtration, and washed with acetone to give 0.27 g (yield about 100%) of the captioned compound.

Melting point: 294° C. (decomp.)

$^1$H-NMR spectrum (DMSO-d$_6$ solution, δ ppm): 3.16 (6H, m), 3.92 (4H, m), 4.70 (3H, t, J=8 Hz), 8.10 (1H, s), 9,54 (2H, br).

Example 32A 2-(4-Benzylpiperazino)-4,6-dimethylfuro[2,3-d]pyrimidine (compound No. 928):

To 14.45 g (54.1 mmoles) of 1-amidino-4-benzylpiperazine sulfate were added 15 ml of DMSO, 3.57 g (54.1 mmoles) of 85% potassium hydroxide and 10.0 g (64.9 mmoles) of 3-carbomethoxy-5-hexyn-2-one [synthesized by the method described in K. E. Schulte et al., Arch. Pharm., 295, 627 (1962)], and the mixture was heated at 140° C. for 4.5 hours. Water was added, and the mixture was extracted with chloroform. The chloroform layer was washed with water and saturated aqueous sodium chloride solution, dried and concentrated. The residue was purified by silica gel column chromatography to give 4.84 g (yield 28%) of the captioned compound as a yellow oil.

$^1$H-NMR spectrum (CDCl$_3$ solution, δ ppm): 2.36 (3H, d, J=1 Hz), 2.47 (3H, s), 2.51 (4H, m), 3.55 (2H, s), 3.87 (4H, m), 6.17 (1H, d, J=1 Hz), 7.34 (5H, s).

Example 33A 4,6-Dimethyl-2-piperazinofuro[2,3-d]pyrimidine (compound No. 904):

4.23 g (13.1 mmoles) of 2-(4-benzylpiperazino)-4,6-dimethylfuro[2,3-d]pyrimidine (compound No. 928 of Example 32A) was dissolved in 50 ml of ethanol and hydrogenated in the presence of 0.40 g of 10% Pd-C at 70° C. under atmospheric pressure. Five hours later, the catalyst was separated by filtration, and washed with chloroform. The ethanol layer and the chloroform layer were combined, concentrated, and recrystallized from ethanol to give 1.94 g (yield 64%) of the captioned compound as crystals.

Melting point: higher than 300° C.

$^1$H-NMR spectrum (CDCl$_3$-DMSO-d$_6$ solution, δ ppm): 2.40 (3H, d, J=1 Hz), 2.50 (3H, s), 3.19 (4H, m), 4.12 (4H, m), 6.35 (1H, d, J=1 Hz).

Example 34A 4,6-Dimethyl-2-piperazinofuro[2,3-d]pyrimidine hydrochloride (compound No. 906):

0.81 g (3.49 mmoles) of 4,6-dimethyl-2-piperazinofuro[2,3-d]pyrimidine (compound No. 904 of Example 33A) was dissolved in 200 ml of ethanol under heat, and 0.39 g (3.84 mmoles) of concentrated hydrochloric acid was added. The mixture was stirred at room temperature for 30 minutes, and ethanol was evaporated under reduced pressure. The residue was washed with acetone to give 0.88 g (yield 94%) of the captioned compound as crystals.

Melting point: higher than 300° C.

$^1$H-NMR spectrum (DMSO-d$_6$ solution, δ ppm): 2.36 (3H, d, J=1 Hz), 2.50 (3H, s), 3.12 (4H, m), 3.98 (4H, m), 6.57 (1H, d, J=1 Hz), 9.60 (2H, br).

Example 35A 2-(4-Benzylpiperazino)-5,6-dihydro-7-methyl(7H-)pyrrolo[2,3-d]pyrimidine (compound No. 930):

(1) Sodium borohydride (2.24 g) was added to 8.0 g of 2-(4-benzylpiperazino)-5,6-dihydro-7-methyl-6-oxo-(7H)pyrrolo[2,3-d]pyrimidine (produced in accordance with Referential Example 54 of Japanese Laid-Open Patent Publication No. 140568/1986) and 400 ml of ethanol, and the mixture was heated under reflux for 1.5 hours. The reaction mixture was concentrated. The residue was mixed with water and extracted with ethyl acetate. The organic layer was dried over anhydrous sodium sulfate, and the solvent was evaporated. The residue was purified by silica gel column chromatography (methanol:chloroform=1:10), and recrystallized from toluene to give 2.4 g (yield 30%) of 2-(4-benzylpiperazino)-5-(2-hydroxyethyl)-4-methylaminopyrimidine as colorless crystals.

Melting point: 119°–120° C.

$^1$H-NMR spectrum (CDCl$_3$ solution, δ ppm): 2.3–2.7 (6H, m), 2.94 (3H, d, J=4.3 Hz), 3.55 (2H, s), 3.6–3.9 (6H, m), 5.50 (1H, br.d, J=4.3 Hz), 7.2–7.5 (5H, m), 7.61 (1H, s).

(2) The compound obtained in (1) (8.0 g) and 80 ml of pyridine were cooled to −10° to 0° C., and a solution of 5.3 g of p-toluenesulfonyl chloride in 100 ml of pyridine was added dropwise. After the addition, the mixture was reacted at 0° to 5° C. for 6 hours. A solution of 2.5 g of sodium hydrogen carbonate in 30 ml of water was gradually added to the reaction mixture, and the mixture was further stirred for 15 minutes. The reaction mixture was mixed with 200 ml of water, and extracted with 300 ml of ethyl acetate. The ethyl acetate layer was washed with 200 ml of water and dried over anhydrous sodium sulfate. Ethyl acetate was evaporated. The residue was suspended in 100 ml of tetrahydrofuran, and 2.4 g of 60% sodium hydride washed with hexane was added as a suspension in tetrahydrofuran. After reacting at room temperature for 5 hours, 10 ml of ice water was gradually added. The solvent was evaporated, and 200 ml of water and 300 ml of ethyl acetate were added to the residue. The aqueous layer was separated, and the ethyl acetate layer was washed with 200 ml of water, and dried over anhydrous sodium sulfate. The solvent was evaporated, and the residue was purified by silica gel chromatography (acetone:hexane=1:1) to give 1.6 g (yield 21%) of the desired product as light brown crystals.

Melting point: 105°–107° C.

$^1$H-NMR spectrum (CDCl$_3$ solution, δ ppm): 2.48 (4H, m), 2.84 (2H, t, J=9 Hz), 3.50 (2H, t, J=9 Hz), 3.55 (2H, s), 3.78 (4H, m), 7.34 (5H, s), 7.60 (1H, s).

Example 36A 5,6-Dihydro-7-methyl-2-piperazino(7H)pyrrolo[2,3-d]pyrimidine (compound No. 912):

Ethanol (15 ml) was added to 1.4 g of 2-(4-benzylpiperazino)-5,6-dihydro-7-methyl(7H)pyrrolo[2,3-d]pyrimidine (compound No. 930 of Example 35A) and 0.14 g of 10% Pd-C. The mixture was stirred at 60° C. for 8 hours in a hydrogen atmosphere. After cooling, the 10% Pd-C was separated by filtration, and the solvent was evaporated to give 0.94 g (yield 95%) of the desired compound as colorless crystals.

Melting point: 63°–65° C.

$^1$H-NMR spectrum (CDCl$_3$ solution, δ ppm): 2.90 (2H, t, J=9 Hz), 2.92 (4H, m), 3.48 (2H, t, J=9 Hz), 3.74 (4H, m), 7.62 (1H, s).

Example 37A 5,6-Dihydro-7-methyl-2-piperazino(7H)pyrrolo[2,3-d]pyrimidine naphthalene-2-sulfonate (compound No. 914):

A solution of 0.26 g of 2-naphthalenesulfonic acid monohydrate in 10 ml of ethanol was added to a solution of 0.25 g of 5,6-dihydro-7-methyl-2-piperazino(7H-)pyrrolo[2,3-d]pyrimidine (compound No. 912 of Example 36A). The solvent was evaporated to give 0.49 g (yield 100%) of the desired product as colorless crystals.

Melting point: 160°–162° C.

$^1$H NMR spectrum (DMSO-d$_6$ solution, δ ppm): 2.88 (3H, s), 2.7–3.7 (8H, m), 7.4–8.1 (7H, m), 8.14 (1H, s).

Example 38A 2-(4-Benzylpiperazino)-7,8-dihydro-7-methyl-5-oxo(5H)pyrano[4,3-d]pyrimidine (compound No. 932):

0.5 g of 4,6-dioxo-2-methyloxane, 2.0 ml of methyl orthoformate and 50 ml of acetic anhydride were stirred at 130° C. for 3 hours. After the reaction, the solvent was evaporated by an evaporator to obtain a liquid substance. 1.04 g of 1-amidino-4-benzylpiperazine sulfate was added to 10 ml of 2% aqueous KOH solution. The mixture was stirred at room temperature for 30 minutes, and the above liquid substance was added to the resulting solution. The mixture was stirred at room temperature for 1 hour. After the reaction, methanol was evaporated, and 30 ml of water was added. The mixture was extracted with 50 ml of methylene chloride. The methylene chloride layer was dried over anhydrous sodium sulfate, and the solvent was evaporated. The residue was purified by silica gel column chromatography (methylene chloride:ethyl acetate=2:1) to give 0.82 g (yield 62%) of the captioned compound as a white solid.

$^1$H-NMR spectrum (CDCl$_3$ solution, δ ppm): 1.56 (3H, d, J=8.6 Hz), 2.56 (4H, m), 2.84 (2H, d, J=7.6 Hz), 3.60 (2H, s), 4.00 (4H, m), 4.70 (1H, m), 7.38 (5H, s), 8.86 (1H, s).

Example 39A 7,8-Dihydro-7-methyl-5-oxo-2-piperazino(5H-)pyrano[4,3-d]pyrimidine (compound No. 916):

0.15 g of 2-(4-benzylpiperazino)-7,8-dihydro-7-methyl-5-oxo(5H)pyrano[4,3-d]pyrimidine (compound No. 932 of Example 38A) was dissolved in 30 ml of ethanol, and 30 mg of 10% Pd-C was added under a nitrogen atmosphere. The mixture was stirred at 50° C. for 2 hours in a nitrogen atomosphere. After the reaction, Pd-C was separated by filtration. The solution was concentrated to give 0.12 g (yield 99%) of a solid.

$^1$H-NMR spectrum (CDCl$_3$ solution, δ ppm): 1.52 (3H, d, J=6.8 Hz), 2.84 (2H, d, J=7.6 Hz), 2.94 (4H, m), 3.96 (4H, m), 4.64 (1H, m), 8.86 (1H, s).

Example 40A 7,8-Dihydro-7-methyl-5-oxo-2-piperazino(5H-)pyrano[4,3-d]pyrimidine hydrochloride (compound No. 918):

Five milliliters of a HCl-saturated ethanol solution was added to 0.12 g of 7,8-dihydro-7-methyl-5-oxo-2-piperazino(5H)pyrano[4,3-d]pyrimidine (compound No. 916 of Example 39A), and the mixture was stirred at room temperature for 10 minutes. The reaction mixture was concentrated to give 0.13 g of the captioned compound as a solid. Melting point: 274°–276° C. (decomp.)

Example 41A 2-(4-Benzylpiperazino)-5,6-dihydro-4,7-dimethyl-6-oxo(7H)pyrrolo[2,3-d]pyrimidine (compound No. 462):

(1) Potassium hydroxide (3.1 g) was added to 200 ml of ethanol, and the mixture was stirred for 30 minutes. Then, 12.4 g of 1-amidino-4-benzylpiperazine sulfate was added. The mixture was stirred at room temperature for 10 minutes. To the solution was added 12.4 g of diethyl acetylsuccinate. The mixture was refluxed for 2 hours. Then, 200 ml of toluene was added, and the mixture was refluxed for 3 hours. After the reaction, ethanol was evaporated, and the residue was poured into 50 ml of an aqueous solution of hydrochloric acid. NaHCO$_3$ was added to the solution to neutralize it. The precipitated solid was washed with water and dried over P$_2$O$_5$ to give 2.55 g (yield 15%) of 2-(4-benzylpiperazino)-5-ethoxycarbonylmethyl-4-hydroxy-6-methylpyrimidine as a white solid.

$^1$H-NMR spectrum (DMSO-d$_6$ solution, δ ppm): 1.36 (3H, t, J=7.6 Hz), 2.25 (3H, s), 2.57 (4H, m), 3.55 (2H, s), 3.69 (2H, s), 3.77 (4H, m), 4.24 (4H, q, J=7.6 Hz), 7.51 (5H, s).

(2) The compound obtained in (1) above (2.7 g) and 20 g of phosphorus oxychloride were refluxed for 3 hours. Phosphorus oxychloride was evaporated under reduced pressure, and 10 ml of toluene was added. The resulting solid was collected by filtration, and then stirred for about 1 hour together with 50 ml of methylene chloride and 50 ml of saturated aqueous sodium bicarbonate solution. The toluene layer and the methylene chloride layer were combined, and dried over anhydrous sodium sulfate. The solution was concentrated to give 2.61 g (yield 92%) of 2-(4-benzylpiperazino)-5-ethoxycarbonylmethyl-4-chloro-6-methylpyrimidine as a light brown solid.

$^1$H-NMR spectrum (DMSO-d$_6$ solution, δ ppm): 1.26 (3H, t, J=7.6 Hz), 2.35 (3H, s), 2.48 (4H, m), 3.56 (2H, s), 3.65 (2H, s), 3.82 (4H, m), 4.18 (2H, q, J=7.6 Hz), 7.34 (5H, s).

(3) 2.61 g of the compound obtained in (2) and a 40% methylamine methanol solution containing 1.04 g of methylamine were dissolved in ethanol, and the solution was stirred at 120° C. for 18 hours in a nitrogen atmosphere in a 50 ml autoclave. After cooling, the red crystals that precipitated were collected by filtration to obtain a solid. The filtrate was concentrated to 3 ml to obtain secondary crystals. The primary and secondary crystals were combined to give 1.56 g (yield 62%) of the captioned compound as red crystals.

$^1$H-NMR spectrum (CDCl$_3$ solution, δ ppm): 2.22 (3H, s), 2.50 (4H, m), 3.18 (3H, s), 3.34 (2H, s), 3.56 (2H, s), 3.86 (4H, m), 7.35 (5H, s).

Example 42A 5,6-Dihydro-4,7-dimethyl-6-oxo-2-piperazino(7H-)pyrrolo[2,3-d]pyrimidine (compound No. 464):

1.56 g (4.6 mmoles) of 2-(4-benzylpiperazino)-5,6-dihydro-4,7-dimethyl-6-oxo(7H)pyrrolo[2,3-d]pyrimidine (compound No. 462 of Example 41A) was dissolved in 60 ml of ethanol, and 500 mg of 10% Pd-C was added under a nitrogen atmosphere. The mixture was stirred at 70° C. for 2 hours in a nitrogen atmosphere. After the reaction, Pd-C was separated by filtration, and the solution was concentrated to give 1.04 g (yield 91%) of the captioned compound as a pale yellow solid.

$^1$H-NMR spectrum (CDCl$_3$ solution, δ ppm): 2.24 (3H, s), 2.92 (4H, m), 3.20 (3H, s), 3.36 (2H, s), 3.82 (4H, m).

Example 43A 5,6-Dihydro-4,7-dimethyl-6-oxo-2-piperazino(7H-)pyrrolo[2,3-d]pyrimidine hydrochloride (compound No. 466):

0.20 g of 5,6-dihydro-4,7-dimethyl-6-oxo-2-piperazino(7H)pyrrolo[2,3-d]pyrimidine was dissolved in 20 ml of ethanol saturated with hydrochloric acid. The mixture was stirred at room temperature for 10 minutes, and concentrated to give 0.21 g of the captioned compound having a melting point of more than 300° C. as a pale yellow solid.

Example 44A

Methyl 2-(4-ethoxycarbonylmethylpiperazino)-4-isopropylaminopyrimidine-5-carboxylate (compound No. 100):

Ethyl bromoacetate (0.5 g; 3.1 mmoles) was added to 0.9 g (3.2 mmoles) of 2-piperazino-4-isopropylaminopyrimidine-5-carboxylate (produced in accordance with Referential Example 69 of Japanese Laid-Open Patent Publication No. 140568/1986), 10 ml of CHCl$_3$ and 0.54 g (5.3 mmoles) of triethylamine, and the mixture was stirred at room temperature for 6 hours. Then, water was added, and the mixture was extracted with CHCl$_3$. The CHCl$_3$ layer was dried over anhydrous MgSO$_4$. CHCl$_3$ was evaporated under reduced pressure. The residue was purified by silica gel column chromatography (ethyl acetate) to give 1.0 g (yield 88%) of the desired product.

Melting point: 78°–79° C.

$^1$H-NMR spectrum (CDCl$_3$ solution, δ ppm): 1.27 (6H, d, J=7 Hz), 1.31 (3H, t, J=7 Hz), 2.64 (4H, m), 3.27 (2H, s), 3.82 (3H, s), 3.96 (4H, m), 4.22 (2H, q, J=7 Hz), 4.26 (1H, m), 7.94 (1H, br. d, J=7 Hz), 8.59 (1H, s).

Example 45A

2-Piperazino-5-(2-hydroxyethyl)-4-methylaminopyrimidine (compound No. 138):

A mixture of 0.8 g (2.54 mmoles) of 2-(4-benzylpiperazino)-5-(2-hydroxyethyl)-4-methylaminopyrimidine, 0.1 g of 10% Pd-C and 10 ml of ethanol was stirred at 60° C. for 7 hours in a hydrogen atmosphere. The reaction mixture was allowed to cool, and the catalyst was removed by filtration. The filtrate was concentrated to give 0.56 g (yield 96%) of the captioned compound as crystals.

Melting point: 195°–197° C.

$^1$H-NMR spectrum (CDCl$_3$-DMSO-d$_6$ solution, δppm): 2.50 (2H, t, J=7 Hz), 2.92 (3H, s), 2.98 (4H, m), 3.62 (2H, t, J=7 Hz), 3.84 (4H, m), 6.45 (1H, br), 7.58 (1H, s).

Example 46A

2-Piperazino-5-(2-hydroxyethyl)-4-methylaminopyrimidine 2-naphthalenesulfonate (compound No. 140):

A solution of 0.18 g (0.8 mmole) of 2-naphthalenesulfonic acid in 10 ml of ethanol was added to a solution of 0.19 g (0.8 mmole) of 2-piperazino-5-(2-hydroxyethyl)-4-methylaminopyrimidine in 30 ml of ethanol. The mixture was stirred at room temperature for 30 minutes. The reaction mixture was concentrated, and the precipitated solid was slurried with a mixture of ether, toluene and ethanol. The solid was collected by filtration, and dried under reduced pressure to give 0.2 g (yield 54%) as colorless crystals.

Melting point: 215°–217° C.

Example 47A 6,7-Dimethoxy-2-[4-(3,4-dimethoxybenzoyl)-piperazino]quinazoline (compound No. 944):

Two milliliters of isoamyl alcohol was added to 125 mg of 1-(3,4-dimethoxybenzoyl)piperazine (synthesized by the method described in Japanese Laid-Open Patent Publication No. 150072/1981) and 112 mg of 2-chloro-6,7-dimethoxyquinazoline, and the mixture was stirred at 120° C. for 5.5 hours. The isoamyl alcohol was evaporated, and the residue was purified by thin-layer chromatography (ethyl acetate) to give 102 mg (yield 47%) of the captioned compound as colorless crystals.

Melting point: 188°–190° C.

$^1$H-NMR spectrum (CDCl$_3$ solution, δppm): 3.78 (4H, br.s), 3.94 (3H, s), 3.97 (3H, s), 3.99 (3H, s), 4.04 (3H, s), 4.1 (4H, br.s), 6.8–7.2 (5H, m), 8.85 (1H, s).

Example 48A

In accordance with the methods described in Japanese Laid-Open Patent Publication No. 140568/1986, there were produced compounds encompassed within the above formula (I), namely compounds Nos. (204), (206), (300), (302), (304), (306), (308), (400), (402), (404), (406), (408), (420), (422), (424), (428), (432), (452), (454), (500), (502), (504), (506), (600), (602), (604), (606), (608), (610), (612), (614), (616), (618), (620), (622), (624), (626), (628), (630), (632), (634), (700), (701), (702), (704), (706), (707), (708), (710), (712), (714), (716), (718), (720), (722), (724), (726), (728), (730), (732), (734), (736), (738), (740), (742), (744), (746), (748), (800), (802), (804), (806), (936), (938), (940), and (942).

The physical property values of some of these compounds in the 700 series are shown below.

Compound No. 734

Melting point: 170°–172° C.

Infrared absorption spectrum (KBr tablet, cm$^{-1}$): 1657, 1618, 1578.

$^1$H-NMR spectrum (deuterochloroform, δppm): 1.33 (3H, t, J=7.2), 1.66 (1H, s), 2.17 (3H, d, J=1.3), 2.94 (4H, m), 3.97 (6H, m), 7.10 (1H, q, J=1.3), 9.24 (1H, s).

Compound No. 714

Melting point: 143° C.

Infrared absorption spectrum (KBr tablet, cm$^{-1}$): 3325, 1660, 1622, 1576.

$^1$H-NMR spectrum (deuterodimethyl sulfoxide, δppm):
0.88 (3H, t, J=8 Hz), 1.66 (2H, m), 2.75 (4H, t, J=6 Hz), 2.8 (1H, overlapping 2.75), 3.76–3.91 (6H, m), 6.22 (1H, d, J=8 Hz), 7.73 (1H, d, J=8 Hz), 9.08 ((1H, s).

Compound No. 712

Melting point: 161° C.

Infrared absorption spectrum (KBr tablet, cm$^{-1}$): 3430, 1652, 1618, 1584.

$^1$H-NMR spectrum (deuterochloroform, δppm): 1.31 (6H, d, J=8 Hz), 2.92 (4H, br.s), 3.92 (4H, br.s), 5.05 (1H, seq, J=8 Hz), 6.2 (1H, br.s), 6.29 (1H, d, J=8 Hz), 7.83 (1H, d, J=8 Hz), 9.08 (1H, s).

Compound No. 700

Melting point: 252.8° C. (recrystallized from ethanol)
Mass spectrum: 231 (M$^+$).

$^1$H-NMR spectrum (DMSO-d$_6$ solution, δppm): 2.87 (4H, br.s), 3.88 (4H, br.s), 5.73 (1H, d, J=7 Hz), 6.98 (1H, d, J=7 Hz), 9.02 (1H, s).

Compound No. 740

Melting point: 231.7° C.
Mass spectrum: 349 (molecular ion peak)

Infrared absorption spectrum (KBr tablet, cm$^{-1}$): 3400, 2920, 1654, 1617, 1574

$^1$H NMR spectrum (deuterodimethyl sulfoxide, δppm): 1.24 (3H, t, J=7 Hz), 2.96 (4H, br.s), 3.80–4.12 (8H, m), 7.24 (5H, s), 7.80 (1H, s), 8.06 (1H, s).

Compound 708

Melting point: 149°–152° C.

Infrared absorption spectrum (KBr CHCl$_3$, cm$^{-1}$): 1655, 1645, 1620, 1575.

$^1$H NMR spectrum (deuterochloroform, δppm): 1.34 (3H, t, J=7 Hz), 1.87 (1H, br.s), 2.94 (4H, t, J=6 Hz), 3.96 (6H, m), 6.27 (1H, d, J=8 Hz), 7.29 (1H, d, J=8 Hz), 9.22 (1H, s).

Compound 706

Oily $^1$H NMR spectrum (deuterochloroform, δppm): 2.93 (4H, m), 3.50 (3H, s), 3.94 (4H, m), 4.40 (1H, br.s), 6.25 (1H, d, J=8 H), 7.25 (1H, d, J=8 Hz), 9.23 (1H, s).

Compound No. 742

Melting point: higher than 300° C.

Infrared absorption spectrum (nujol, cm$^{-1}$): 3400, 1688, 1655.

$^1$H NMR spectrum (CDCl$_3$ solution, δppm): 1.40 (3H, t, J=7.0 Hz), 2.95 (4H, m), 4.08 (6H, m), 8.19 (1H, s), 9.20 (1H, s), 10.55 (1H, s).

Example 1B

Tablets each containing 10 mg of the active component are prepared as follows:

|  | Per tablet |
| --- | --- |
| Active component | 10 mg |
| Corn starch | 55 mg |
| Crystalline cellulose | 35 mg |
| Polyvinyl pyrrolidone (as 10% aqueous solution) | 5 mg |
| Carboxymethyl cellulose calcium | 10 mg |
| Magnesium stearate | 4 mg |
| Talc | 1 mg |
| Total | 120 mg |

The active component, corn starch and crystalline cellulose are passed through an 80-mesh sieve and completely mixed. The resulting powder is mixed with the polyvinyl pyrrolidone solution. The mixture is granulated and passed through an 18-mesh sieve. The resulting granules are dried at 50° to 60° C., and again passed through an 18-mesh sieve. Carboxymethyl cellulose calcium, magnesium stearate and talc, passed previously through an 80-mesh sieve, are added to the granules and mixed. The mixture are formed into tablets each having a weight of 120 mg by a tableting machine.

Example 2B

Tablets each containing 200 mg of the active component are prepared as follows:

|  | Per tablet |
| --- | --- |
| Active component | 200 mg |
| Corn starch | 50 mg |
| Crystalline cellulose | 42 mg |
| Soft silicic anhydride | 7 mg |
| Magnesium stearate | 1 mg |
| Total | 300 mg |

The above ingredients are passed through an 80-mesh sieve and completely mixed. The resulting powder is compression-molded into tablets each having a weight of 300 mg.

Example 3B

Capsules each containing 100 mg of the active component are prepared as follows:

|  | Per capsule |
| --- | --- |
| Active component | 100 mg |
| Corn starch | 40 mg |
| Lactose | 5 mg |
| Magnesium stearate | 5 mg |
| Total | 150 mg |

The above ingredients are mixed, passed through an 80-mesh sieve, and completely mixed. The resulting powder is filled in capsules each in an amount of 150 mg.

Example 4B

An injecting preparation containing 5 mg of the active component in a vial is prepared as follows:

|  | Per vial |
| --- | --- |
| Active component | 5 mg |
| Mannitol | 50 mg |

Prior to use, the above ingredients are dissolved in 1 ml of distilled water for injection.

Example 5B

An injecting preparation containing 50 mg of the active component is an ampoule is prepared as follows:

|  | Per ampoule |
| --- | --- |
| Active component | 50 mg |
| Sodium chloride | 18 mg |
| Distilled water for injection | suitable amount |
| Total | 2 ml |

Example 6B

An adhesive patch containing 17.5 mg of the active component is prepared as follows:

Ten parts of poly(ammonium acrylate) is dissolved in 60 parts of water. Separately, 2 parts of glycerin diglycidyl ether is dissolved in 10 parts of water while heating. Further, 10 parts of polyethylene glycol (grade 400), 10 parts of water and 1 part of the active component are stirred to form a solution. While the aqueous solution of poly(ammonium acrylate) is stirred, the aqueous solution of glycerin diglycidyl ether and the aqueous solution of the active component and polyethylene glycol are added and mixed. The resulting solution for hydrogel is coated on a pliable plastic film so that the amount of the active component is 0.5 mg per $cm^2$. The surface is covered with releasing paper, and the film is cut to pieces each having an area of 35 $cm^2$ to form an adhesive patch.

Example 7B

An adhesive patch containing 10 mg of the active component is prepared as follows:

An aqueous sol is prepared from 100 parts of poly(sodium acrylate), 100 parts of glycerin, 150 parts of water, 0.2 part of triepoxypropyl isocyanurate, 100 parts of ethanol, 25 parts of isopropyl myristate, 25 parts of propylene glycol and 15 parts of the active component. The sol is then coated to a thickness of 100 micrometers on the non-woven fabric surface of a composite film composed of a rayon non-woven fabric and a polyethylene film to form an adhesive layer containing the drug. The amount of the release aids (isopropyl myristate and propylene glycol) contained in this layer is about 20% by weight. The adhesive layer is then crosslinked at 25° C. for 24 hours, and a releasing film is bonded to the adhesive layer surfce, and the entire film is cut into pieces each having an area of 35 $cm^2$.

The biological activities in vitro of the compounds of formula (I) on cells of the nervous system were tested. The cells tested were human neuroblastoma cell line GOTO [see Sekiguchi, M., Oota, T., Sakakibara, K., Inui, N. & Fujii, G., Japan. J. Exp. Med., 49, 67–83 (1979)], and neuroblastoma cell line NB-1 [see Miyake, S., Shimo, Y., Kitamura, T., Nojyo, Y., Nakamura, T., Imkashuku, S. and Abe, T., The Autonomic Nervous System, 10, 115–120 (1973)], and mouse neuroblastoma cell line neuro-2a (Dainippon Pharmaceutical Co., Ltd.) which have been established as the cells of the nervous system. The above neuve cells were grown in an incubator at 37° C. in the presence of 5% carbon dioxide gas exponentially, and then cultivated for a certain period of time together with the compounds of formula (I). The results demonstrated that the compounds of formula (I) have nerve cell growth promoting activity and neurite formation and sprouting promoting activity which are markedly higher with a significance than a control, and are equal to, or higher than, isaxonine as a control drug (the compound described in Japanese Patent Publication No. 28548/1984).

The biological activities of the compounds of formula (I) in accordance with this invention on rat PC-12 pheochromocytoma cell line were also tested. When NGF is added to PC-12 cells, the neurites sprout. It was shown that when the compound (I) of this invention is added at this time, the binding of NGF to the PC-12 cells and the up-take of NGF into the cells increased.

When the effect of the compounds (I) of this invention on the binding of NGF to rabbit superior cervical ganglion was examined, they were found to promote the NGF binding.

Rats whose sciatic nerves were crushed were prepared as a model of peripheral nervous disorder, and the effects of the compounds of this invention on it were tested. It was made clear that the compounds (I) of the present invention have an effect of promoting recovery of the interdigit distance and the weight of the soleus muscle to normal values.

Rats and mice models of central nervous disorders were prepared, and the pharmacological effects of the compounds (I) of this invention were tested. Specifically, nigral dopamine cells of the rat brain were chemically destroyed by injecting a very small amount of 6-hydroxydopamine to induce motor imbalance. Two weeks later, dopamine cells of fetal brain were transplanted in the caudate nucleus into the lesioned side of the rat brain and an attempt was made to improve the motor trouble. Specifically, beginning on the day of transplantation, the compound (I) of the invention was intraperitoneally administered every day over 2 weeks, and the activity of the compounds (I) of the invention on the improvement of the motor imbalance and the growth of the transplanted cells was examined. It was found that the compounds (I) of the invention have a promoting effect on the improvement of the motor trouble.

Rats and mice having a nerve trouble by mercury poisoning were prepared and the activity of the compounds (I) of the invention was tested. The compounds (I) were found to have a promoting effect and a curative effect on the improvement of the condition and recovery to a normal condition.

Thus, it has been made clear that the compounds (I) of this invention are useful as agents for improving or curing various neurological diseases of mammals, such as troubles in peripheral and central nerves.

Various types of neuropathy including, for example, various peripheral nerve disorders accompanied by motorgenic, seonsory or objective flex retardation, and alcohol-induced or drug-induced, diabetic and metabolic, or idiopathic peripheral nerve disorders, including traumatic, inflammatory or immunological nerve root lesions may be cited as such neurological diseases. More specific examples include facial palsy, sciatic nerve paralysis, spinal muscular atropy, muscular dystrophy, myasthenia gravis, multiple sclerosis, amyotrophic lateral sclerosis, acute disseminated cerebromyelitis, Guillan-Barre syndrome, postvaccinal encephalomyelitis, SMON disease, dementia, Alzheimer syndrome, a condition after cranial injury, cerebral ischemia, sequela of cerebral infarction or cerebral hemmorrhage, and rheumatism. These examples are not limitative.

By a toxicity test, the compounds of this invention were found to have only weak toxicity, and be useful as safe medicines.

Example 1C

The effect of the compounds of this invention on neuroblastoma cells was examined by the following method.

A culture medium [composed of 45% of RPMI 1640 medium, 45% modified Eagle's medium (MEM) and 10% of fetal calf serum (FCS) and containing penicillin G sodium (100 units/ml) and streptomycin sulfate (100 microgram/ml)] containing neurobalstoma cell line GOTO in the logarithmic growth period was poured in an amount of 2 ml each into polystyrene dishes (35 mm; made by Corning Co.) so that the cell concentration was 2 to $6 \times 10^4$ cells per dish, and the cells were cultured for 1 to 2 days in a carbon dioxide gas incubator containing 5% of carbon dioxide gas in air at 37° C. Then, the culture fluid was removed, and 2 ml of a fresh serum-free culture fluid (consisting of 50% of RPMI medium and 50% of MEM medium and containing penicillin G sodium and streptomycin sulfate in the same amounts as above) was added. At the same time, a presterilized PBS solution (phosphate buffered saline) of each of the test compounds in various concentrations was added to each of the dishes. After culturing for 24 hours, the number of living cells was counted. Furthermore, the culture was photographed, and from the photos, the number and length of neurites per cell were measured. The numer of living cells was counted for 3 to 6 dishes by resistance to staining with erythrosine dye. The number and length of the neurites were measured with regard to 6 photos (more than 200 cells per photo).

As a simple method of evaluation, the number of cells have neurites with a length equal to, or larger than, the long diameter of the cell was divided by the total number of cells. The results are shown in Tables 1 and 2.

In order to examine the effects of the test compounds, the following method was also employed.

Mouse neuro 2a cells in the logarithmic growth period in the Dulbecco's modified Eagle's medium (DMEM) containing 10% FCS was seeded in a 48-well plate so that the number of cells was 1,000 cells/well, and cultured for one day in 0.25 ml of the culture fluid in each well. The culture medium was then replaced by a medium containing each of the test compounds and FCS, and the cells were further cultured for 24 hours. Then, a 4% aqueous glutaraldehyde solution in the same amount as the medium (0.25 ml) was added, and the culture fluid was left to stand at room temperature for 2 hours to fix the cells. After washing with water, a 0.05% aqueous solution of methylene blue was added to stain the cells. Under a microscope, the number of cells containing outgrown neurites (cells having at least one neutrite with a length at least two times as large as the long diameter of the cell) was counted visually, and the proportion of these cells in the entire cells was calculated. The well was observed over 5 or more visual fields (at least 2% of the entire surface area of the well) continuous to the left and right from a mark put at the center of the well, and more than 200 cells was counted. One drug compound was used in 6 different concentrations at most, and three runs were conducted for each concentration. The results were expressed as a mean of ±S.D., and the results are shown in Table 3.

TABLE 1

Activity on neuroblastoma cell line GOTO

| | Compound | Concentration (μg/ml) | Number of cells × 10⁴/dish (mean ± S.E.) | Number of neurites/cell (mean ± S.D.) | Length of neurites μm/cell (mean ± S.D.) |
|---|---|---|---|---|---|
| Run No. 1 | Control | | 14.34 ± 0.72 | 2.09 ± 0.61 | 70.10 ± 43.03 |
| | Isaxonine | 1 | 17.63 ± 2.80 | 2.18 ± 0.77 | 87.86 ± 56.03 |
| | | 10 | 19.18 ± 0.67 | 1.99 ± 0.51 | 82.87 ± 50.70 |
| | (710) | 10 | 19.18 ± 0.67 | 2.12 ± 0.51 | 86.10 ± 50.70 |
| | | 100 | 11.92 ± 0.66 | 1.71 ± 0.59 | 47.34 ± 35.11 |
| | (940) | 10 | 21.55 ± 2.36 | 2.12 ± 0.60 | 77.92 ± 49.91 |
| Run No. 2 | Control | | 12.30 ± 1.48 | 2.06 ± 0.60 | 55.00 ± 37.26 |
| | Isaxonine | 1 | 14.89 ± 1.35 | 2.09 ± 0.66 | 66.01 ± 40.21 |
| | (710) | 1 | 17.44 ± 1.50 | 2.14 ± 0.63 | 73.74 ± 43.49 |
| | | 10 | 15.15 ± 2.26 | 2.09 ± 0.62 | 62.74 ± 35.64 |
| | (136) | 1 | 12.85 ± 2.52 | 2.14 ± 0.63 | 60.24 ± 34.28 |
| | (604) | 1 | 14.41 ± 2.98 | 2.29 ± 0.77 | 76.30 ± 51.49 |
| | | 10 | 11.85 ± 1.36 | 2.27 ± 0.62 | 72.06 ± 42.79 |
| | (408) | 1 | 17.52 ± 2.57 | 2.11 ± 0.65 | 66.09 ± 36.49 |
| | | 10 | 13.07 ± 0.80 | 2.17 ± 0.66 | 69.33 ± 40.68 |
| Run No. 3 | Control | | 3.17 | 1.94 ± 0.69 | 45.13 ± 22.71 |
| | Isaxonine | 1 | 4.72 | 2.31 ± 0.86* | 68.29 ± 24.83* |
| | (710) | 0.0 | 3.66 | 2.24 ± 1.04* | 70.65 ± 27.90* |
| | | 1 | 3.92 | 2.17 ± 0.79* | 60.93 ± 23.66* |
| | (706) | 0.1 | 3.81 | 2.30 ± 0.75* | 72.11 ± 26.58* |
| | | 1 | 4.12 | 2.26 ± 0.82* | 63.24 ± 28.17* |
| | (124) | 0.0 | 4.01 | 2.28 ± 0.93* | 71.24 ± 27.47* |
| | | 1 | 4.10 | 2.23 ± 0.82* | 66.56 ± 22.16* |
| Run No. 4 | Control | | 5.48 ± 1.38 | 1.98 ± 0.74 | 54.15 ± 33.64 |
| | Isaxonine | 1 | 9.44 ± 1.95 | 1.99 ± 0.70 | 71.25 ± 40.39 |
| | (124) | 1 | 7.22 ± 1.98 | 2.13 ± 0.72 | 72.19 ± 49.23 |
| | | 10 | 5.45 ± 2.61 | 2.08 ± 0.69 | 71.31 ± 45.67 |
| Run No. 5 | Control | | 5.30 ± 0.23 | 1.96 ± 0.64 | 46.41 ± 33.28 |
| | (124) | 1 | 4.89 ± 0.59 | 1.96 ± 0.54 | 52.59 ± 32.50 |
| | (132) | 1 | 5.63 ± 0.68 | 1.95 ± 0.46 | 52.61 ± 32.09 |
| | | 10 | 6.26 ± 0.27 | 2.03 ± 0.63 | 52.85 ± 30.00 |
| | Control | | Not measured | 1.79 ± 0.80 | 42.48 ± 19.64 |
| | Isaxinone | 1 | | 2.00 ± 0.86Δ | 58.20 ± 25.40* |
| | (604) | 1 | | 2.23 ± 0.81* | 58.88 ± 22.72* |
| | (616) | 1 | | 2.04 ± 0.91+ | 56.68 ± 23.36* |
| | | 10 | | 2.13 ± 0.91* | 57.96 ± 27.96* |
| | (628) | 1 | | 1.90 ± 0.81 | 55.72 ± 25.08* |
| | | 10 | | 2.06 ± 0.81 | 53.68 ± 22.36* |
| | Control | | Not measured | 1.77 ± 0.68 | 42.20 ± 17.75 |
| | Isaxinone | 1 | | 1.91 ± 0.56 | 57.06 ± 28.78* |
| | (802) | 10 | | 2.02 ± 0.71+ | 52.16 ± 19.79* |
| | (502) | 1 | | 1.99 ± 0.65+ | 52.24 ± 23.92* |
| | (100) | 10 | | 2.00 ± 0.79Δ | 56.06 ± 26.47* |

In Runs Nos. 3, 6 and 7, significant differences were determined.
*P <0.01, +P <0.05, ΔP <0.1

TABLE 2

Activity on cell lines GOTO and neuro-2a (simple method)

| | | Compound | Concentration (μg/ml) | Number of cells having neurites with a length equal to, or larger than, the long diameter of the cell/total number of cells (%) | Average of the proportions (%) |
|---|---|---|---|---|---|
| Run No. 1 | GOTO | Control | | 13/144 (9.0), 13/156 (8.3), 12/153 (7.8) | 8.4 |
| | | Isaxinone | 10 | 31/252 (12.3), 34/251 (13.5), 31/262 (11.8) | 12.5 |
| | | (604) | 10 | 44/203 (21.7), 46/218 (21.1), 47/224 (21.0) | 21.3 |
| | | (408) | 10 | 37/140 (26.4), 36/149 (24.2), 39/154 (25.3) | 25.3 |
| Run No. 2 | GOTO | Control | | 13/144 (9.0), 13/156 (8.3), 12/153 (7.8) | 8.4 |
| | | Isaxinone | 10 | 31/252 (12.3), 34/251 (13.5), 31/262 (11.8) | 12.5 |
| | | (710) | 10 | 26/187 (13.9), 33/209 (15.8), 31/204 (15.2) | 15.0 |
| | | (706) | 10 | 33/205 (16.1), 35/223 (15.8), 40/237 (16.9) | 16.3 |
| Run No. 1 | neuro-2a | Control | | 12/136 (8.8), 11/150 (7.4), 11/145 (7.6) | 7.9 |
| | | Isaxinone | 1 | 25/221 (11.3), 29/213 (13.6), 24/209 (11.5) | 12.1 |
| | | (710) | 1 | 31/176 (17.6), 27/165 (16.4), 22/161 (13.7) | 15.9 |
| | | | 10 | 26/174 (14.9), 21/159 (13.2), 21/162 (13.0) | 13.7 |
| | | (706) | 1 | 40/209 (19.3), 32/177 (18.1), 27/191 (14.1) | 17.2 |
| | | | 10 | 29/203 (14.3), 32/178 (18.0), 28/200 (14.0) | 15.4 |
| Run No. 2 | neuro-2a | Control | | 12/136 (8.8), 11/150 (7.4), 11/145 (7.6) | 7.9 |
| | | Isaxinone | 1 | 25/221 (11.3), 29/213 (13.6), 24/209 (11.5) | 12.1 |
| | | (604) | 1 | 35/203 (17.2), 39/199 (19.6), 43/190 (22.6) | 19.8 |
| | | | 10 | 27/190 (14.2), 41/211 (19.4), 37/205 (18.0) | 17.2 |
| | | (408) | 1 | 44/143 (30.8), 43/160 (26.9), 38/150 (25.3) | 27.7 |
| | | | 10 | 37/142 (26.1), 41/168 (24.4), 39/159 (24.5) | 25.0 |
| | | (616) | 1 | 34/199 (17.1), 32/211 (15.2), 27/181 (14.9) | 15.7 |
| | | | 10 | 35/189 (18.5), 41/221 (18.6), 32/178 (18.0) | 18.4 |

TABLE 2-continued

| | | | Activity on cell lines GOTO and neuro-2a (simple method) | | |
|---|---|---|---|---|---|
| | | Compound | Concentration (μg/ml) | Number of cells having neurites with a length equal to, or larger than, the long diameter of the cell/total number of cells (%) | Average of the proportions (%) |
| | | (802) | 1 | 41/215 (19.1), 43/207 (20.8), 37/197 (18.8) | 19.6 |
| | | | 10 | 37/206 (18.0), 29/202 (14.4), 28/199 (14.1) | 15.5 |
| Run No. 3 | neuro-2a | Control | | 1/43 (2.3), 1/65 (1.5), 2/90 (2.2) | 2.0 |
| | | Isaxinone | 0.1 | 10/99 (10.1), 10/118 (8.5), 6/69 (8.7) | 9.1 |
| | | | 1 | 11/120 (9.2), 13/144 (9.0), 10/109 (9.2) | 9.1 |
| | | (604) | 0.01 | 9/83 (11.0), 10/95 (10.5), 13/124 (10.5) | 10.7 |
| | | | 0.1 | 20/110 (18.2), 12/79 (15.2), 11/75 (16.0) | 16.5 |
| | | | 1 | 16/132 (12.1), 13/121 (11.0), 12/114 (10.5) | 11.2 |
| | | (620) | 0.01 | 13/125 (10.4), 18/124 (14.5), 18/128 (14.1) | 13.0 |
| | | | 0.1 | 10/63 (15.9), 13/78 (16.7), 15/110 (13.6) | 15.4 |
| | | | 1 | 10/103 (9.7), 8/96 (8.3), 12/105 (11.4) | 9.8 |

TABLE 3

Activity on neuro-2a

| Compound | Number of cells having neurites with a length at least twice as large as the long diameter of cell/total number of cells, % (compound concentration) |
|---|---|
| Run No. 1 | |
| (124) | 4.6 ± 0.5 (3.6 μM), 3.8 ± 1.2 (36 μM) |
| (132) | 4.3 ± 0.5 (27 μM), 4.3 ± 1.2 (0.27 μM), 4.2 ± 1.0 (0.027 μM) |
| (128) | 5.2 ± 0.9 (28 μM), 4.4 ± 0.7 (0.028 μM), 3.4 ± 0.6 (0.29 μM) |
| Control | 2.2 ± 0.8 |
| Run No. 2 | |
| (108) | 6.9 ± 1.6 (1 mM), 4.6 ± 1.2 (0.3 mM) |
| (104) | 10.6 ± 4.6 (0.3 mM), 5.3 ± 1.8 (1 mM) |
| (112) | 3.5 ± 0.5 (1 mM) |
| (120) | 10.2 ± 3.7 (0.1 mM) |
| (132) | 11.2 ± 1.3 (0.3 mM), 9.1 ± 3.0 (1 mM), 4.4 ± 0.7 (0.1 mM) |
| (136) | 7.2 ± 1.7 (0.1 mM) |
| (144) | 19.4 ± 3.2 (0.3 mM), 9.9 ± 1.5 (0.1 mM) |
| (652) | 4.5 ± 0.3 (1 mM) |
| (442) | 9.1 ± 0.8 (1 mM), 7.1 ± 2.6 (0.3 mM), 5.7 ± 0.5 (0.1 mM) |
| Control | 1.9 ± 0.9 |
| Run No. 3 | |
| (604) | 10.7 ± 1.3 (1 mM), 8.6 ± 0.9 (0.3 mM) |
| (408) | 51.2 ± 1.5 (0.1 mM), 23.0 ± 1.7 (0.05 mM), 13.0 ± 1.2 (0.03 mM), 7.9 ± 1.8 (0.01 mM) |
| (412) | 44.2 ± 1.4 (1 mM), 16.6 ± 2.6 (0.3 mM) |
| (428) | 30.1 ± 2.4 (1 mM), 17.3 ± 0.8 (0.3 mM) 6.7 ± 1.5 (0.03 mM) |
| Isaxinone | 7.0 ± 0.8 (1 mM), 6.8 ± 1.2 (0.1 mM), 4.7 ± 0.4 (0.03 mM) |
| Control | 3.9 ± 0.3 |
| Run No. 4 | |
| (412) | 47.8 ± 0.4 (1 mM), 27.9 ± 2.9 (0.5 mM), 15.8 ± 2.3 (0.3 mM) |
| (408) | 44.6 ± 3.1 (0.2 mM), 33.5 ± 2.7 (0.1 mM), 16.8 ± 2.7 (0.05 mM) |
| (406) | 44.8 ± 0.8 (0.5 mM), 29.9 ± 2.6 (0.3 mM), 16.2 ± 3.7 (0.1 mM) |
| (428) | 29.1 ± 2.4 (1 mM), 27.2 ± 3.1 (0.5 mM), 13.7 ± 2.1 (0.1 mM) |
| (430) | 13.4 ± 0.4 (1 mM), 11.7 ± 1.8 (0.5 mM), 7.2 ± 1.9 (0.1 mM) |
| (464) | 13.1 ± 1.1 (1 mM), 10.1 ± 1.9 (0.3 mM), 7.1 ± 1.6 (0.1 mM) |
| (918) | 12.5 ± 0.9 (1 mM), 7.4 ± 2.5 (0.1 mM) |
| Isaxinone | 34.4 ± 0.6 (10 mM), 13.6 ± 2.3 (3 mM), 5.7 ± 1.2 (1 mM) |
| Control | 3.1 ± 0.2 |
| Run No. 5 | |
| (206) | 6.7 ± 0.7 |
| (424) | 27.1 ± 2.1 (1 mM), 12.6 ± 1.1 (0.5 mM) |
| (408) | 23.5 ± 2.5 (0.1 mM), 12.8 ± 1.8 (0.05 mM) |
| Run No. 5 | |
| (707) | 36.1 ± 3.7 (1 mM), 6.1 ± 0.5 (0.01 mM) |
| (701) | 54.9 ± 1.61 (mM), 16.2 ± 1.2 (0.1 mM) |
| (406) | 32.4 ± 4.3 (0.5 mM), 18.4 ± 3.0 (0.3 mM), 7.6 ± 1.8 (0.03 mM) |
| (428) | 15.6 ± 1.0 (1 mM), 14.1 ± 1.5 (0.5 mM), 9.8 ± 2.3 (0.3 mM) |
| (430) | 9.0 ± 0.8 (1 mM), 7.6 ± 0.8 (0.3 mM) |
| (466) | 13.1 ± 1.4 (1 mM), 5.4 ± 0.3 (0.1 mM) |
| Isaxinone | 27.0 ± 3.4 (10 mM), 6.8 ± 2.2 (1 mM) |
| Control | 4.5 ± 0.3 |
| Run No. 6 | |
| (902) | 6.9 ± 0.8 (0.01 mM), 6.7 ± 0.9 (0.03 mM), 6.7 ± 1.0 (1 mM) |
| (202) | 5.6 ± 1.1 (0.1 mM) |
| (906) | 7.4 ± 1.0 (0.1 mM), 7.0 ± 0.6 (0.3 mM) |
| (602) | 10.0 ± 0.9 (3 mM), 6.2 ± 0.2 (0.1 mM) |
| (616) | 10.6 ± 1.5 (0.3 mM), 10.3 ± 1.4 (1 mM) |
| (802) | 7.5 ± 2.2 (0.1 mM) |
| (620) | 20.7 ± 2.5 (3 mM), 10.5 ± 3.2 (1 mM), 7.2 ± 0.3 (0.1 mM) |
| (606) | 11.9 ± 2.1 (3 mM), 6.9 ± 1.8 (0.1 mM) |
| Isaxinone | 29.9 ± 0.9 (10 mM) |
| Control | 4.4 ± 0.9 |
| Run No. 7 | |
| (408) | 44.5 ± 2.9 (0.2 mM), 25.0 ± 2.7 (0.1 mM), 6.2 ± 0.9 (0.01 mM) |
| (406) | 40.2 ± 3.4 (0.5 mM), 22.6 ± 2.2 (0.3 mM), 10.3 ± 1.6 (0.1 mM) |
| (707) | 21.4 ± 1.7 (1 mM), 10.5 ± 1.5 (0.5 mM), 7.3 ± 1.0 (0.3 mM) |
| (701) | 57.2 ± 1.2 (1 mM), 42.5 ± 1.8 (0.5 mM), 6.8 ± 0.8 (0.03 mM) |
| Isaxinone | 24.9 ± 1.0 (10 mM) |
| Control | 2.5 ± 0.7 |
| Run No. 8 | |
| (420) | 47.5 ± 0.6 (1 mM), 30.6 ± 5.0 (0.5 mM), 16.5 ± 2.1 (0.3 mM) |
| (410) | 36.7 ± 6.1 (0.5 mM), 22.4 ± 2.9 (0.3 mM), 15.5 ± 0.3 (1 mM) |
| (412) | 49.5 ± 3.5 (0.5 mM), 32.6 ± 1.3 (1 mM), 18.4 ± 0.5 (0.3 mM) |
| (414) | 43.6 ± 7.8 (1 mM), 33.4 ± 2.6 (0.5 mM), 15.0 ± 4.0 (0.3 mM) |
| (416) | 48.7 ± 5.7 (0.5 mM), 40.4 ± 9.2 (0.3 mM), 11.7 ± 3.3 (0.1 mM) |
| (418) | 47.4 ± 1.6 (1 mM), 29.6 ± 3.3 (0.5 mM), 16.6 ± 1.1 (0.3 mM) |
| (502) | 7.8 ± 1.2 (1 mM), 5.5 ± 2.0 (0.3 mM) |
| Isaxinone | 28.2 ± 1.6 (10 mM) |
| Control | 3.7 ± 0.4 |
| Run No. 9 | |
| (620) | 19.6 ± 0.5 (3 mM), 11.3 ± 3.3 (1 mM), 6.2 ± 1.5 (0.3 mM) |
| (436) | 15.6 ± 7.3 (0.1 mM), 14.3 ± 2.9 (0.03 mM), 12.5 ± 6.2 (0.3 mM) |
| (434) | 6.0 ± 1.2 (0.1 mM) |
| (440) | 12.9 ± 4.1 (3 mM), 5.8 ± 1.0 (1 mM) |

TABLE 3-continued

Activity on neuro-2a

| Compound | Number of cells having neurites with a length at least twice as large as the long diameter of cell/total number of cells, % (compound concentration) |
|---|---|
| (442) | 13.8 ± 1.2 (3 mM), 7.5 35 3.0 (1 mM) |
| (140) | 3.7 ± 1.4 (0.03 mM) |
| (638) | 6.5 ± 0.2 (0.1 mM) |
| (642) | 14.4 ± 4.0 (0.3 mM), 9.5 ± 1.2 (0.1 mM) |
| (446) | 9.2 ± 2.0 (1 mM), 6.3 ± 0.4 (0.5 mM) |
| Control | 2.0 ± 1.0 |
| Run No. 10 | |
| 116 | 11.6 ± 2.0 (0.03 mM), 10.6 ± 4.5 (0.1 mM), 7.5 ± 2.2 (0.01 mM) |
| 120 | 6.5 ± 1.7 (0.1 mM), 2.6 ± 0.6 (0.003 mM) |
| 136 | 16.4 ± 0.9 (0.03 mM), 12.6 ± 1.4 (0.1 mM), 5.8 ± 1.6 (0.01 mM) |
| 468 | 15.7 ± 0.5 (1 mM), 5.8 ± 0.8 (0.3 mM) |
| 646 | 7.3 ± 0.2 (0.1 mM) |
| 914 | 4.9 ± 0.9 (0.1 mM), 4.6 ± 0.8 (0.3 mM) |
| 470 | 5.4 ± 2.1 (3 mM), 4.6 ± 1.5 (1 mM), 3.2 ± 0.7 (0.3 mM) |
| Isaxinone | 30.0 ± 1.1 |
| Control | 1.7 ± 0.7 |
| Run No. 11 | |
| 940 | 17.0 ± 1.2 (0.3 mM), 11.5 ± 0.2 (0.1 mM) |
| 674 | 6.7 ± 1.3 (0.1mM), 4.5 ± 1.9 (0.3 mM), 4.2 ± 0.8 (0.03 mM) |
| 678 | 16.1 ± 1.6 (1 mM), 9.1 ± 2.2 (3 mM), 4.1 ± 2.2 (0.1 mM) |
| Control | 2.5 ± 0.6 |

Example 2C

Curative effect on rats with crushed sciatic nerves:

The curing effect of the compound (I) of the invention was tested on rats having crushed scietic nerves as a model of peripheral nervous disorder using (1) a change in the action of the hind paw with the crushed sciatic nerves and (2) a change in the weight of the muscle as an index of the course of degeneration and regeneartion of peripheral nerves.

In the experiment, male Wistar rats (6 weeks old), seven per group, were used. The sciatic nerves were crushed by a method similar to the method of Yamatsu et al. (see Kiyomi Yamatsu, Takenori Kaneko, Akifumi Kitahara and Isao Ohkawa, Journal of Japanese Pharmacological Society, 72, 259–268 (1976) and the method of Hasegawa et al. (see Kazuo Hasegawa, Naoji Mikuni and Yutaka Sakai, Journal of Japanese Pharmacological Society, 74, 721–734 (1978). Specifically, under anesthesia with pentobarbital (40 mg/kg, i.p.), the left side sciatic nerve was exposed at the femur and that site of the exposed scietic nerve which was 5 mm to the center from the branched part between the N. tibialis and the N. suralis was crushed using a modified artery, klomme, having a width of 2 mm and a gap of 0.1 mm. After the operation, the rats were assigned to the test groups at random.

Compound No. 408 was selected as the compound (I) of the invention and intraperitoneally administered to the rats once a day from the day of operation to the 22nd day. A group to which mecobalamin (made by Gedeon Richter Ltd.) was administered and a group to which 0.9% saline was administered were used as controls. The following items were measured with the lapse of time (on the 1st, 4th, 7th, 10th, 14th, 17th, 21st, and 23rd days after the crushing of the scietic nerves).

(1) Change in the action of the side of the hind paw with the crushed scietic nerve:

The distance between digits was measured because this is a good index which functionally shows the degeneration and regeneration of the nerve and its change can be measured with the lapse of time.

By a method similar to the method of Hasegawa [Hasegawa, K., Experientia, 34, 750–751 (1978)], the distance between the first and fifth digits of the hind paw was measured.

The ratio of the measured distance to the normal distance was calculated and expressed in percentage (%). The average calculated values and the standards errors (S.E.) are shown in Table 4. To the values of the test groups which are significantly different, by the t-test of Student, from that of the control group to which physiological saline was administered, superscript* is attached where $p<0.05$ and superscript**, where $p<0.01$.

The distance between the digits was about half (50%) of the normal distance immediately after the crushing of the sciatic nerve, and tended to decline until the tenth day. No significant difference was seen among the groups. Regeneration proceeded in the drug-administered groups on the 14th and 17th days, but they showed no significant difference from the group to which saline was administered. On the 21st day, there was an apparent tendency to quicker recovery in the drug-administered groups and the mecobbalamin-administered group, and these groups also show significant differences from the group to which saline was administered. Recovery continued also on the 23rd day.

(2) Change in the weight of muscle

It is known that removal of a nerve or its disorder causes atrophy of the muscle which is under its control, and the atrophy is gradually cured by re-control by the nerve. For this reason, a change in the weight of the muscle, which is quantitative, was selected as an index. Twenty-three days after the operation, the soleus muscles of both sides of paws were extracted under anesthesia with pentobarbital, and their weights were measured. The ratio of the weight of the soleus muscle on the crushed side to that of normal side was calculated and expressed in percentage (%). The average values and the standard errors (S.E.) of the groups are shown in Table 4.

According to experience with another experiment, the weight of the muscle in the saline-administered group began to decrease two days after the crushing of the sciatic nerve and became about 90% of the normal value. In 10 to 14 days, it reached about 40%, the lowest value, and the atrophy of the muscle reached a maximum. Thereafter, the atrophy began to cure gradually.

In the present experiment, it is clear that in the groups to which the compound of the invention was administered, the recovery of the weight of the muscle was promoted dose-dependently with a significant difference from the saline-adminsitered group on the 21st day.

TABLE 4

Curative effect with rats crushed in the sciatic nerve

| Drug | Dose (mg/kg · ip) | Rate of recovery of the interdigit distance (%) | | Rate of recovery in muscle weight (%) |
|---|---|---|---|---|
| | | 21st day | 23rd day | 23rd day |
| Saline | 1 ml/kg | 62.0 ± 2.4 | 71.1 ± 3.4 | 51.8 ± 1.2 |
| Compound 408 | 3 | 70.9 ± 3.5 | 80.1 ± 3.6 | 58.0 ± 2.0* |
| | 10 | 74.9 ± 3.1* | 82.3 ± 2.7* | 59.4 ± 2.2* |
| | 30 | 79.6 ± 2.9*** | 85.4 ± 4.1* | 59.3 ± 2.7* |
| | 100 | 68.9 ± 4.3 | 77.3 ± 6.0 | 63.9 ± 3.5* |
| Mecobalamin | 0.5 | 79.1 ± 2.6*** | 88.3 ± 4.0** | 55.0 ± 3.5 |

Comparison with the saline-administered group by the student t-test
*P < 0.05
**P < 0.01
***P < 0.001
Rats used: Seven per group Example 3C Promoting effect on the improvement of motor imbalance due to injury of the rat's brain cells by transplantation of fetal cerebral cells:

Nigral dopaminergic nerve cells at the left side of the brain of 4-week old female Wistar rats (body weight 100 g) were lesioned by injecting a very small quantity of 6-hydroxydopamine. The rats showed a tendency to rotate spontaneously in a direction opposite to the lesioned side for several days, but no apparent abnormal action was observed after that. Upon administration of methamphethamine (5 mg/kg, i.p.) to the rats having the lesioned nigral dopaminergic nerve cells, they began rotational movement toward the lesioned side.

After two weeks from the destruction by the administration of the drug, portions of the truncus corporis callosi containing dopamine cells (i.e., substantia nigra and the tagmentum at the abdomen side) were cut from the brain of a fetal rat of 14 to 17 days of age, cut finely, and treated with trypsin. Then, the extracted tissues were incubated at 37° C. for 30 minutes, and the tissues were subjected to pipetting to form a suspension. Five microliters of the suspension was transplanted each into two sites of the caudate nucleus of the lesioned side (10 microliters in total, about $10^5$ cells).

Each of the compounds (I) in a dose of 100 mg/kg (i.p.) was administered every day over two weeks from the day of transplantation. The rotational movements induced by administration of methamphetamine were examined 2 weeks and 1 week before, and 2 weeks and 4 weeks after, the transplantation and the administration of the drug. The number of rotational movements within one minute was counted at intervals of 10 minutes after the administration of methamphetamine, and the total number of rotational movements counted six times was averaged to find a mean number of the rotational movements.

The results are shown in Table 5.

TABLE 5

Effect of the drug on the methamphetamine-induced rotational movement of rats

| | | Number of rotational movements of rats and average values thereof (mean ± S.D.) Number of weeks after transplantation of nigral dopamine cells | | | |
|---|---|---|---|---|---|
| | Compound | −2W | −1W | 2W | 4W |
| Run No. 1 | 604 | 10.6 ± 3.82 | 10.4 ± 5.75 | 2.99 ± 2.91 | 3.37 ± 1.65 |
| | 408 | 8.57 ± 2.36 | 12.27 ± 2.48 | 4.9 ± 2.38 | 2.03 ± 1.56 |
| | Saline | 10.9 ± 4.57 | 12.23 ± 4.88 | 5.9 ± 2.75 | 3 ± 3.23 |
| Run No. 2 | 604 | 13.33 ± 4.9 | 11.28 ± 4.0 | 1.03 ± 2.9 | 0.75 ± 2.8 |
| | 408 | 10.94 ± 6.4 | 11.06 ± 4.5 | 1.94 ± 2.0 | 1.53 ± 2.1 |
| | Saline | 12 ± 3.95 | 10 ± 5.3 | 4.4 ± 5.9 | 1.5 ± 3.2 |

Rats used in Run No. 1: Three per group
Rats used in Run No. 2: Six per group (5 per group only in the measurement after 4 weeks)

The results given in Table 5 demonstrate that the rats, two and four weeks after administration of the drug, showed less numbers of rotational movements than the rats to which saline was administered, and the compounds (I) have an effect of repairing and regenerating the nerves and an effect of recovering motor function.

Example 4C

The acute toxicity of the compounds of the invention was examined by the following method.

Male ddy-strain 5-week old mice and male Wistar-strain 8 week old rats, five per group, were used as experimental animals. Each of the compounds was dissolved in saline and administered perorally, and the toxicity of the compound was assessed 24 hours after the administration. The results are shown in Tables 6 and 7.

TABLE 6

| | | Acute toxicity (LD$_{50}$) | | | |
|---|---|---|---|---|---|
| | | Number of dead animals/ number of test animals Dose (mg/kg p.o.) | | | Presumed LD$_{50}$ |
| Animal | Compound | 300 | 500 | 1000 | (mg/kg p.o.) |
| Mouse | (710) | 0/5 | 3/5 | 5/5 | 300–550 |
| | (706) | 0/5 | 2/5 | 4/5 | 550–1000 |
| | (744) | — | 0/5 | 3/5 | 550–1000 |
| | (701) | 0/5 | 3/5 | 5/5 | 300–550 |
| | (715) | 0/5 | 0/5 | 4/5 | 550–1000 |
| | (713) | 0/5 | 0/5 | 2/5 | >1000 |
| | (144) | 0/5 | 0/5 | 3/5 | 550–1000 |
| | (120) | 0/5 | 1/5 | 4/5 | 550–1000 |
| | (124) | 0/5 | 0/5 | 3/5 | 550–1000 |
| | (128) | 0/5 | 3/5 | 4/5 | 300–550 |

TABLE 6-continued

| | | Acute toxicity (LD$_{50}$) | | | |
|---|---|---|---|---|---|
| | | Number of dead animals/ number of test animals Dose (mg/kg p.o.) | | | Presumed LD$_{50}$ |
| Animal | Compound | 300 | 500 | 1000 | (mg/kg p.o.) |
| Rat | (710) | 1/5 | 2/5 | 5/5 | 550–1000 |
| | (706) | 0/5 | 1/5 | 3/5 | 550–1000 |

— Not carried out.

TABLE 7

| | | Acute toxicity (LD$_{50}$) | | | |
|---|---|---|---|---|---|
| | | Number of dead animals/ number of test animals Dose (mg/kg p.o.) | | | Presumed LD$_{50}$ |
| Animal | Compound | 1000 | 1700 | 3000 | (mg/kg p.o.) |
| Mouse | 620 | 0/5 | — | — | >1000 |
| | 602 | 0/5 | 0/5 | 3/5 | 1700–3000 |
| | 606 | 0/5 | — | — | >1000 |
| | 608 | 0/5 | — | — | >1000 |
| | 616 | 0/5 | 0/5 | 4/5 | 1700–3000 |
| | 424 | 0/5 | — | — | >1000 |
| | 406 | 1/5 | — | — | >1000 |
| | 502 | 0/5 | — | — | >1000 |
| | 428 | 0/5 | — | — | >1000 |
| | 604 | 0/5 | — | — | >1000 |
| | 408 | 0/5 | — | — | >1000 |
| | 438 | 0/5 | — | — | >1000 |
| | 650 | 0/5 | — | — | >1000 |
| | 132 | 0/5 | — | — | >1000 |
| | 678 | 0/5 | — | — | >1000 |
| | 468 | 1/5 | — | — | >1000 |
| Rat | 602 | — | 0/5 | — | >1700 |
| | 616 | — | 0/5 | — | >1700 |

— Not carried out.

EFFECTS OF THE INVENTION

The compounds of general formula (I) provided by this invention have a promoting effect on the proliferation of nerve cells and the formation and sprouting of neurites and a nerve regenerating effect and a motor function recovering effect in rats and mice having nerve disorders, and can be used suitably for improving and curing neurological diseases such as diorders of peripheral nerves or central nerves. They are expected to be used also suitably for the recovery, improving and curing of neurological diseases caused by nervous tissues and cells which have to do with perceptive and sensory functions and an automatic function.

It has been found that the compounds (I) of the invention have biological activities equal to, or higher than, those of isaxonine as a control as shown in Example 1C, Tables 1, 2 and 3. The toxicity of the compounds (I) of this invention are generally weak as shown in Example 4C, Tables 6 and 7. Thus, the compounds (I) of this invention are generally considered to be highly active and highly safe drugs with weak toxicity.

What is claimed is:

1. A pharmaceutical composition for neurological diseases in the form of a tablet, capsule, troche, cachet, elixir, ointment, aseptic injectable, molded cataplasm, tape, suppository or aseptic powder comprising as an active ingredient a pyrimidine represented by the following formula (I)

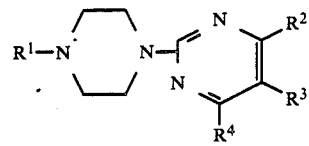

wherein R$^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, R$^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, R$^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms, or a hydroxyethyl group, R$^2$ and R$^3$ may together form a group selected from

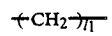

wherein l$_1$ is a number of 2, 3 or 4,

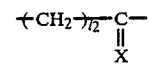

wherein X is =O or =N—R$^5$ in which R$^5$ is a hydroxyl, benzenesulfonyloxy or toluenesulfonyloxy group, and l$_2$ is a number of 2, 3 or 4,

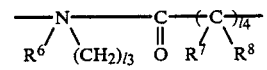

wherein R$^6$ represents a hydrogen atom, an alkyl group having 1 to 4 carbon atoms, or an alkoxyalkyl group resulting from substitution of an alkyl group having 2 to 4 carbon atoms by an alkoxy group having 1 to 4 carbon atoms, R$^7$ and R$^8$ are identical or different and each represents a hydrogen atom or an alkyl group having 1 to 4 carbon atoms and l$_3$ is 2 and l$_4$ is 0, or l$_3$ is 0 and l$_4$ is 1,

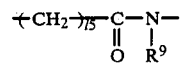

wherein R$^9$ represents a hydrogen atom or an alkyl group having 1 to 4 carbon atoms, and l$_5$ is a number of 2 or 3,

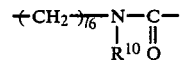

wherein R$^{10}$ represents a hydrogen atom, an alkyl group having 1 to 10 carbon atoms, an acyl group having 1 to 4 carbon atoms or a carbmoylmethyl group, and l$_6$ is a number of 1 or 2,

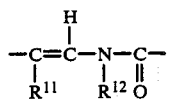

wherein $R^{11}$ represents a hydrogen atom, a formyl group, an alkyl group having 1 to 4 carbon atoms or an aralkyl group having 7 to 9 carbon atoms and $R^{12}$ represents a hydrogen atom, an alkyl group having 1 to 4 carbon atoms, an alkenyl group having 3 to 4 carbon atoms, a hydroxyalkyl group having 2 to 4 carbon atoms, an alkoxyalkyl group resulting from substitution of an alkyl group having 2 to 4 carbon atoms by an alkoxy group having 2 to 4 carbon atoms, a benzyl group or a cycloalkyl group having 3 to 6 carbon atoms,

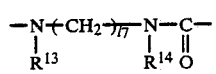

wherein $R^{13}$ and $R^{14}$ are identical or different and each represents a hydrogen atom or an alkyl group having 1 to 4 carbon atoms, and $l_7$ is a number of 0, 2 or 3, or

—E—G— wherein —E—G— is —OCH$_2$CH$_2$—, —OC(CH$_3$)=CH—, —CH$_2$OCO—, —OCOCH$_2$—, —CH$_2$C(CH$_3$)OCO—, —N(CH$_3$)CH$_2$CH$_2$—, —CH=CH—CH=CH—, —CH=C(OCH$_3$)—C(OCH$_3$)=CH—, or

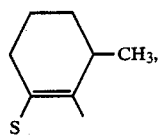

and $R^4$ represents a hydrogen atom, an alkyl group having 1 to 4 carbon atoms, or an alkylthio group having 1 to 4 carbon atoms, with the proviso that $R^1$, $R^2$, $R^3$ and $R^4$ are not hydrogen at the same time, or a pharmaceutically acceptable salt thereof; and a pharmaceutically acceptable carrier therefor.

2. The pharmaceutical composition set forth in claim 1 wherein the active ingredient is a pyrimidine represented by the following formula (I)-a

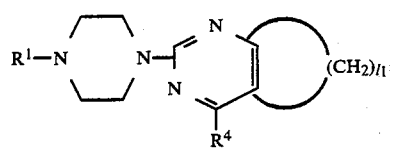

wherein $R^1$ and $R^4$ are as defined with regard to formula (I), and $l_1$ is a number of 2, 3 or 4, or its pharmaceutically acceptable salt.

3. The pharmaceutical composition set forth in claim 1 wherein the active ingredient is a pyrimidine represented by the following formula (I)-b

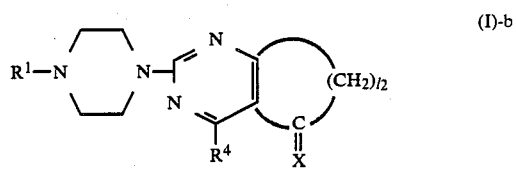

wherein $R^1$ and $R^4$ are as defined with regard to formula (I), X is =O or =N—$R^5$ in which $R^5$ is a hydroxyl, benzensulfonyloxy or toluenesulfonyloxy group, and $l_2$ is a number of 2, 3 or 4, or its pharmaceutically acceptable salt.

4. The pharmaceutical composition set forth in claim 1 wherein the active ingredient is a pyrimidine represented by the following formula (I)-c

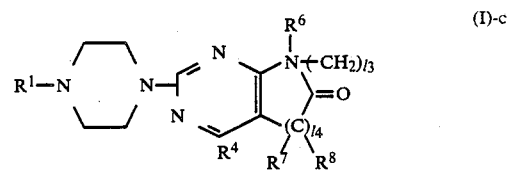

wherein $R^1$ and $R^4$ are as defined in regard to formula (I), $R^6$ represents a hydrogen atom, an alkyl group having 1 to 4 carbon atoms, or an alkoxyalkyl group resulting from substitution of an alkyl group having 2 to 4 carbon atoms by an alkoxy group having 1 to 4 carbon atoms, $R^7$ and $R^8$ are identical or different and each represents a hydrogen atom or an alkyl group having 1 to 4 carbon atoms, and $l_3$ is 2 and $l_4$ is 0, or $l_3$ is 0 and $l_4$ is 1, or its pharmaceutically acceptable salt.

5. The pharmaceutical composition set forth in claim 1 wherein the active ingredient is a pyrimidine represented by the following formula (I)-d

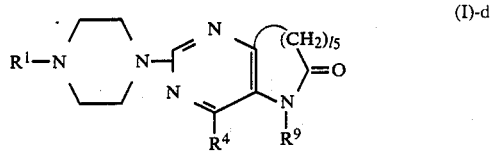

wherein $R^1$ and $R^4$ are as defined with regard to formula (I), $R^9$ represents a hydrogen atom or an alkyl group having 1 to 4 carbon atoms, and $l_5$ is a number of 2 or 3, or its pharmaceutically acceptable salt.

6. The pharmaceutical composition set forth in claim 1 wherein the active ingredient is a pyrimidine represented by the following formula (I)-e

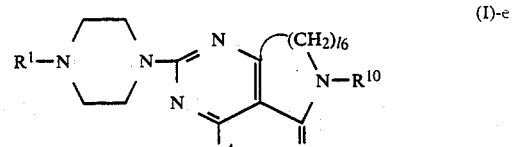

wherein $R^1$ and $R^4$ are as defined with regard to formula (I), and $R^{10}$ represents a hydrogen atom, an alkyl group having 1 to 10 carbon atoms, an acyl group having 1 to 4 carbon atoms, or a carbamoylmethyl group, and $l_6$ is a number of 1 or 2, or its pharmaceutically acceptable salt.

7. The pharmaceutical composition set forth in claim 1 wherein the active ingredient is a pyrimidine represented by the following formula (I)-f

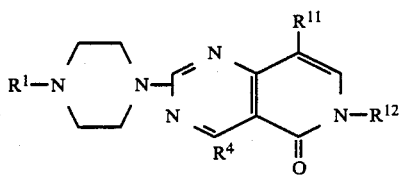

wherein $R^1$ and $R^4$ are as defined with regard to formula (I), $R^{11}$ represents a hydrogen atom, a formyl group, an alkyl group having 1 to 4 carbon atoms or an aralkyl group having 7 to 9 carbon atoms, and $R^{12}$ represents a hydrogen atom, an alkyl group having 1 to 4 carbon atoms, an alkenyl group having 3 to 4 carbon atoms, a hydroxyalkyl group having 2 to 4 carbon atoms, an alkoxyalkyl group resulting from substitution of an alkyl group having 2 to 4 carbon atoms by an alkoxy group having 2 to 4 carbon atoms, a benzyl group, or a cycloalkyl group having 3 to 6 carbon atoms,
or its pharmaceutically acceptable salt.

8. The pharmaceutical composition set forth in claim 1 wherein the active ingredient is a pyrimidine represented by the following formula (I)-g

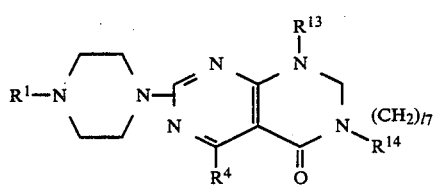

wherein $R^1$ and $R^4$ are as defined with regard to formula (I), $R^{13}$ and $R^{14}$ are identical or different and each represents a hydrogen atom or an alkyl group having 1 to 4 carbon atoms, and $l_7$ is a number of 0, 2 or 3,
or its pharmaceutically acceptable salt.

9. The pharmaceutical composition set forth in claim 1 wherein the active ingredient is a pyrimidine represented by the following formula (I)-h

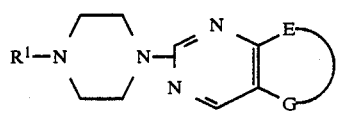

wherein $R^1$ and $R^4$ are as defined with regard to formula (I), and E-G is $-OCH_2CH_2-$, $-OC(CH_3)=CH-$, $-CH_2OCO-$, $-O-COCH_2-$, $-CH_2C(CH_3)OCO-$, $-N(CH_3)CH_2CH_2-$, $-CH=CH-CH=CH-$, $-CH=C(OCH_3)-C(OCH_3)=CH-$, or

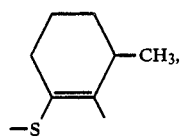

or its pharmaceutically acceptable salt.

10. The pharmaceutical composition set forth in claim 1 wherein the pharmaceutically acceptable salt is selected from a hydrochloride, hydrobromide, sulfate, bisulfite, phosphate, acidic phosphate, acetate, maleate, fumarate, succinate, lactate, tartrate, benzoate, citrate, gluconate, glucanate, methanesulfonate, p-toluene-sulfonate, naphthalenesulfonate and quaternary ammonium salt.

11. The pharmaceutical composition set forth in claim 1, in unit dosage form containing 0.1 to 2000 mg of said active ingredient.

12. The pharmaceutical composition set forth in claim 11, wherein said unit dosage form contains 0.5 to 1000 mg of said active ingredient.

13. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

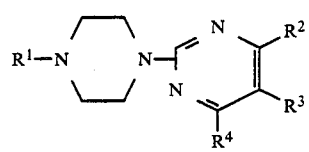

wherein $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms, or a hydroxyethyl group, $R^2$ and $R^3$ may together form a group selected from

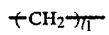

wherein $l_1$ is a number of 2, 3 or 4,

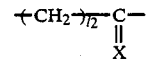

wherein X is $=O$ or $=N-R^5$ in which $R^5$ is a hydroxyl, benzenesulfonyloxy or toluenesulfonyloxy group, and $l_2$ is a number of 2, 3 or 4,

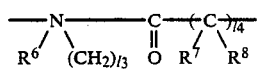

wherein $R^6$ represents a hydrogen atom, an alkyl group having 1 to 4 carbon atoms, or an alkoxyalkyl group resulting from substitution of an alkyl group having 2 to 4 carbon atoms by an alkoxy group having 1 to 4 carbon atoms, $R^7$ and $R^8$ are identical or different and each represents a hydrogen atom or an alkyl group having 1 to 4 carbon atoms and $l_3$ is 2 and $l_4$ is 0, or $l_3$ is 0 and $l_4$ is 1,

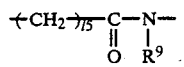

wherein $R^9$ represents a hydrogen atom or an alkyl group having 1 to 4 carbon atoms, and
$l_5$ is a number of 2 or 3,

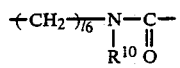

wherein $R^{10}$ represents a hydrogen atom, an alkyl group having 1 to 10 carbon atoms, an acyl group having 1 to 4 carbon atoms or a carbamoylmethyl group, and $l_6$ is a number of 1 or 2,

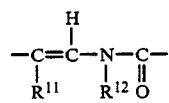

wherein $R^{11}$ represents a hydrogen atom, a formyl group, an alkyl group having 1 to 4 carbon atoms or an aralkyl group having 7 to 9 carbon atoms and $R^{12}$ represents a hydrogen atom, an alkyl group having 1 to 4 carbon atoms, an alkenyl group having 3 to 4 carbon atoms, a hydroxyalkyl group having 2 to 4 carbon atoms, an alkoxyalkyl group resulting from substitution of an alkyl group having 2 to 4 carbon atoms by an alkoxy group having 2 to 4 carbon atoms, a benzyl group or a cycloalkyl group having 3 to 6 carbon atoms,

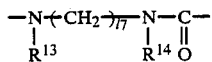

wherein $R^{13}$ and $R^{14}$ are identical or different and each represents a hydrogen atom or an alkyl group having 1 to 4 carbon atoms, and $l_7$ is a number of 0, 2 or 3, or
—E—G—
wherein —E—G— is —OCH$_2$CH$_2$—, —OC(CH$_3$)═CH—, —CH$_2$OCO—, —OCOCH$_2$—, —CH$_2$C(CH$_3$)OCO—, —N(CH$_3$)CH$_2$CH$_2$—, —CH═CH—CH═CH—, —CH═C(OCH$_3$)—C(OCH$_3$)═CH—, or

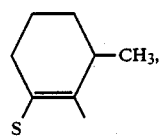

and
$R^4$ represents a hydrogen atom, an alkyl group having 1 to 4 carbon atoms, or an alkylthio group having 1 to 4 carbon atoms, or a pharmaceutically acceptable salt thereof.

14. The method set forth in claim 13 wherein the active ingredient is a pyrimidine represented by the following formula (I)-a

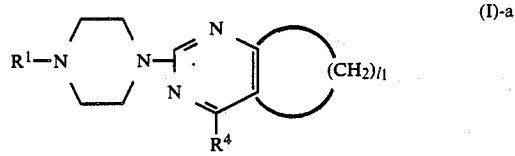

wherein $R^1$ and $R^4$ are as defined with regard to formula (I), and $l_1$ is a number of 2, 3 or 4,
or its pharmaceutically acceptable salt.

15. The method set forth in claim 13 wherein the active ingredient is a pyrimidine represented by the following formula (I)-b

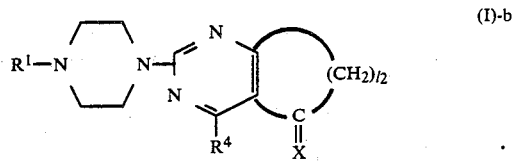

wherein $R^1$ and $R^4$ are as defined with regard to formula (I), X is ═O or ═N—$R^5$ in which $R^5$ is a hydroxyl, benzenesulfonyloxy or toluenesulfonyloxy group, and $l_2$ is a number of 2, 3 or 4,
or its pharmaceutically acceptable salt.

16. The method set forth in claim 13 wherein the active ingredient is a pyrimidine represented by the following formula (I)-c

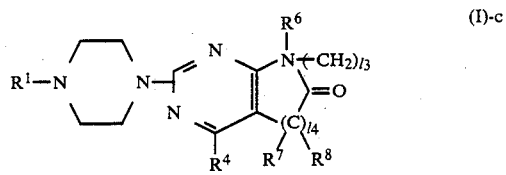

wherein $R^1$ and $R^4$ are as defined in regard to formula (I), $R^6$ represents a hydrogen atom, an alkyl group having 1 to 4 carbon atoms, or an alkoxyalkyl group resulting from substitution of an alkyl group having 2 to 4 carbon atoms by an alkoxy group having 1 to 4 carbon atoms, $R^7$ and $R^8$ are identical or different and each represents a hydrogen atom or an alkyl group having 1 to 4 carbon atoms, and $l_3$ is 2 and $l_4$ is 0, or $l_3$ is 0 and $l_4$ is 1,
or its pharmaceutically acceptable salt.

17. The method set forth in claim 13 wherein the active ingredient is a pyrimidine represented by the following formula (I)-d

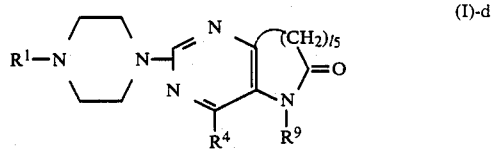

wherein $R^1$ and $R^4$ are as defined with regard to formula (I), $R^9$ represents a hydrogen atom or an alkyl group having 1 to 4 carbon atoms, and $l_5$ is a number of 2 or 3, or its pharmaceutically acceptable salt.

18. The method set forth in claim 13 wherein the active ingredient is a pyrimidine represented by the following formula (I)-e

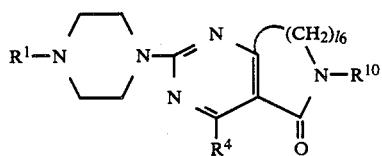
(I)-e wherein $R^1$ and $R^4$ are as defined with regard to formula (I), and $R^{10}$ represents a hydrogen atom, an alkyl group having 1 to 10 carbon atoms, an acyl group having 1 to 4 carbon atoms, or a carbamoylmethyl group, and $l_6$ is a number of 1 or 2, or its pharmaceutically acceptable salt.

19. The method set forth in claim 13 wherein the active ingredient is a pyrimidine represented by the following formula (I)-f

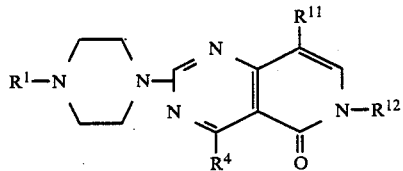
(I)-f wherein $R^1$ and $R^4$ are as defined with regard to formula (I), $R^{11}$ represents a hydrogen atom, a formyl group, an alkyl group having 1 to 4 carbon atoms, or an aralkyl group having 7 to 9 carbon atoms, and $R^{12}$ represents a hydrogen atom, an alkyl group having 1 to 4 carbon atoms, an alkenyl group having 3 to 4 carbon atoms, a hydroxyalkyl group having 2 to 4 carbon atoms, an alkoxyalkyl group resulting from substitution of an alkyl group having 2 to 4 carbon atoms by an alkoxy group having 2 to 4 carbon atoms, a benzyl group, or a cycloalkyl group having 3 to 6 carbon atoms, or its pharmaceutically acceptable salt.

20. The method set forth in claim 13 wherein the active ingredient is a pyrimidine represented by the following formula (I)-g

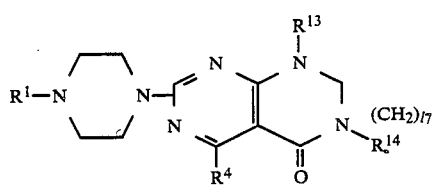
(I)-g wherein $R^1$ and $R^4$ are as defined with regard to formula (I), $R^{13}$ and $R^{14}$ are identical or different and each represents a hydrogen atom or an alkyl group having 1 to 4 carbon atoms, and $l_7$ is a number of 0, 2 or 3, or its pharmaceutically acceptable salt.

21. The method set forth in claim 13 wherein the active ingredient is a pyrimidine represented by the following formula (I)-h

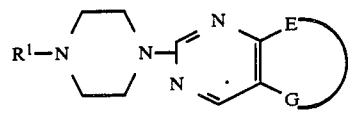
(I)-h wherein $R^1$ and $R^4$ are as defined with regard to formula (I), and E—G is —OCH$_2$CH$_2$—, —OC(CH$_3$)=CH—, —CH$_2$OCO—, —O-COCH$_2$—, —CH$_2$C(CH$_3$)OCO—, —N(CH$_3$)CH$_2$CH$_2$—, —CH=CH—CH=CH—, —CH=C(OCH$_3$)—C(OCH$_3$)=CH—, or

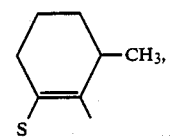

or its pharmaceutically acceptable salt.

22. The method set forth in claim 13 wherein the pharmaceutically acceptable salt is selected from a hydrochloride, hydrobromide, sulfate, bisulfite, phosphate, acidic phosphate, acetate, maleate, fumarate, succinate, lactate, tartrate, benzoate, citrate, gluconate, glucanate, methanesulfonate, p-toluene-sulfonate, naphthalenesulfonate and quaternary ammonium salt.

23. A pyrimidine represented by the following formula

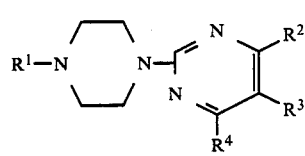
(I)

wherein $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, $R^2$ and $R^3$ may together form a group selected from

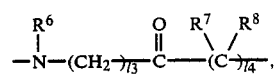

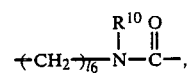

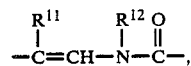

-continued $$-\overset{R^{13}}{\underset{|}{N}}-\overset{R^{14}}{\underset{|}{N}}-\overset{O}{\underset{||}{C}}-, \text{ or}$$

—E—G—, and

R⁴ represents a hydrogen atom, an alkyl group having 1 to 4 carbon atoms, or an alkylthio group having 1 to 4 carbon atoms, with the proviso that R¹, R², R³ and R⁴ are not hydrogen at the same time; and wherein $l_1$ is a number of 2, 3 or 4, R⁶ is an alkoxy alkyl group resulting from substitution of an alkyl group having 2 to 4 carbon atoms by an alkoxy group having 1 to 4 carbon atoms, R⁷ and R⁸ are identical or different and each represents an alkyl group having 1 to 4 carbon atoms, $l_3$ is 0 or 2, $l_4$ is 0 or 1, and $l_3$ is 2 when $l_4$ is 0 and $l_3$ is 0 when $l_4$ is 1, R¹⁰ represents an acyl group having 1 to 4 carbon atoms or a carbamoylmethyl group, $l_6$ is a number of 1 or 2, R¹¹ represents a hydrogen atom, a formyl group, an alkyl group having 1 to 4 carbon atoms or an aralkyl group having 7 to 9 carbon atoms, R¹² represents a hydrogen atom, an alkyl group having 1 to 4 carbon atoms, an alkenyl group having 3 to 4 carbon atoms, a hydroxylalkyl group having 2 to 4 carbon atoms, an alkoxyalkyl group resulting from substitution of an alkyl group having 2 to 4 carbon atoms by an alkoxy group having 1 to 4 carbon atoms, a benzyl group or a cycloalkyl group having 3 to 6 carbon atoms, R¹³ and R¹⁴ are identical or different, and each represents a hydrogen atom or an alkyl group having 1 to 4 carbon atoms, and —E—G— is —OCH₂CH₂—, —OC(CH₃)=CH—, —CH₂OCO—, —OCOCH₂—, —CH₂C(CH₃)OCO—, —N(CH₃)CH₂CH₂—, —CH=CH—CH=CH—, —CH=C(OCH₃)—C(OCH₃)=CH— or <chemical structure> or a pharmaceutically acceptable salt thereof.

24. The pyrimidine according to claim 23, wherein R² and R³ form the group $$+CH_2\overline{)l_1}-.$$

25. The pyrimidine according to claim 23, wherein R² and R³ form the group $$-\overset{R^6}{\underset{|}{N}}+CH_2\overline{)l_3}-\overset{O}{\underset{||}{C}}+\overset{R^7}{\underset{|}{C}}-\overset{R^8}{\underset{|}{}}\overline{)l_4}-.$$

26. The pyrimidine according to claim 23, wherein R² and R³ form the group $$+CH_2\overline{)l_6}-\overset{R^{10}}{\underset{|}{N}}-\overset{O}{\underset{||}{C}}-.$$

27. The pyrimidine according to claim 23, wherein R² and R³ form the group $$-\overset{R^{11}}{\underset{|}{C}}=CH-\overset{R^{12}}{\underset{|}{N}}-\overset{O}{\underset{||}{C}}-.$$

28. The pyrimidine according to claim 23, wherein R² and R³ form the group $$-\overset{R^{13}}{\underset{|}{N}}-\overset{R^{14}}{\underset{|}{N}}-\overset{O}{\underset{||}{C}}-.$$

29. The pyrimidine according to claim 23, wherein R² and R³ form the group
—E—G—.

30. A pharmaceutical composition for neurological diseases comprising, as an active ingredient, a pyrimidine according to claim 23 and a pharmaceutically acceptable carrier therefor.

31. A pharmaceutical composition for neurological diseases comprising, as an active ingredient, a pyrimidine according to claim 24 and a pharmaceutically acceptable carrier therefor.

32. A pharmaceutical composition for neurological diseases comprising, as an active ingredient, a pyrimidine according to claim 25 and a pharmaceutically acceptable carrier therefor.

33. A pharmaceutical composition for neurological diseases comprising, as an active ingredient, a pyrimidine according to claim 26 and a pharmaceutically acceptable carrier therefor.

34. A pharmaceutical composition for neurological diseases comprising, as an active ingredient, a pyrimidine according to claim 27 and a pharmaceutically acceptable carrier therefor.

35. A pharmaceutical composition for neurological diseases comprising, as an active ingredient, a pyrimidine according to claim 28 and a pharmaceutically acceptable carrier therefor.

36. A pharmaceutical composition for neurological diseases comprising, as an active ingredient, a pyrimidine according to claim 29 and a pharmaceutically acceptable carrier therefor.

37. A method for treating a patient having a neurological disease comprising a disorder of the peripheral nerves or central nerves requiring the proliferation of nerve cells, the formation and sprouting of neurites, nerves regeneration or motor function recovery, said method comprising administering to said patient a neurologically effective amount of a pyrimidine represented by the following formula <chemical structure, formula (I)> wherein R¹ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, R² represents a hydrogen atom, an amino group, a monoalkylamino group having 1 to 4 carbon atoms, an alkoxy group having 1 to 5 carbon atoms or an alkoxycarbonyl group having 2 to 4 carbon atoms, R³ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, R² and R³ may together form a group selected from

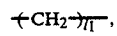

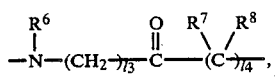

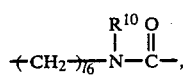

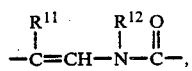

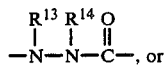

—E—G—, and

R⁴ represents a hydrogen atom, an alkyl group having 1 to 4 carbon atoms, or an alkylthio group having 1 to 4 carbon atoms; and wherein l₁ is a number of 2, 3 or 4, R⁶ is an alkoxy alkyl group resulting from substitution of an alkyl group having 2 to 4 carbon atoms by an alkoxy group having 1 to 4 carbon atoms, R⁷ and R⁸ are identical or different and each represents an alkyl group having 1 to 4 carbon atoms, l₃ is 0 or 2, l₄ is 0 or 1, and l₃ is 2 when l₄ is 0 and l₃ is 0 when l₄ is 1, R¹⁰ represents an acyl group having 1 to 4 carbon atoms or a carbamoylmethyl group, l₆ is a number of 1 or 2, R¹¹ represents a hydrogen atom, a formyl group, an alkyl group having 1 to 4 carbon atoms or an aralkyl group having 7 to 9 carbon atoms, R¹² represents a hydrogen atom, an alkyl group having 1 to 4 carbon atoms, an alkenyl group having 3 to 4 carbon atoms, a hydroxylalkyl group having 2 to 4 carbon atoms, an alkoxyalkyl group resulting from substitution of an alkyl group having 2 to 4 carbon atoms by an alkoxy group having 1 to 4 carbon atoms, a benzyl group or a cycloalkyl group having 3 to 6 carhon atoms, R¹³ and R¹⁴ are identical or different, and each represents a hydrogen atom or an alkyl group having 1 to 4 carbon atoms, and —E—G— is —OCH₂CH₂—, —OC(CH₃)=CH—, —CH₂OCO—, —OCOCH₂—, —CH₂C(CH₃)OCO—, —N(CH₃)CH₂CH₂—, —CH=CH—CH=CH—, —CH=C(OH₃)—C(OCH₃)=CH— or

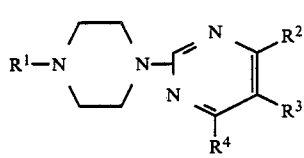

or a pharmaceutically acceptable salt thereof.

38. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

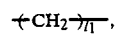

(I)

wherein R¹ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, R² represents a hydrogen atom, an amino group, a monoalkylamino group having 1 to 4 carbon atoms, an alkoxy group having 1 to 5 carbon atoms or an alkoxycarbonyl group having 2 to 4 carbon atoms, R³ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, R² and R³ may together form a group selected from

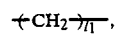

R⁴ represents a hydrogen atom, an alkyl group having 1 to 4 carbon atoms, or an alkylthio group having 1 to 4 carbon atoms; and wherein l₁ is a number of 2, 3 or 4; or a pharmaceutically acceptable salt thereof.

39. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

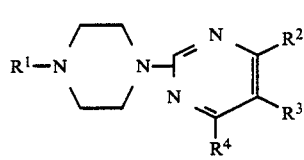

(I)

wherein R¹ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, $R^2$ and $R^3$ may together form a group

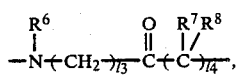

$R^4$ represents a hydrogen atom, an alkyl group having 1 to 4 carbon atoms, or an alkylthio group having 1 to 4 carbon atoms; and wherein $R^6$ is an alkoxy alkyl group resulting from substitution of an alkyl group having 2 to 4 carbon atoms by an alkoxy group having 1 to 4 carbon atoms, $R^7$ and $R^8$ are identical or different and each represents an alkyl group having 1 to 4 carbon atoms, $l_3$ is 0 or 2, $l_4$ is 0 or 1, and $l_3$ is 2 when $l_4$ is 0 and $l_3$ is 0 when $l_4$ is 1; or a pharmaceutically acceptable salt thereof.

40. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

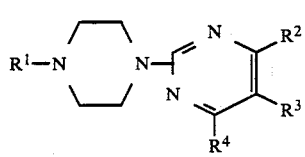

wherein $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, $R^2$ and $R^3$ may together form a group

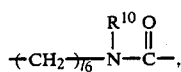

$R^4$ represents a hydrogen atom, an alkyl group having 1 to 4 carbon atoms, or an alkylthio group having 1 to 4 carbon atoms; and wherein $R^{10}$ represents an acyl group having 1 to 4 carbon atoms or a carbamoylmethyl group, $l_6$ is a number of 1 to 2; or a pharmaceutically acceptable salt thereof.

41. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

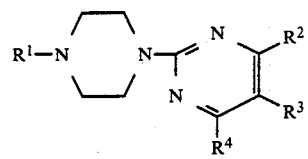

wherein $R^1$ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenozyl group or a 3,4-methylenedioxybenzyl group, $R^2$ represents a hydrogen atom, an amino group, a monoalkylamino group having 1 to 4 carbon atoms, an alkoxy group having 1 to 5 carbon atoms or an alkoxycarbonyl group having 2 to 4 carbon atoms, $R^3$ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, $R^2$ and $R^3$ may together form a group

$R^4$ represents a hydrogen atom, an alkyl group having 1 to 4 carbon atoms, or an alkylthio group having 1 to 4 carbon atoms; and wherein $R^{11}$ represents a hydrogen atom, a formyl group, an alkyl group having 1 to 4 carbon atoms or an aralkyl group having 7 to 9 carbon atoms, $R^{12}$ represents a hydrogen atom, an alkyl group having 1 to 4 carbon atoms, an alkenyl group having 3 to 4 carbon atoms, a hydroxylalkyl group having 2 to 4 carbon atoms, an alkoxyalkyl group resulting from substitution of an alkyl group having 2 to 4 carbon atoms by an alkoxy group having 1 to 4 carbon atoms, a benzyl group or a cycloalkyl group having 3 to 6 carbon atoms; or a pharmaceutically acceptable salt thereof.

42. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

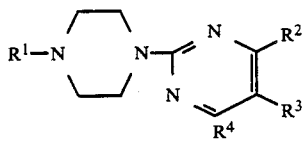

wherein R¹ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, R² represents a hydrogen atom, an amino group, a monoalkylamino group having 1 to 4 carbon atoms, an alkoxy group having 1 to 5 carbon atoms or an alkoxycarbonyl group having 2 to 4 carbon atoms, R³ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, R² and R³ may together form a group

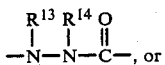

R⁴ represents a hydrogen atom, an alkyl group having 1 to 4 carbon atoms, or an alkylthio group having 1 to 4 carbon atoms; and wherein R¹³ and R¹⁴ are identical or different, and each represents a hydrogen atom or an alkyl group having 1 to 4 carbon atoms; or a pharmaceutically acceptable salt thereof.

43. A method for treating a patient having a neurological disease comprising a disorder of the peripheral nerves or central nerves requiring the proliferation of nerve cells, the formation and sprouting of neurites, nerve regeneration or motor function recovery, said method comprising administering to said patient a neurologically effective amount of a pyrimidine represented by the following formula (I)

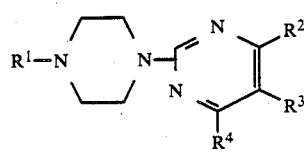

wherein R¹ represents a hydrogen atom, an acyl group having 2 to 4 carbon atoms, an alkoxycarbonyl group having 2 to 5 carbon atoms, an alkoxycarbonylmethyl group having 3 to 5 carbon atoms, a 3,4-dimethoxybenzoyl group or a 3,4-methylenedioxybenzyl group, R² represents a hydrogen atom, an amino group, a monoalkylamino group having 1 to 4 carbon atoms, an alkoxy group having 1 to 5 carbon atoms or an alkoxycarbonyl group having 2 to 4 carbon atoms, R³ represents a hydrogen atom, an alkoxycarbonyl group having 2 to 4 carbon atoms, a dialkylaminocarbonyl group having 1 to 9 carbon atoms in each alkyl moiety, an alkoxy group having 1 to 5 carbon atoms or a hydroxyethyl group, R² and R³ may together form a group
—E—G—;

R⁴ represents a hydrogen atom, an alkyl group having 1 to 4 carbon atoms, or an alkylthio group having 1 to 4 carbon atoms; and wherein —E—G— is —OCH₂CH₂—, —OC(CH₃)=CH—, —CH₂OCO—, —OCOCH₂—, —CH₂C(CH₃)OCO—, —N(CH₃)CH₂CH₂—, —CH=CH—CH=CH—, —CH=C(OH)—C(OCH₃)=CH— or

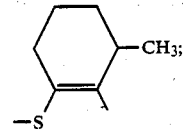

or a pharmaceutically acceptable salt thereof.

* * * * *

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

It is certified that error appears in the above-identified patent and that said Letters Patent is hereby corrected as shown below:

Col. 68
Claim 1, delete Formula (I), insert

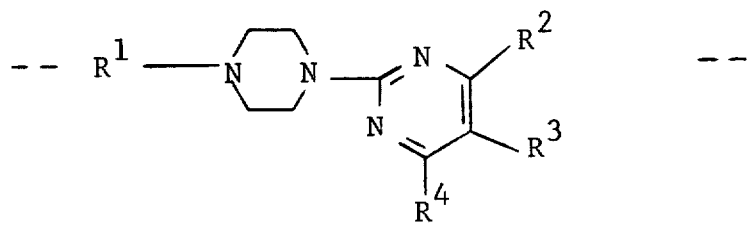

Col. 69
Claim 2, delete Formula (I)-a, insert

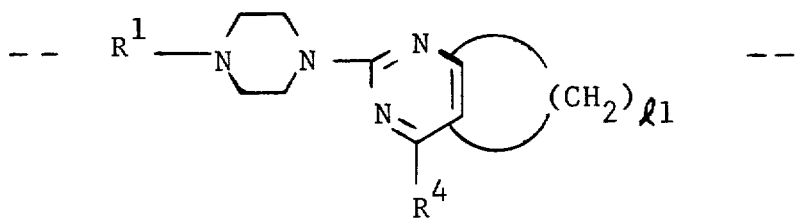

UNITED STATES PATENT AND TRADEMARK OFFICE
CERTIFICATE OF CORRECTION

PATENT NO. : 4,959,368
DATED : September 25, 1990
INVENTOR(S) : AWAYA, ET AL.

It is certified that error appears in the above-identified patent and that said Letters Patent is hereby corrected as shown below:

Col. 70;
Claim 3, delete Formula (I)-b), insert

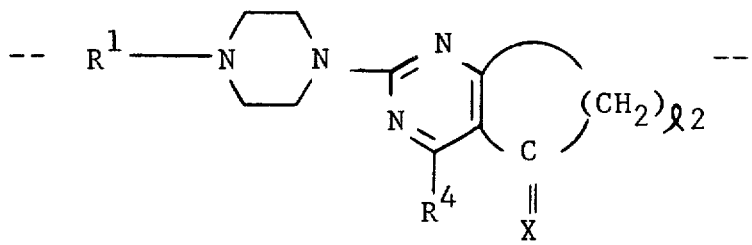

Col. 70;
Claim 4, delete Formula (I)-c, insert

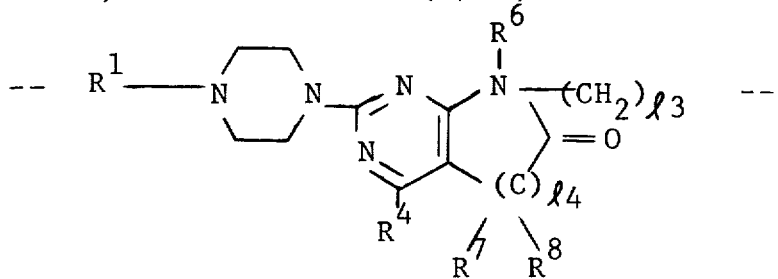

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

It is certified that error appears in the above-identified patent and that said Letters Patent is hereby corrected as shown below:

Col. 70;
Claim 5, delete Formula (I)-d, insert

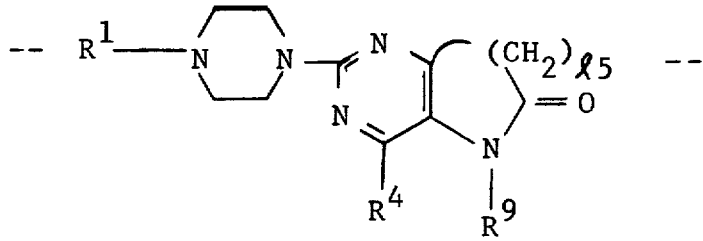

Col. 71;
Claim 7, delete Formula (I)-f, insert

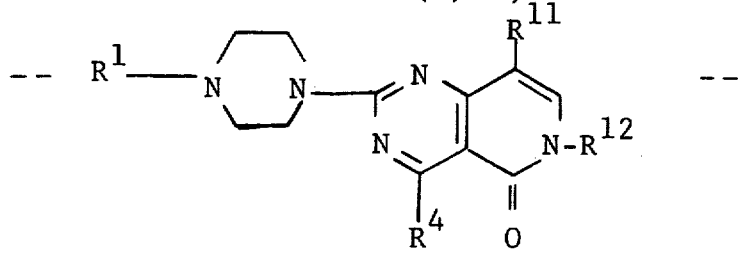

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

Page 4 of 12

It is certified that error appears in the above-identified patent and that said Letters Patent is hereby corrected as shown below:

Col. 71;
Claim 8, delete Formula (I)-g, insert

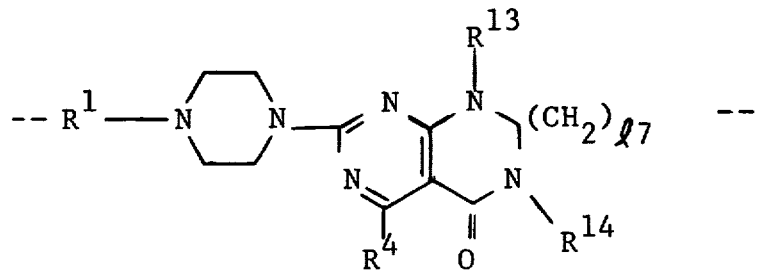

Col. 71;
Claim 9, delete Formula (I)-h, insert

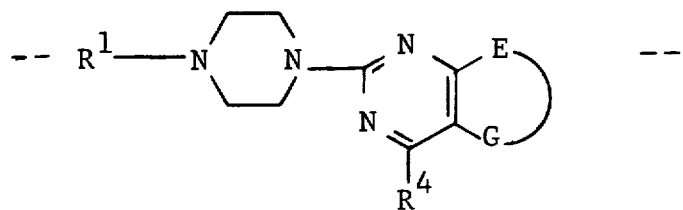

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

It is certified that error appears in the above-identified patent and that said Letters Patent is hereby corrected as shown below:

Col. 72;
Claim 13, delete Formula (I), insert

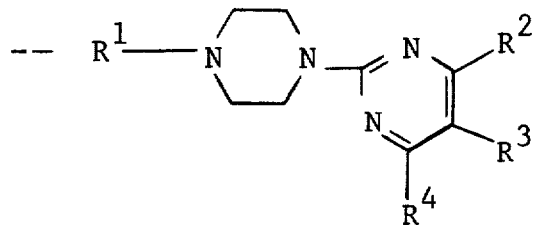

Col. 73, line 67, delete "or a pharmaceutically".

Line 68, Before "acceptable", insert --or a pharmaceutically--.

UNITED STATES PATENT AND TRADEMARK OFFICE
CERTIFICATE OF CORRECTION

PATENT NO. : 4,959,368  Page 6 of 12
DATED : September 25, 1990
INVENTOR(S) : AWAYA, ET AL.

It is certified that error appears in the above-identified patent and that said Letters Patent is hereby corrected as shown below:

Col. 74;
Claim 14, delete Formula (I)-a, insert

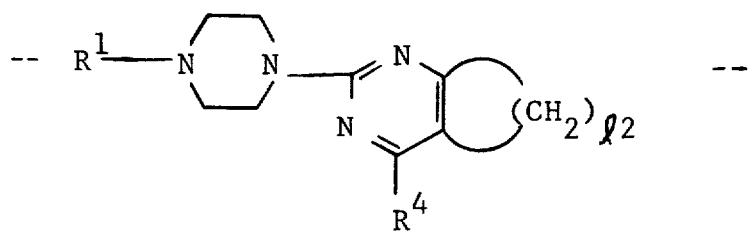

Col. 74;
Claim 15, delete Formula (I)-b, insert

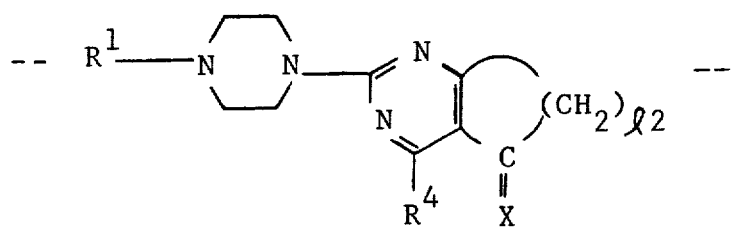

UNITED STATES PATENT AND TRADEMARK OFFICE
CERTIFICATE OF CORRECTION

PATENT NO. : 4,959,368
DATED : September 25, 1990
INVENTOR(S) : AWAYA, ET AL.

It is certified that error appears in the above-identified patent and that said Letters Patent is hereby corrected as shown below:

Col. 74;
Claim 16, delete Formula (I)-c, insert

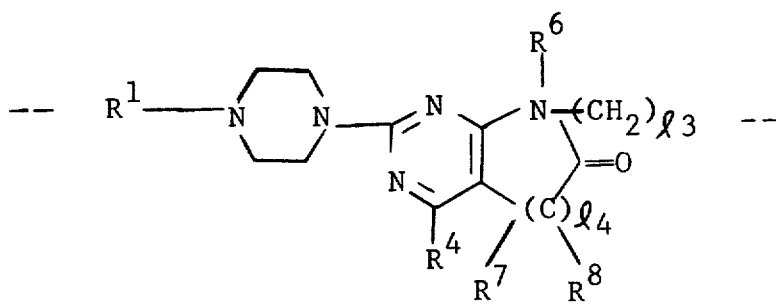

Col. 74;
Claim 17, delete Formula (I)-d, insert

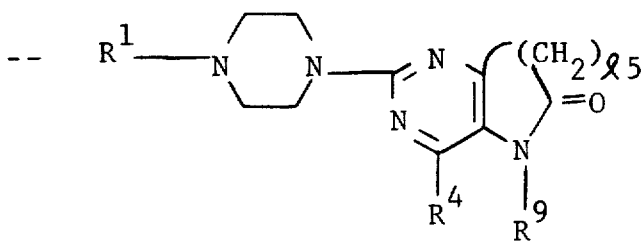

UNITED STATES PATENT AND TRADEMARK OFFICE
CERTIFICATE OF CORRECTION

PATENT NO. : 4,959,368
DATED : September 25, 1990
INVENTOR(S) : AWAYA, ET AL.

It is certified that error appears in the above-identified patent and that said Letters Patent is hereby corrected as shown below:

Col. 75;
Claim 19, delete Formula (I)-f, insert

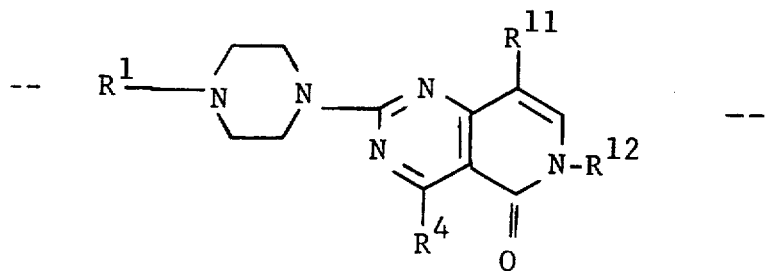

Col. 75;
Claim 20, delete Formula (I)-g, insert

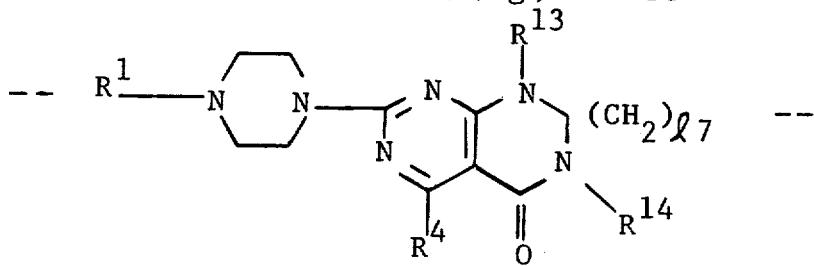

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

It is certified that error appears in the above-identified patent and that said Letters Patent is hereby corrected as shown below:

Col. 76;

Claim 21, delete Formula (I)-h, insert

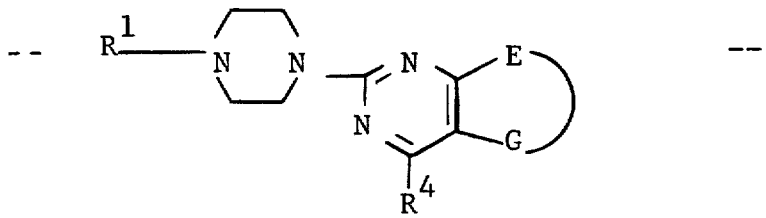

Col. 76;

Claim 23, delete Formula (I), insert

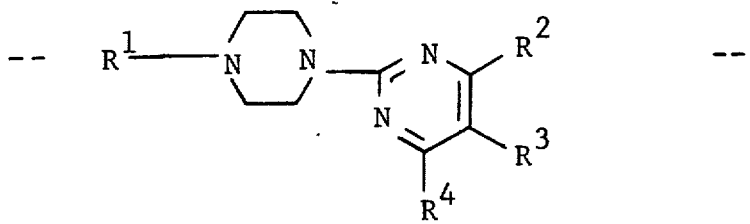

UNITED STATES PATENT AND TRADEMARK OFFICE
CERTIFICATE OF CORRECTION

PATENT NO. : 4,959,368
DATED : September 25, 1990
INVENTOR(S) : AWAYA, ET AL.

It is certified that error appears in the above-identified patent and that said Letters Patent is hereby corrected as shown below:

Col. 77;
Claim 25, delete Formula, insert

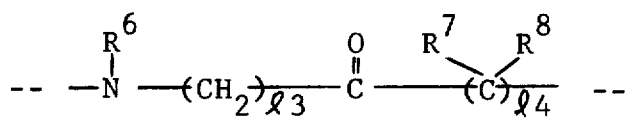

Col. 78;
Claim 37, delete Formula (I), insert

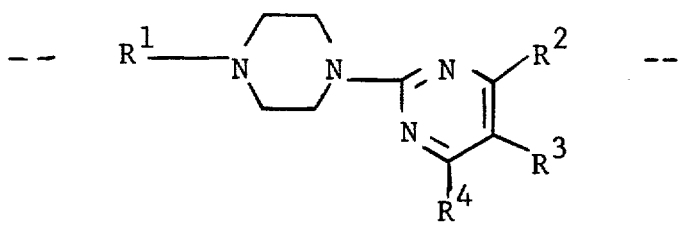

UNITED STATES PATENT AND TRADEMARK OFFICE
CERTIFICATE OF CORRECTION

PATENT NO. : 4,959,368
DATED : September 25, 1990
INVENTOR(S) : AWAYA, ET AL.

It is certified that error appears in the above-identified patent and that said Letters Patent is hereby corrected as shown below:

Col. 78;
Claim 38, delete Formula (I), insert

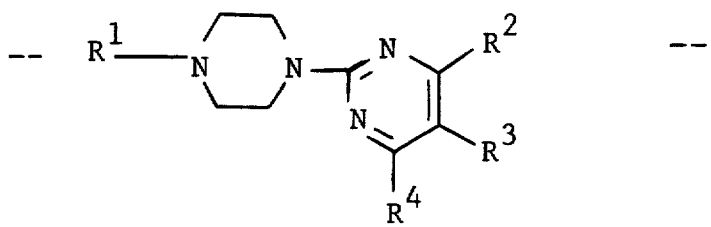

Col. 80;
Claim 39, delete Formula (I), insert

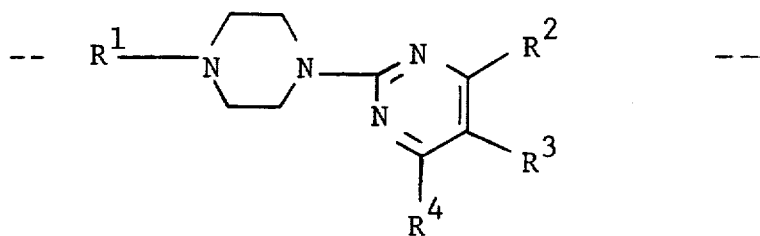

UNITED STATES PATENT AND TRADEMARK OFFICE
CERTIFICATE OF CORRECTION

PATENT NO. : 4,959,368

DATED : September 25, 1990

INVENTOR(S) : AWAYA, ET AL.

It is certified that error appears in the above-identified patent and that said Letters Patent is hereby corrected as shown below:

Col. 81;
Claim 40, delete Formula (I), insert

-- 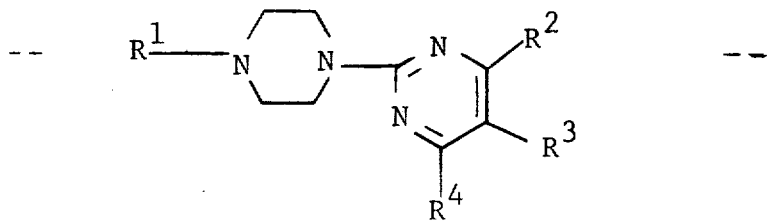 --

Col. 81, line 31, delete "to", insert --or--.

Col. 84;
Claim 43, delete Formula (I), insert

-- 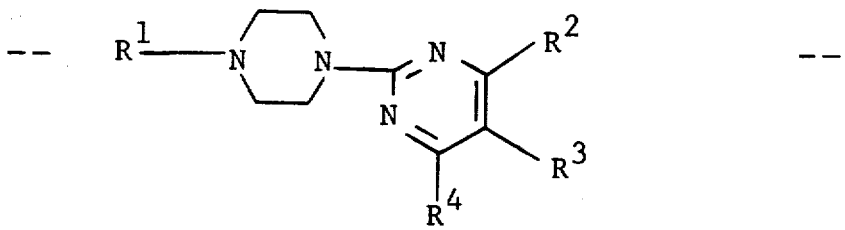 --

Signed and Sealed this

Twenty-second Day of December, 1992

Attest:

DOUGLAS B. COMER

Attesting Officer

Acting Commissioner of Patents and Trademarks